(12) United States Patent
Welmaker et al.

(10) Patent No.: US 7,601,856 B2
(45) Date of Patent: Oct. 13, 2009

(54) BENZOFURANS AS POTASSIUM ION CHANNEL MODULATORS

(75) Inventors: Gregory S. Welmaker, Collegeville, PA (US); Matthew A. Wilson, Royersford, PA (US); Geraldine McFarlane, Monmouth Junction, NJ (US); Joan E. Sabalski, Hamilton, NJ (US); John A. Butera, Clarksburg, NJ (US); Eugene J. Trybulski, Huntingdon Valley, PA (US); David R. Herbst, Wayne, PA (US)

(73) Assignee: Wyeth, Madison, NJ (US)

( * ) Notice: Subject to any disclaimer, the term of this patent is extended or adjusted under 35 U.S.C. 154(b) by 135 days.

(21) Appl. No.: 11/828,457

(22) Filed: Jul. 26, 2007

(65) Prior Publication Data

US 2008/0027049 A1 Jan. 31, 2008

Related U.S. Application Data

(60) Provisional application No. 60/820,524, filed on Jul. 27, 2006, provisional application No. 60/827,817, filed on Oct. 2, 2006.

(51) Int. Cl.
*C07D 307/90* (2006.01)
(52) U.S. Cl. .................................................... 549/461
(58) Field of Classification Search .................. 549/461
See application file for complete search history.

(56) References Cited

U.S. PATENT DOCUMENTS

| | | | |
|---|---|---|---|
| 3,498,988 A | 3/1970 | Houlihan et al. |
| 3,501,475 A | 3/1970 | Humber |
| 3,501,480 A | 3/1970 | Humber et al. |
| 3,501,481 A | 3/1970 | Archibald et al. |
| 3,501,497 A | 3/1970 | Bell |
| 3,507,880 A | 4/1970 | Altwicker |
| 3,509,134 A | 4/1970 | Davis et al. |
| 3,509,184 A | 4/1970 | Conover et al. |
| 3,511,852 A | 5/1970 | Roberts et al. |
| 3,514,461 A | 5/1970 | Albertson |
| 3,518,258 A | 6/1970 | Von Strandthmann et al. |
| 3,518,269 A | 6/1970 | Brown et al. |
| 3,528,991 A | 9/1970 | Bell |
| 3,534,037 A | 10/1970 | Loev |
| 3,534,059 A | 10/1970 | Robinson |
| 3,535,326 A | 10/1970 | Yammamoto et al. |
| 3,538,112 A | 11/1970 | Bell |
| 3,539,557 A | 11/1970 | Davis et al. |
| 3,539,576 A | 11/1970 | Davis et al. |
| 3,539,577 A | 11/1970 | Davis et al. |
| 3,539,588 A | 11/1970 | Salley |
| 3,541,117 A | 11/1970 | Shroff |
| 3,542,787 A | 11/1970 | Dobson et al. |
| 3,549,644 A | 12/1970 | Shavel et al. |
| 3,557,087 A | 1/1971 | Levine |
| 3,557,122 A | 1/1971 | Shavel et al. |
| 3,558,667 A | 1/1971 | Mooradian |
| 3,578,678 A | 5/1971 | Littell et al. |
| 3,579,534 A | 5/1971 | Littell et al. |
| 3,580,926 A | 5/1971 | Short |
| 3,584,009 A | 6/1971 | Gregory |
| 3,590,031 A | 6/1971 | Levine |
| 3,592,824 A | 7/1971 | Schut |
| 3,597,433 A | 8/1971 | Dobson et al. |
| 3,597,436 A | 8/1971 | Huisman et al. |
| 3,598,836 A | 8/1971 | Osaka et al. |
| 3,621,027 A | 11/1971 | Schoen et al. |
| 3,624,126 A | 11/1971 | Narayanan |
| 3,632,591 A | 1/1972 | Albertson et al. |
| 3,642,785 A | 2/1972 | Shen et al. |
| 3,642,836 A | 2/1972 | Cusic |
| 3,651,059 A | 3/1972 | Serino et al. |
| 3,652,544 A | 3/1972 | Levine |
| 3,655,697 A | 4/1972 | Shen et al. |
| 3,657,243 A | 4/1972 | Quintilla |
| 3,663,607 A | 5/1972 | Barrett et al. |
| 3,674,875 A | 7/1972 | Shen et al. |
| 3,679,662 A | 7/1972 | Morita et al. |
| 3,682,985 A | 8/1972 | Bacso et al. |
| 3,687,969 A | 8/1972 | Alexander et al. |

(Continued)

FOREIGN PATENT DOCUMENTS

CA 2417677 7/2001

(Continued)

OTHER PUBLICATIONS

Edwards, G., et al., "Pharmacology of the potassium channel openers", *Cardiovasc. Drugs Ther.*, 9 (Suppl.2): 185-193, 1995.

(Continued)

*Primary Examiner*—D. Margaret Seaman
*Assistant Examiner*—Nizal S Chandrakumar
(74) *Attorney, Agent, or Firm*—Pepper Hamilton LLP

(57) ABSTRACT

The present invention is directed to compounds of Formula I:

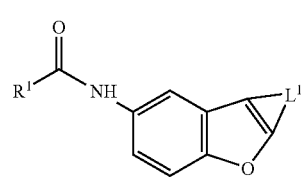

that are potassium channel modulators and pharmaceutical compositions thereof. The present invention is further directed to methods of treatment using the compounds and pharmaceutical compositions of the invention. The present invention is still further directed to synthetic processes for producing the compounds of the invention.

45 Claims, No Drawings

U.S. PATENT DOCUMENTS

| | | | |
|---|---|---|---|
| 3,689,488 A | 9/1972 | Dukes |
| 3,691,243 A | 9/1972 | Fields et al. |
| 3,705,906 A | 12/1972 | Narayanan et al. |
| 3,706,736 A | 12/1972 | Jeger et al. |
| 3,711,511 A | 1/1973 | Jeger et al. |
| 3,717,641 A | 2/1973 | Koesis et al. |
| 3,718,678 A | 2/1973 | Farrand et al. |
| 3,723,483 A | 3/1973 | Coombs |
| 3,726,897 A | 4/1973 | Schindler |
| 3,733,330 A | 5/1973 | Schubert et al. |
| 3,759,948 A | 9/1973 | Shen et al. |
| 3,773,940 A | 11/1973 | Schindler |
| 3,773,949 A | 11/1973 | Macelesfield |
| 3,830,818 A | 8/1974 | Hackmack et al. |
| 3,836,671 A | 9/1974 | Barrett et al. |
| 3,838,135 A | 9/1974 | Magnien et al. |
| 3,865,830 A | 2/1975 | Turkevich et al. |
| 3,865,834 A | 2/1975 | Schubert et al. |
| 3,883,654 A | 5/1975 | Hackmack et al. |
| 3,891,656 A | 6/1975 | Fields |
| 3,928,380 A | 12/1975 | Bell et al. |
| 3,931,288 A | 1/1976 | Berger et al. |
| 3,948,939 A | 4/1976 | Alexander et al. |
| 3,959,309 A | 5/1976 | Mooradian |
| 3,994,887 A | 11/1976 | Crooij et al. |
| 3,997,519 A | 12/1976 | Armbruster |
| 4,018,743 A | 4/1977 | Kraft et al. |
| 4,046,752 A | 9/1977 | Hohmann |
| 4,904,797 A | 2/1990 | Boshagen et al. |
| 5,017,597 A | 5/1991 | Gillard |
| 5,708,187 A | 1/1998 | Flaugh |
| 5,846,995 A | 12/1998 | Flaugh et al. |
| 5,858,995 A | 1/1999 | Kawai et al. |
| 6,476,021 B1 | 11/2002 | Ohashi et al. |

FOREIGN PATENT DOCUMENTS

| | | | |
|---|---|---|---|
| DE | 1210638 | | 2/1966 |
| DE | 4238553 | | 5/1994 |
| EP | 0297651 | | 1/1989 |
| EP | 0344015 | | 11/1989 |
| EP | 0350129 | | 1/1990 |
| EP | 0375045 | | 6/1990 |
| EP | 0425906 | | 10/1990 |
| EP | 0441517 | | 8/1991 |
| EP | 0451634 | | 10/1991 |
| EP | 0468785 | | 1/1992 |
| EP | 0640592 | | 3/1995 |
| EP | 0655451 | | 5/1995 |
| EP | 0749962 | | 12/1996 |
| EP | 0768309 | | 4/1997 |
| EP | 0247266 | | 12/1997 |
| EP | 0992240 | | 4/2000 |
| EP | 1118322 | | 7/2001 |
| EP | 1136072 | | 9/2001 |
| EP | 1462103 | | 9/2004 |
| GB | 1260768 | | 1/1972 |
| GB | 1265627 | | 3/1972 |
| GB | 1299041 | | 12/1972 |
| GB | 1322512 | | 7/1973 |
| GB | 1323302 | | 7/1973 |
| GB | 1323491 | | 7/1973 |
| GB | 1385620 | | 2/1975 |
| GB | 1471847 | | 4/1977 |
| GB | 1519495 | | 7/1978 |
| GB | 1532684 | | 11/1978 |
| GB | 2316405 | | 2/1998 |
| JP | 5001032 | | 1/1993 |
| JP | 61282384 | | 12/1996 |
| JP | WO 2006001318 | * | 5/2006 |
| WO | WO 90/12569 | | 11/1990 |
| WO | WO 92/12144 | | 7/1991 |
| WO | WO 93/00086 | | 1/1993 |
| WO | WO 94/09009 | | 4/1994 |
| WO | WO 94/14773 | | 7/1994 |
| WO | WO 94/25461 | | 11/1994 |
| WO | WO 95/29907 | | 11/1995 |
| WO | WO 98/06717 | | 2/1998 |
| WO | WO 98/53819 | | 12/1998 |
| WO | WO 99/17755 | | 4/1999 |
| WO | WO 99/26946 | | 6/1999 |
| WO | WO 99/28319 | | 6/1999 |
| WO | WO 99/54295 | | 10/1999 |
| WO | WO 00/18391 | | 4/2000 |
| WO | WO 00/24727 | | 5/2000 |
| WO | WO 00/32195 | | 6/2000 |
| WO | WO 00/63171 | | 10/2000 |
| WO | WO 01/45685 | | 6/2001 |
| WO | WO 01/95903 | | 12/2001 |
| WO | WO 02/07713 | | 1/2002 |
| WO | WO 02/34237 | | 5/2002 |
| WO | WO 02/41918 | | 5/2002 |
| WO | WO 02/051806 | | 7/2002 |
| WO | WO 2004/069831 | | 8/2004 |
| WO | WO 2005/037791 | | 4/2005 |
| WO | WO 2006/001318 | | 1/2006 |

OTHER PUBLICATIONS

Foster, D.C., et al., "The effect of potassium channel antagoists on the BRL 34915 activated potassium channel in guinea-pig bladder", *Br. J. Pharmacol.*, 92:751, 1987.

Brading, A.F., "Ion channels and control of contractile activity in urinary bladder smooth muscle", *JPN J. Pharmacol.*, 58 (Suppl.2): 120P-127P, 1992.

Malmgren, A., et al., "Effects of cromakalim (BRL 34915) and pinacidil on normal and hypertrophied rat detrusor in vitro", *J. Urol.*, 143:828-834, 1990.

Grant, T.L., et al., "Effects of K⁻channel blockers and cromakalim (BRL 34915) on the mechanical activity of guinea pig cetruso smooth muscle", *J. Pharmacol. Exp., Ther.*, 269(3):1158-1164, 1991.

Malmgren, A., et al., "Effects of pinacidil and cromakalim (BRL 34915) on bladder function in rats with detrusor instability", *J. Urol.*, 142:1134-1138, 1989.

Wojdan, A., et al., "Comparison of the potassium channel openers ZD6169, celikalim and WAY-133537 on isolated bladder tissue and in vivo bladder instability in the rat", *J. Pharmacol. Exp. Ther.*, 289(3):1410-1418, 1999.

Wickenden, A.D., et al., "Retigabine, a novel anti-convulsant, enhances activation of KCNQ2/Q3 potassium channels", *Molec. Pharmacol.*, 58:591-600, 2000.

Wickenden, A.D., et al., "Characterization of the KCNQ5/Q3 potassium channels expressed in mammalian cells", *Br. J. Pharmacol.*, 132(2):381-384, 2001.

Rundfeldt, C., et al., "The novel anticonvulant retigabine activates M-currents in Chinese hamster ovary-cells transfected with human KCNQ2/3 subuints", *Neurosci. Lett.*, 282(1-2):73-76, 2000.

Main, M.J., et al., "Modulation of KCNQ2/3potassium channels by the novel anticonvulsant retigabine", *Mol. Pharmacol.*, 58(2):253-262, 2000.

Sogaard, R., et al., "KCNQ4 channels expressed in mammalian cells: functional characteristics and pharmacology", *Am. J. Physiol. Cell Physiol.*, 280(4):C859-C866, 2001.

Kubisch, C., et al., "KCNQ4, a novel potassium channel expressed in sensory outer hair cells, is mutated in dominant deafness", *Cell*, 96(3):437-446, 1999.

Rogowski, M.A., "KCNQ2/KCNQ3 K⁺ channels and the molecular pathogenesis of epilepsy: implications for therapy", *Trends Neurosci.*, 23:393-398, 2000.

Jentsch, T.J., "Neuronal KCNQ potassium channels: physiology and role in disease", *Nat. Rev. Neurosci.*, 1(1):21-30, 2000.

Tinel, N., et al., "The KCNQ2 potassium channel: splice variants, functional and developmental expression. Brain localization and comparison with KCNQ3", *FEBS Lett.*, 438(3):171-176, 1998.

Yang, W.P., et al., "Functional expression of two KvLQt1-related potassium channels responsible for an inherited idiopathic epilepsy", *J. Biol. Chem.*, 273(31): 19419-19423, 1998.

Wang, H.S., et al., "KCNQ2 and KCNQ3 potassium channel subunits: molecular correlets of the M-channel", *Science*, 282(5395):1890-1893, 1998.

Lerche, C., et al., "Molecular cloning and functional expression of KCNQ5, a potassium channel subunit that may contribute to neuronal M-current diversity", *J. Biol. Chem.*, 275(29):22395-22400, 2000.

Schroeder, B.C., et al., "KCNQ5, a novel potassium channel broadly expressed in brain, mediates M-type currents", *J. Biol. Chem.*, 275(31):24089-24095, 2000.

Adams, P.R., et al., "M-currents and other potassium currents in bullfrog sympathetic neurons", *J. Physiol.*, 330:537-572, 1982.

Brown, D.A., et al., "Muscarinic suppression of novel voltage-sensitive $K^+$ current in a vertebrate neurone", *Nature*, 283:673-676, 1980.

Shapiro, M.S., et al., "Reconstitution of muscarinic modulation of the KCNQ2/KCNQ3 K(+) channels that underlie the neuronal M current", *J. Neurosci.*, 20(5):1710-1721, 2000.

Aiken, S.P., et al., "Reduction of spike frequency adaptation and blockade of M-current in rat CA1 pyramidal neurons by linopirdine (DuP 996) a neurotransmitter release enhancer", *Br. J. Pharmacol.*, 115(7):1163-1168, 1995.

Zaczek, R., "Two new potent neurotransmitter release enhancers, 10,10-bis(4-pyridinymethyl)-9(10H)-anthracenone and 10,10-bis(2-fluro-4-pyridinylmethyl)-9(10H)-anthracenone: comparison to linopirdine", *J. Pharmacol., Exp.Ther.*, 285(2): 724-730, 1998.

Hashitani, H., et al., "Mechanisms of excitatory neuromuscular transmission in the guinea-pig urinary bladder", *J. Physiol.*, 524(Part 2): 565-579, 2000.

Herrera, G.M., et al., "Voltage dependence of the coupling of CA(2+) sparks to BK(Ca)channels in urinary bladder smooth muscle", *Am. J. Physiol. Cell Physio.*, 280(3):C481-490, 2001.

Jacques, et al., *Enantiomers, Racemates and Resolutions* (Wiley Interscience, New York), 1981.

Eliel, E.L., , *Stereochemistry of Carbon Compounds* (McGraw Hill, New York), 1962.

*Remington's Pharmaceutical Sciences*, 17th ed., Mack Publishing Company, Easton, PA, 1985, p. 1418.

*Journal of Pharmaceutical Science*, 66, 2, 1977.

Higuchi, T., et al., "Pro-drugs as Novel Delivery Systems", vol. 14 of the A.C.S. Symposium Seris.

*Bioreversible Carriers in Drug Design*, ed. Edward B. Roche, American Pharmaceutical Association and Pergamon Press, 1987.

Green et al., *Protective Groups in Organic Synthesis*, 2d., Ed., Wiley & Sons, 1991.

Block, et al., "Discovery and Optimization of a Series of Carbazole Ureas as NPY5 Antagonists for the Treatment of Obesity", *J. Med. Chem.*, 45, 3509, 2002.

Schofield, *Aromatic Nitration*, Cambridge University Press, Cambridge, 1980.

Hogget, et al., *Nitration and Aromatic Reactivity*, 122-145, 163-222, Cambridge University Press, 1971.

Rylander, *Organic Synthesis with Nobel Metal Catalysits*, pp. 1-59, Academic Press, New York, 1973.

Robinson, *The Fischer Indole Synthesis*, Wiley, New York, 1983.

Foster, C.D., et al., "The effect of cromakalim on the smooth muscle of the guinea-pig urinary bladder", *Br. J. Pharmacol.*, 97:281-291, 1989.

Fujii, K., et al., "Potassium channel blockers and the effects of cromakalim on the smooth muscle of the guinea-pig bladder.", *Br. J. Pharmacol.*, 99:779-785, 1990.

Vazanna, I., et al., "7-(substituted amino)-2,3-polymethylenebenzofuran derivatives with tracheal relaxant activity", *Famacao*, 51(10):637-642, 1996.

Hayashi, T., "Tervalent Nitrogen.II. Carbazoleacridone and its several monosubstituted products", *Rikagaku Kenkyusho Iho*, 9:970-90, 1931.

Printout, "Structures from the Registry File available from Chemical Library", pp. 4-9.

Printout, "Structures from the Beilstein File, Answers 1-2", pp. 1-3.

Printout, "Structures from the Registry File, Answers 1-3", pp. 1-2.

Printout, "Structures from the Registry File, Answers 1-8", pp. 1-3.

Printout, "Structures from the Beilstein File, Answers 1-48", pp. 1-5.

Grammaticakis, P., [Preparation and absorption in the visible and ultraviolet region of various amino and nitro N-substituted-1,2,3,4-tetrahydrocarbazoles], *Compt. Rend*, 251, 2728-30, 1960.

Brunton, R.J., et al., "Preparation of indolocarbazoles. IX. Preparation of 9-methylindolo(2',3-1,2)carbazole", *J. Chem. Soc.* 4783-5, cf. C.A. 51,363f, 1956.

Kuroki, N. et al., "Dyes from carbazole derivatives. I. Synthesis of naphthol bases", *J. Soc. Org. Synthet.Chem. Japan*, 12:29-34, 1954.

"Sci-Finder Search Results, pp. 1-19", Chemical Library 2004, 2005.

Wilen, S.H., et al., *Tetrahedron*, 33:2725, 1977.

Wilen, S.H. , Tables of Resolving Agents and Optical Resolutions, p. 268(E.L. Eliel, ed., Univ. of Notre Dame Press, Notre Dame, IN, 1972).

\* cited by examiner

BENZOFURANS AS POTASSIUM ION CHANNEL MODULATORS

This application claims the benefit of priority of U.S. Provisional Application 60/820,524, filed Jul. 27, 2006, and U.S. Provisional Application 60/827,817, filed Oct. 2, 2006, each of which is hereby incorporated by reference in its entirety.

FIELD OF THE INVENTION

The present invention is directed to compounds of Formula I that are potassium channel modulators, pharmaceutical compositions thereof, and methods of using the same. The present invention is further directed to synthetic processes for producing the compounds of the invention.

BACKGROUND OF THE INVENTION

Transmembrane currents play a fundamental role in the activation and functioning of excitable tissues. In urinary bladder smooth muscle, depolarization, excitation-contraction, and repolarization are dependent upon the activation of transmembrane currents through voltage dependent ion channels. The current underlying repolarization in detrusor smooth muscle is carried through several ion channels, virtually all of which utilize potassium as the charge carrier. Several of these channels have been the target of compounds and drugs aimed at modulating the physiology and functioning of smooth muscle and other tissues [Edwards, G & Weston, A H, "Pharmacology of the potassium channel openers", *Cardiovasc Drugs Ther* 9 (Suppl. 2): 185-193 (1995), which is incorporated herein by reference in its entirety].

It has been suggested that a potassium channel opener (KCO) may be useful in the treatment of detrusor hyperactivity [Foster D C & Brading A F, "The effect of potassium channel antagonists on the BRL 34915 activated potassium channel in guinea-pig bladder", *Br J Pharmacol* 92: 751 (1987), which is incorporated herein by reference of in its entirety]. An increase in potassium channel permeability would hyperpolarize the cell, bring the membrane potential further from the threshold for activation of calcium channels and reduce excitability [Brading A F, "Ion channels and control of contractile activity in urinary bladder smooth muscle", *JPN J Pharmacol* 58 (Suppl 2): 120P-127P (1992), which is incorporated herein by reference in its entirety]. A number of potassium channel openers have shown activity in isolated tissues [Malmgren A, et al., "Effects of cromakalim (BRL 34915) and pinacidil on normal and hypertrophied rat detrusor in vitro", *J Urol* 143: 828-834 (1990); Grant T L & Zuzack J S., "Effects of K+ channel blockers and cromakalim (BRL 34915) on the mechanical activity of guinea pig detrusor smooth muscle", *J Pharmacol Exp Ther* 269(3): 1158-1164 (1991), each of which is incorporated herein by reference in its entirety] and efficacy in both experimental and clinical bladder instability [Foster & Brading, supra, *Br J Pharmacol* 92: 751 (1987); Malmgren A, et al., "Effects of pinacidil and cromakalim (BRL 34915) on bladder function in rats with detrusor instability", *J Urol* 142: 1134-1138 (1989); Wojdan A, et al., "Comparison of the potassium channel openers ZD6169, celikalim and WAY-133537 on isolated bladder tissue and in vivo bladder instability in the rat", *J Pharmacol Exp Ther* 289(3): 1410-1418 (1999), each of which is incorporated by reference in its entirety). However, because these compounds also activate channels in vascular smooth muscle, causing vasodilation, the clinical utility has been severely limited by hemodynamic side effects including hypotension and tachycardia.

It has been stated previously that retigabine (N-[2-amino-4-(4-fluorobenzylamino)-phenyl]carbamic acid ethyl ester) activates a member of the KCNQ family of potassium channel in the bladder which is most likely KCNQ2/3 and/or KCNQ3/5 [Wickenden A D, et al., "Retigabine, a novel anticonvulsant, enhances activation of KCNQ2/Q3 potassium channels", *Molec Pharmacol* 58: 591-600 (2000); Wickenden, A D, et al., "Characterization of the KCNQ5/Q3 potassium channels expressed in mammalian cells", *Br J Pharmacol* 132(2): 381-384 (2001); Rundfeldt, C & Netzer, R, "The novel anticonvulsant retigabine activates M-currents in Chinese hamster ovary-cells tranfected with human KCNQ2/3 subunits", *Neurosci Lett* 282(1-2): 73-76 (2000); Main, M J, et al., "Modulation of KCNQ2/3 potassium channels by the novel anticonvulsant retigabine", *Mol Pharmacol* 58(2): 253-262 (2000), each of which is incorporated herein by reference in its entirety]. The result is an inhibition of bladder smooth muscle contractility. In addition, recent data provides evidence for the existence of the KCNQ4 channel in human bladder smooth muscle. Current knowledge of KCNQ4 suggests that it may form a functional ion channel on its own [Sogaard, R, et al., "KCNQ4 channels expressed in mammalian cells: functional characteristics and pharmacology", *Am J Physiol Cell Physiol* 280(4): C859-C866 (2001), which is incorporated herein by reference in its entirety], or that it may combine with KCNQ3 [Kubisch C, et al., "KCNQ4, a novel potassium channel expressed in sensory outer hair cells, is mutated in dominant deafness", *Cell* 96(3):437-446 (1999), which is incorporated herein by reference in its entirety]. It is likely therefore, that retigabine's effects on bladder smooth muscle include activation of the KCNQ4 channel in addition to the channels formed by KCNQ2/3 and KCNQ3/5. Activation of this channel will hyperpolarize the bladder smooth muscle cells and, in doing so, relax the bladder. Since these KCNQ channels are not present in the cardiovascular system, retigabine and other molecules that activate these channels should be useful in the treatment of bladder instability without hemodynamic compromise.

M-currents have been shown to play an important functional role as determinants of cell excitability. Recent evidence indicates that the KCNQ potassium channel subunit form the molecular basis for M-current activity in a variety of tissues. From their initial report in peripheral sympathetic neurons the gene family has evolved to contain at least five major sub-units designated KCNQ1 though KCNQ5 [Rogowski, M A, "KCNQ2/KCNQ3 K+ channels and the molecular pathogenesis of epilepsy: implications for therapy", *Trends Neurosci*23: 393-398, (2000); Jentsch, T J, "Neuronal KCNQ potassium channels: physiology and role in disease", *Nat Rev Neurosci* 1(1):21-30 (2000), each of which is incorporated herein by reference in its entirety]. These sub-units have been shown to co-assemble to form both heteromeric and homomeric functional ion channels. Recent reports indicate that both KCNQ2 and KCNQ5 can co-assemble with KCNQ3 [Tinel, N, et al., "The KCNQ2 potassium channel: splice variants, functional and developmental expression. Brain localization and comparison with KCNQ3", *FEBS Lett* 438(3): 171-176 (1998); Yang, W P, et al., "Functional expression of two KvLQT1-related potassium channels responsible for an inherited idiopathic epilepsy", *J Biol Chem* 273(31):19419-19423 (1998); Wang, H S, et al., "KCNQ2 and KCNQ3 potassium channel subunits: molecular correlets of the M-channel", *Science* 282(5395): 1890-1893 (1998); Lerche, C, et al., "Molecular cloning and functional expression of KCNQ5, a potassium channel subunit that may contribute to neuronal M-current diversity", *J Biol Chem* 275(29): 22395-22400 (2000); Schroeder, B C, et al., "KCNQ5, a novel potassium channel broadly expressed in brain, mediates M-type currents," *J Biol Chem* 275(31): 24089-24095 (2000), each of which is incorporated herein by reference in its entirety] to form a functional M-channel activatable by retigabine [Wickenden, supra, *Molec Pharmacol* 58: 591-600 (2000); Wickenden, supra, *Br J Pharmacol* 132 (2): 381-384 (2001); Rundfeldt & Netzer, supra, *Neurosci Lett* 282(1-2): 73-76 (2000); Main, supra, *Mol Pharmacol* 58(2): 253-262 (2000)] and blocked by either acetylcholine [Adams, P R, et al., "M-currents and other potassium currents in bullfrog sympathetic neurones", *J Physiol* 330: 537-72 (1982); Brown, D A & Adams, P R "Muscarinic suppression of a novel voltage-sensitive K+current in a vertebrate neurone", *Nature* 283: 673-676 (1980); Shapiro, M S, et al., "Reconstitution of muscarinic modulation of the KCNQ2/KCNQ3 K(+) channels that underlie the neuronal M current", *J Neurosci* 20(5): 1710-1721 (2000), each of which is incorporated herein by reference in its entirety], linopirdine, or XE-991 (10,10-bis(4-pyridinylmethyl)-9(10H)-anthra-cenone) [Aiken, S P, et al., "Reduction of spike frequency adaptation and blockade of M-current in rat CA1 pyramidal neurons by linopirdine (DuP 996) a neurotransmitter release enhancer", *Br J Pharmacol* 115(7): 1163-1168, (1995); Zaczek R, "Two new potent neurotransmitter release enhancers, 10,10-bis(4-pyridinylmethyl)-9(10H)-anthracenone and 10,10-bis(2-fluoro-4-pyridinylmethyl)-9(10H)-anthracenone: comparison to linopirdine", *J Pharmacol Exp Ther* 285(2): 724-730 (1998), each of which is incorporated herein by reference in its entirety]. The parasympathetic neurotransmitter acetylcholine (Ach) is known to produce several physiological responses in bladder smooth muscle. The net result of Ach exposure is a contraction of the smooth muscle mainly through the mobilization of transmembrane and intracellular calcium stores [Hashitani H, et al., "Mechanisms of excitatory neuromuscular transmission in the guinea-pig urinary bladder", *J Physiol* 524(Part 2): 565-579 (2000), which is incorporated herein by reference in its entirety]. The role that Ach plays in modulating the cell transmembrane potential, however, is more complex. Pathways for both hyperpolarization and depolarization are present with muscarinic stimulation of bladder smooth muscle. Hyperpolarization may be associated with a mechanism that involves calcium sparks and activation of calcium-dependent potassium currents [Herrera G M, et al., "Voltage dependence of the coupling of Ca(2+) sparks to BK(Ca) channels in urinary bladder smooth muscle", *Am J Physiol Cell Physiol* 280(3): C481-490 (2001), which is incorporated herein by reference in its entirety].

Given their potential in the treatment of urinary incontinence and other disorders, there is an interest in developing new potassium channel modulators. This invention addresses these needs and others.

SUMMARY OF THE INVENTION

In one aspect, the present invention provides compounds of Formula I:

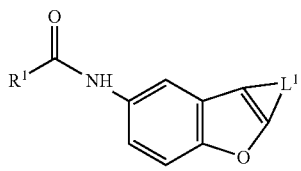

I or pharmaceutically acceptable salts thereof, wherein:

$R^1$ is H, $C_{1-12}$ alkyl, $C_{2-12}$ alkenyl, $C_{2-12}$ alkynyl, $C_{1-12}$ haloalkyl, $C_{1-12}$ haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, heteroarylalkynyl, heteroaryl, heteroarylalkyl, heteroarylalkenyl, heteroarylalkynyl, —$OR^2$, —$SR^2$, or —$NR^3R^4$; wherein said $C_{1-12}$ alkyl, $C_{2-12}$ alkenyl, $C_{2-12}$ alkynyl, $C_{2-12}$ haloalkyl, $C_{1-12}$ haloalkoxy, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, heteroarylalkynyl, heteroaryl, heteroarylalkyl, heteroarylalkenyl, and heteroarylalkynyl are each optionally substituted with 1, 2, 3, or 4 independently selected $R^5$ groups;

$L^1$ is a $C_{3-6}$ alkylene bridge, which is optionally substituted with 1, 2, or 3 groups independently selected from $OR^o$, $SR^o$, $C(O)R^p$, $C(O)NR^sR^t$, $C(O)OR^p$, $OC(O)R^p$, $OC(O)NR^sR^t$, $NR^qC(O)R^r$, $NR^qC(O)OR^r$, $NR^qC(O)NR^r$, $S(O)R^p$, $S(O)NR^sR^t$, $S(O)_2R^p$, $NR^qS(O)_2R^r$, $NR^pS(O)_2NR^sR^t$, oxo, halogen, cyano, nitro, hydroxyl, $C_{1-6}$ alkyl, $C_{1-6}$ alkenyl, $C_{1-6}$ alkynyl, $C_{1-6}$ haloalkyl, $C_{1-6}$ haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, and heteroarylalkynyl; wherein said $C_{1-6}$ alkyl, $C_{1-6}$ alkenyl, $C_{1-6}$ alkynyl, $C_{1-6}$ haloalkyl, $C_{1-6}$ haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, and heteroarylalkynyl are each optionally substituted with 1, 2, or 3 independently selected $R^6$ groups;

each $R^2$, $R^3$, and $R^4$ is, independently, H, $C_{1-6}$alkyl, $C_{1-6}$alkenyl, $C_{1-6}$ alkynyl, $C_{1-6}$ haloalkyl, cycloalkyl, cycloalkylalkyl, heterocycloalkyl, heterocycloalkylalkyl, aryl, arylalkyl, heteroaryl, or heteroarylalkyl; wherein said $C_{1-6}$ alkyl, $C_{1-6}$ alkenyl, $C_{1-6}$ alkynyl, $C_{1-6}$ haloalkyl, cycloalkyl, cycloalkylalkyl, heterocycloalkyl, heterocycloalkylalkyl, aryl, arylalkyl, heteroaryl, and heteroarylalkyl are each optionally substituted with 1, 2, 3, or 4 independently selected $R^7$ groups;

each $R^5$ and $R^7$ is, independently, $OR^a$, $SR^a$, $C(O)R^b$, $C(O)NR^eR^f$, $C(O)OR^b$, $OC(O)R^b$, $OC(O)NR^eR^f$, $NR^eR^f$, $NR^cC(O)R^d$, $NR^cC(O)OR^d$, $NR^cC(O)NR^d$, $S(O)R^b$, $S(O)NR^eR^f$, $S(O)_2R^b$, $NR^cS(O)_2R^d$, $NR^bS(O)_2NR^eR^f$, $C(=NR^a)R^b$, $C(=NR^a)NR^b$, $C(=NR^a)OR^b$, $OC(=NR^a)R^b$, $OC(=NR^a)NR^b$, $NR^cC(=NR^a)R^d$, $NR^cC(=NR^a)OR^d$, $NR^cC(=NR^a)NR^d$, halogen, cyano, nitro, $C_{1-6}$ alkyl, $C_{1-6}$ alkenyl, $C_{1-6}$ alkynyl, $C_{1-6}$ haloalkyl, $C_{1-6}$ haloalkoxy, cycloalkyl, cycloalkylalkyl, heterocycloalkyl, heterocycloalkylalkyl, aryl, arylalkyl, heteroaryl, or heteroarylalkyl; wherein said $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, heterocycloalkyl, heterocycloalkylalkyl, aryl, arylalkyl, heteroaryl, and heteroarylalkyl are each optionally substituted with 1, 2, 3, or 4 independently selected $R^8$ groups;

each $R^6$ is, independently, halogen, cyano, nitro, hydroxyl, amino, $C_{1-6}$ alkyl, $C_{1-6}$ haloalkyl, $C_{1-6}$ alkoxy, $C_{1-6}$ haloalkoxy, alkylamino, dialkylamino, acyl, formyl, carbamyl, alkylcarbamyl, dialkylcarbamyl, alkylcarbamyloxy, dialkylcarbamyloxy, acyloxy, alkyloxycarbonyl, carboxy, alkylsulfonyl, alkylsulfinyl, alkylthio, cycloalkyl, cycloalkylalkyl, heterocycloalkyl, heterocycloalkylalkyl, aryl, arylalkyl, heteroaryl, or heteroarylalkyl;

each $R^8$ is, independently, $OR^a$, $SR^a$, $C(O)R^b$, $C(O)NR^eR^f$, $C(O)OR^b$, $OC(O)R^b$, $OC(O)NR^eR^f$, $NR^eR^f$, $NR^cC(O)R^d$, $NR^cC(O)OR^d$, $NR^cC(O)NR^d$, $S(O)R^b$, $S(O)NR^eR^f$, $S(O)_2R^b$, $NR^cS(O)_2R^d$, $NR^bS(O)_2NR^eR^r$, halogen, cyano, nitro, hydroxyl, carboxy, $C_{1-6}$alkyl, $C_{1-6}$alkenyl, $C_{1-6}$alkynyl, $C_{1-6}$haloalkyl, $C_{1-6}$alkoxy, $C_{1-6}$haloalkoxy, cycloalkyl, cycloalkylalkyl, cycloalkyloxy, cycloalkylkyloxy, heterocycloalkyl, heterocycloalkylalkyl, heterocycloalkyloxy, heterocycloalkylalkyloxy, aryl, arylalkyl, aryloxy, arylalkyloxy, heteroaryl, heteroarylalkyl, heteroaryloxy, heteroarylalkyloxy, amino, alkylamino, dialkylamino, acyl, formyl, carbamyl, alkylcarbamyl, dialkylcarbamyl, alkylcarbamyloxy, dialkylcarbamyloxy, acyloxy, alkyloxycarbonyl, carboxy, alkylsulfonyl, alkylsulfinyl, or alkylthio;

each $R^a$, $R^b$, $R^c$, $R^d$, $R^e$, and $R^f$ is, independently, H, $C_{1-6}$ alkyl, $C_{1-6}$ haloalkyl, $C_{2-6}$ alkenyl, $C_{2-6}$ alkynyl, cycloalkyl, cycloalkylalkyl, heterocycloalkyl, heterocycloalkylalkyl, aryl, arylalkyl, heteroaryl, or heteroarylalkyl; wherein said $C_{1-6}$ alkyl, $C_{1-6}$ haloalkyl, $C_{2-6}$ alkenyl, $C_{2-6}$ alkynyl, cycloalkyl, cycloalkylalkyl, heterocycloalkyl, heterocycloalkylalkyl, aryl, arylalkyl, heteroaryl, and heteroarylalkyl are each optionally substituted with 1, 2, or 3 independently selected $R^g$ groups;

or any $R^c$ and $R^d$, together with the moiety to which they are attached, can form a 3-, 4-, 5-, 6- 7- or 8-membered heterocycloalkyl ring, wherein said heterocycloalkyl ring is optionally substituted with 1, 2, or 3 independently selected $R^g$ groups;

or any $R^e$ and $R^f$, together with the nitrogen atom to which they are attached, can form a 3-, 4-, 5-, 6- 7- or 8-membered heterocycloalkyl ring or 5-, 6-, 7- or 8-membered heteroaryl ring, wherein said heterocycloalkyl or heteroaryl ring is optionally substituted with 1, 2, or 3 independently selected $R^{g''}$ groups;

each $R^g$ is, independently, $OR^u$, $SR^u$, $C(O)R^v$, $C(O)NR^yR^z$, $C(O)OR^v$, $OC(O)R^v$, $OC(O)NR^yR^z$, $NR^yR^z$, $NR^wC(O)R^x$, $NR^wC(O)OR^x$, $NR^wC(O)NR^x$, halogen, cyano, nitro, $C_{1-6}$ alkyl, $C_{1-6}$ haloalkyl, $C_{1-6}$ haloalkoxy, cycloalkyl, cycloalkylalkyl, heterocycloalkyl, heterocycloalkylalkyl, aryl, arylalkyl, heteroaryl, or heteroarylalkyl;

each $R^{g'}$ and $R^{g''}$ is, independently, halogen, cyano, nitro, hydroxyl, $C_{1-6}$ alkyl, $C_{1-6}$ haloalkyl, $C_{1-6}$ alkoxy, $C_{1-6}$ haloalkoxy, cycloalkyl, cycloalkylalkyl, heterocycloalkyl, heterocycloalkylalkyl, aryl, arylalkyl, heteroaryl, heteroarylalkyl, amino, alkylamino, dialkylamino, acyl, formyl, carbamyl, alkylcarbamyl, dialkylcarbamyl, alkylcarbamyloxy, dialkylcarbamyloxy, acyloxy, carboxy, alkylsulfonyl, or alkylsulfinyl;

each $R^o$, $R^p$, $R^q$, $R^r$, $R^s$, and $R^t$ is, independently, H, $C_{1-6}$ alkyl, $C_{1-6}$ haloalkyl, $C_{2-6}$ alkenyl, $C_{2-6}$ alkynyl, cycloalkyl, cycloalkylalkyl, heterocycloalkyl, heterocycloalkylalkyl, aryl, arylalkyl, heteroaryl, or heteroarylalkyl; wherein said $C_{1-6}$ alkyl, $C_{1-6}$ haloalkyl, $C_{2-6}$ alkenyl, $C_{2-6}$ alkynyl, cycloalkyl, cycloalkylalkyl, heterocycloalkyl, heterocycloalkylalkyl, aryl, arylalkyl, heteroaryl, and heteroarylalkyl are each optionally substituted with 1, 2, or 3 groups independently selected from halogen, cyano, nitro, $C_{1-6}$alkyl, $C_{1-6}$haloalkyl, amino, alkylamino, dialkylamino, acyl, formyl, acyloxy, carbamyl, alkylcarbamyl, dialkylcarbamyl, alkylcarbamyloxy, and dialkylcarbamyloxy;

or any $R^q$ and $R^r$, together with the moiety to which they are attached, can form a 3-, 4-, 5-, 6- 7- or 8-membered heterocycloalkyl ring;

or any $R^s$ and $R^t$, together with the nitrogen atom to which they are attached, can form a 3-, 4-, 5-, 6- 7- or 8-membered heterocycloalkyl ring or 5-, 6-, 7- or 8-membered heteroaryl ring;

each $R^{a'}$, $R^{b'}$, $R^{c'}$, $R^{d'}$, $R^{e'}$, and $R^{f'}$ is, independently, H, $C_{1-6}$alkyl, $C_{1-6}$ haloalkyl, cycloalkyl, cycloalkylalkyl, heterocycloalkyl, heterocycloalkylalkyl, aryl, arylalkyl, heteroaryl, or heteroarylalkyl;

or any $R^{c'}$ and $R^{d'}$, together with the moiety to which they are attached, can form a 3-, 4-, 5-, 6-7- or 8-membered heterocycloalkyl ring;

or any $R^{e'}$ and $R^{f'}$, together with the nitrogen atom to which they are attached, can form a 3-, 4-, 5-, 6-7- or 8-membered heterocycloalkyl ring or 5-, 6-, 7- or 8-membered heteroaryl ring; and each $R^u$, $R^v$, $R^w$, $R^x$, $R^y$, and $R^z$ is, independently, H, $C_{1-6}$ alkyl, $C_{1-6}$ haloalkyl, cycloalkyl, cycloalkylalkyl, heterocycloalkyl, heterocycloalkylalkyl, aryl, arylalkyl, heteroaryl, or heteroarylalkyl; provided that the compound is not selected from:

N-(6,7,8,9-tetrahydrodibenzofuran-2-yl)-9H-xanthene-9-acetamide;

2-[(phenylmethylthio)]-N-(6,7,8,9-tetrahydrodibenzofuran-2-yl)-acetamide;

4-oxo-4-[(6,7,8,9-tetrahydro-2-dibenzofuranyl)amino]-butanoic acid methyl ester;

2,2-dimethyl-N,N'-bis(6,7,8,9-tetrahydro-2-dibenzofuranyl)-propanediamide;

3-chloro-N-(6,7,8,9-tetrahydro-2-dibenzofuranyl)benzo[b]thiophene-2-carboxamide;

2-methoxy-4-(methylthio)-N-(6,7,8,9-tetrahydro-2-dibenzofuranyl)-benzamide;

N-(6,7,8,9-tetrahydro-2-dibenzofuranyl)-cyclohexanecarboxamide;

N-(6,7,8,9-tetrahydro-2-dibenzofuranyl)-cyclopentanecarboxamide;

N-(6,7,8,9-tetrahydro-2-dibenzofuranyl)-3-(trifluoromethyl)-benzamide;

N-(6,7,8,9-tetrahydro-2-dibenzofuranyl)-4-(trifluoromethyl)-benzamide;

1-adamantan-1-yl-3-(6,7,8,9-tetrahydro-dibenzofuran-2-yl)-urea;

N-(3-chlorophenyl)-N'-(6,7,8,9-tetrahydro-2-dibenzofuranyl)-urea;

N-(6,7,8,9-tetrahydro-2-dibenzofuranyl)-1,3-benzodioxole-5-carboxamide;

4-(4-morpholinylsulfonyl)-N-(6,7,8,9-tetrahydro-2-dibenzofuranyl)-benzamide;

8-acetamido-a-methyl-1,2,3,4-tetrahydro-3-dibenzofuranacetic acid ethyl ester;

4-(dimethylaminosulfonylamino)-(7,8,9,10-tetrahydro-6H-benzo[b]cyclohepta[d]furan-2-yl)cyclohexanecarboxamide; and 4-(1-pyrrolidinylsulfonyl)- N-(6,7,8,9-tetrahydro-2-dibenzofuranyl)-benzamide;

or pharmaceutically acceptable salt thereof.

In another aspect, the present invention provides pharmaceutical compositions which comprises a compound of Formula I, or a pharmaceutically salt thereof, and a pharmaceutically acceptable carrier.

In yet another aspect, the present invention provides methods of treating ischemic heart disease, myocardial infarction, cardiac arrhythmia, hypertension, or angina pectoris in an individual in need thereof, comprising administering to said individual a therapeutically effective amount of a compound of Formula I.

The present invention further provides methods of treating epilepsy, episodic ataxia type 1, paroxysmal dyskinesia, neurodegenerative spincerebrallar ataxia, Parkinson's disease, Alzheimer's disease, or multiple sclerosis in an individual in need of treatment thereof, comprising administering to said individual a therapeutically effective amount of a compound of Formula I.

The present invention further provides methods of treating depression, generalized anxiety disorder, bulimia nervosa, or anorexia nervosa in an individual in need thereof, comprising administering to said individual a therapeutically effective amount of a compound of Formula I.

The present invention further provides methods of treating type I diabetes or type II diabetes in an individual in need thereof, comprising administering to said individual a therapeutically effective amount of a compound of Formula I.

The present invention further provides methods of treating allergy or asthma in an individual in need thereof, comprising administering to said individual a therapeutically effective amount of a compound of Formula I.

The present invention further provides methods of treating urinary incontinence, irritable bowel syndrome, or irritable bladder syndrome in an individual in need thereof, comprising administering to said individual a therapeutically effective amount of a compound of Formula I.

The present invention further provides methods of treating pain or inflammation in an individual in need thereof, comprising administering to said individual a therapeutically effective amount of a compound of Formula I.

The present invention further provides methods of modulating a potassium channel in an individual in need thereof, comprising administering to said individual a therapeutically effective amount of a compound of Formula I.

The present invention further provides methods of modulating a potassium channel in an individual in need thereof, comprising administering to said individual a therapeutically effective amount of a compound of Formula I.

In another aspect, the present invention further provides uses of a compound of Formula I, or pharmaceutically acceptable salt thereof, for the production of medicament for use in the treatment of disorders remedied or alleviated by potassium channel modulation.

The present invention further provides uses of a compound of Formula I, or pharmaceutically acceptable salt thereof, for the production of medicament for use in the treatment of ischemic heart disease, myocardial infarction, cardiac arrhythmia, hypertension, or angina pectoris.

The present invention further provides uses of a compound of Formula I, or pharmaceutically acceptable salt thereof, for the production of medicament for use in the treatment of epilepsy, episodic ataxia type 1, paroxysmal dyskinesia, neurodegenerative spincerebrallar ataxia, Parkinson's disease, Alzheimer's disease, or multiple sclerosis.

The present invention further provides uses of a compound of Formula I, or pharmaceutically acceptable salt thereof, for the production of medicament for use in the treatment of depression, generalized anxiety disorder, bulimia nervosa, or anorexia nervosa, The present invention further provides uses of a compound of Formula I, or pharmaceutically acceptable salt thereof, for the production of medicament for use in the treatment of type I diabetes or type II diabetes.

The present invention further provides uses of a compound of Formula I, or pharmaceutically acceptable salt thereof, for the production of medicament for use in the treatment of allergy or asthma.

The present invention further provides uses of a compound of Formula I, or pharmaceutically acceptable salt thereof, for the production of medicament for use in the treatment of urinary incontinence, irritable bowel syndrome, or irritable bladder syndrome.

The present invention further provides uses of a compound of Formula I, or pharmaceutically acceptable salt thereof, for the production of medicament for use in the treatment of pain or inflammation.

In another aspect, the present invention provides compounds of Formula I, or pharmaceutically acceptable salts thereof, for use in a method of treatment of disorders remedied or alleviated by potassium channel modulation.

The present invention further provides compounds of Formula I, or pharmaceutically acceptable salts thereof, for use in a method of treatment of ischemic heart disease, myocardial infarction, cardiac arrhythmia, hypertension, or angina pectoris by therapy.

The present invention further provides compounds of Formula I, or pharmaceutically acceptable salts thereof, for use in a method of treatment of epilepsy, episodic ataxia type 1, paroxysmal dyskinesia, neurodegenerative spincerebrallar ataxia, Parkinson's disease, Alzheimer's disease, or multiple sclerosis by therapy.

The present invention further provides compounds of Formula I, or pharmaceutically acceptable salts thereof, for use in a method of treatment of depression, generalized anxiety disorder, bulimia nervosa, or anorexia nervosa by therapy.

The present invention further provides compounds of Formula I, or pharmaceutically acceptable salts thereof, for use in a method of treatment of type I diabetes or type II diabetes by therapy.

The present invention further provides compounds of Formula I, or pharmaceutically acceptable salts thereof, for use in a method of treatment of allergy or asthma by therapy.

The present invention further provides compounds of Formula I, or pharmaceutically acceptable salts thereof, for use in a method of treatment of urinary incontinence, irritable bowel syndrome, or irritable bladder syndrome by therapy.

The present invention further provides compounds of Formula I, or pharmaceutically acceptable salts thereof, for use in a method of treatment of pain or inflammation by therapy.

In another aspect, the present invention provides synthetic processes for producing a compound of Formula I comprising reacting a compound of Formula VI:

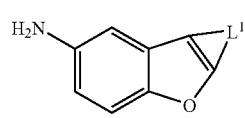

with a compound of Formula VII:

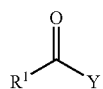

under conditions and for a time sufficient to produce a compound of Formula I;

wherein:

Y is halogen, $C_{1-12}$alkoxy, hydroxyl, amino, $OC(O)R^{yy}$, or $OC(O)R_1$; and $R^{yy}$ is $C_{1-12}$ alkyl.

The present invention further provides synthetic processes for producing a compound of Formula VI that comprise reducing the nitro group of a compound of Formula V:

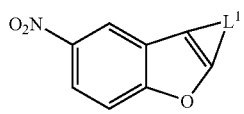
V under conditions and for a time sufficient to produce a compound of Formula VI.

The present invention further provides synthetic processes for producing a compound of Formula V that comprise:

a) reacting a compound of Formula II:

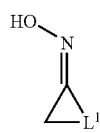
II with a base to under conditions and for a time sufficient to form the alkoxide of the compound of Formula II;

b) treating said alkoxide of the compound of Formula II with a compound of Formula III:

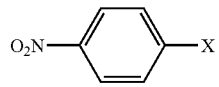
III under conditions and for a time sufficient to form a compound of Formula IV:

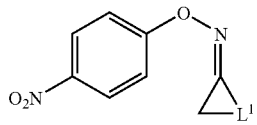
IV and c) treating the compound of Formula IV with an acid under conditions and for a time sufficient to produce a compound of Formula V;

wherein X is halogen.

The present invention further provides synthetic processes for producing a compound of Formula VI that comprise reacting a compound of Formula XII:

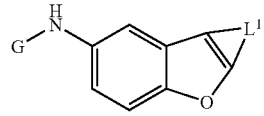
XII under conditions and for a time sufficient to form a compound of Formula VI;

wherein G is a protecting group.

The present invention further provides synthetic processes for producing a compound of Formula XII that comprises:

a) reacting a compound of Formula IX:

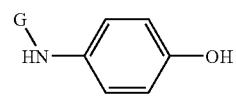
IX with an oxidizing agent under conditions and for a time sufficient to produce a compound of Formula X:

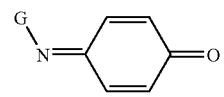
X and b) reacting said compound of Formula X with a compound of Formula XIII:

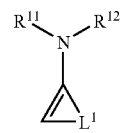
XIII under conditions and for a time sufficient to produce a compound of Formula XII;

wherein:

$R^{11}$ and $R^{12}$ are each, independently, $C_{1-6}$ alkyl, cycloalkyl, cycloalkylalkyl, heterocycloalkylalkyl, aryl, arylalkyl, heteroaryl, or heteroarylalkyl; and G is a protecting group.

The present invention further provides synthetic processes for producing a compound of Formula VI that comprise reacting a compound of Formula XIIa:

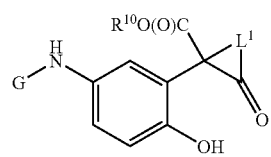
XIIa under conditions and for a time sufficient to form a compound of Formula VI;

wherein G is a protecting group.

The present invention further provides synthetic processes for producing a compound of Formula XIIa that comprise:

a) reacting a compound of Formula IX:

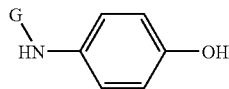

IX with an oxidizing agent under conditions and for a time sufficient to produce a compound of Formula X:

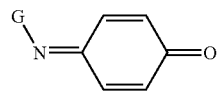

X b) reacting a compound of Formula XI:

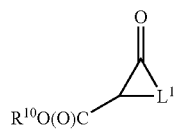

XI with a base;

c) reacting the compound of Formula X with the reaction mixture of b); under conditions and for a time sufficient to produce a compound of Formula XIIa;

wherein:

$R^{10}$ is $C_{1-6}$ alkyl, cycloalkyl, cycloalkylalkyl, heterocycloalkylalkyl, aryl, arylalkyl, heteroaryl, or heteroarylalkyl; and G is a protecting group.

The present invention further provides synthetic processes for producing a compound of Formula I comprising reacting a compound of Formula XIV:

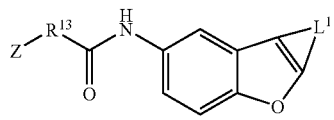

XIV with a compound of formula H—$NR^eR^f$ under conditions and for a time sufficient to produce a compound of Formula I;

wherein:

$R^1$ is $C_{1-12}$ alkyl substituted with 1 $R^5$ group;

$R^5$ is $NR^eR^f$;

$R^{13}$ is $C_{1-12}$alkylene; and

Z is halogen.

The present invention further provides synthetic processes for producing a compound of Formula I comprising reacting a compound of Formula XIV:

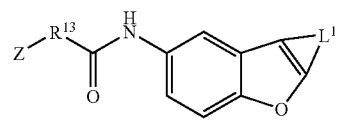

XIV with a compound of formula H—$OR^a$ under conditions and for a time sufficient to produce a compound of Formula I;

wherein:

$R^1$ is $C_{1-12}$ alkyl substituted with 1 $R^5$ group;

$R^5$ is $OR^a$;

$R^{13}$ is $C_{1-12}$alkylene; and

Z is halogen.

DETAILED DESCRIPTION OF THE INVENTION

The present invention provides a compound of Formula I:

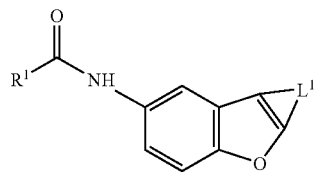

I or pharmaceutically acceptable salt thereof, wherein:

$R^1$ is H, $C_{1-12}$ alkyl, $C_{2-12}$ alkenyl, $C_{2-12}$ alkynyl, $C_{1-12}$ haloalkyl, $C_{1-12}$ haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, heteroarylalkynyl, heteroaryl, heteroarylalkyl, heteroarylalkenyl, heteroarylalkynyl, —$OR^2$, —$SR^2$, or —$NR^3R^4$; wherein said $C_{1-12}$ alkyl, $C_{2-12}$alkenyl, $C_{2-12}$ alkynyl, $C_{1-12}$ haloalkyl, $C_{1-12}$ haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, heteroarylalkynyl, heteroaryl, heteroarylalkyl, heteroarylalkenyl, and heteroarylalkynyl are each optionally substituted with 1, 2, 3, or 4 independently selected $R^5$ groups;

$L^1$ is a $C_{3-6}$ alkylene bridge, which is optionally substituted with 1, 2, or 3 groups independently selected from $OR^o$, $SR^o$, $C(O)R^p$, $C(O)NR^sR^t$, $C(O)OR^p$, $OC(O)R^p$, $OC(O)NR^sR^t$, $NR^qC(O)R^r$, $NR^qC(O)OR^r$, $NR^qC(O)NR^r$, $S(O)R^p$, $S(O)N R^sR^t$, $S(O)_2R^p$, $NR^qS(O)_2R^r$, $NR^pS(O)_2 NR^sR^t$, oxo, halogen, cyano, nitro, hydroxyl, $C_{1-6}$alkyl, $C_{1-6}$ alkenyl, $C_{1-6}$ alkynyl, $C_{1-6}$ haloalkyl, $C_{1-6}$ haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, and heteroarylalkynyl; wherein said $C_{1-6}$ alkyl, $C_{1-6}$ alkenyl, $C_{1-6}$ alkynyl, $C_{1-6}$ haloalkyl, $C_{1-6}$ haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, and heteroarylalkynyl are each optionally substituted with 1, 2, or 3 independently selected $R^6$ groups;

each $R^2$, $R^3$, and $R^4$ is, independently, H, $C_{1-6}$alkyl, $C_{1-6}$alkenyl, $C_{1-6}$alkynyl, $C_{1-6}$ haloalkyl, cycloalkyl, cycloalkylalkyl, heterocycloalkyl, heterocycloalkylalkyl, aryl, arylalkyl, heteroaryl, or heteroarylalkyl; wherein said $C_{1-6}$ alkyl, $C_{1-6}$ alkenyl, $C_{1-6}$ alkynyl, $C_{1-6}$ haloalkyl, cycloalkyl, cycloalkylalkyl, heterocycloalkyl, heterocycloalkylalkyl, aryl, arylalkyl, heteroaryl, and heteroarylalkyl are each optionally substituted with 1, 2, 3, or 4 independently selected $R^7$ groups;

each $R^5$ and $R^7$ is, independently, $OR^a$, $SR^a$, $C(O)R^b$, $C(O)NR^eR^f$, $C(O)OR^b$, $OC(O)R^b$, $OC(O)NR^eR^f$, $NR^eR^f$, $NR^cC(O)R^d$, $NR^cC(O)OR^d$, $NR^cC(O)NR^d$, $S(O)R^b$, $S(O)NR^eR^f$, $S(O)_2R^b$, $NR^cS(O)_2R^d$, $NR^bS(O)_2NR^eR^f$, $C(=NR^a)R^b$, $C(=NR^a)NR^b$, $C(=NR^a)OR^b$, $OC(=NR^a)R^b$, $OC(=NR^a)NR^b$, $NR^cC(=NR^a)R^d$, $NR^cC(=NR^a)Or^d$, $NR^cC(=NR^a)NR^d$, halogen, cyano, nitro, $C_{1-6}$ alkyl, $C_{1-6}$ alkenyl, $C_{1-6}$ alkynyl, $C_{1-6}$ haloalkyl, $C_{1-6}$ haloalkoxy, cycloalkyl, cycloalkylalkyl, heterocycloalkyl, heterocycloalkylalkyl, aryl, arylalkyl, heteroaryl, or heteroarylalkyl; wherein said $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, cycloalkyl, cycloalkylalkyl, heterocycloalkyl, heterocycloalkylalkyl, aryl, arylalkyl, heteroaryl, and heteroarylalkyl are each optionally substituted with 1, 2, 3, or 4 independently selected $R^8$ groups;

each $R^6$ is, independently, halogen, cyano, nitro, hydroxyl, amino, $C_{1-6}$ alkyl, $C_{1-6}$ haloalkyl, $C_{1-6}$ alkoxy, $C_{1-6}$ haloalkoxy, alkylamino, dialkylamino, acyl, formyl, carbamyl, alkylcarbamyl, dialkylcarbamyl, alkylcarbamyloxy, dialkylcarbamyloxy, acyloxy, alkyloxycarbonyl, carboxy, alkylsulfonyl, alkylsulfinyl, alkylthio, cycloalkyl, cycloalkylalkyl, heterocycloalkyl, heterocycloalkylalkyl, aryl, arylalkyl, heteroaryl, or heteroarylalkyl;

each $R^8$ is, independently, $OR^{a'}$, $SR^{a'}$, $C(O)R^{b'}$, $C(O)NR^{e'}R^{f'}$, $C(O)OR^{b'}$, $OC(O)R^{b'}$, $OC(O)NR^{e'}R^{f'}$, $NR^{e'}R^{f'}$, $NR^{c'}C(O)R^{d'}$, $NR^{c'}C(O)OR^{d'}$, $NR^{c'}C(O)N$ $R^{d'}$, $S(O)R^{b'}$, $S(O)NR^{e'}R^{f'}$, $S(O)_2R^{b'}$, $NR^{c'}S(O)_2R^{d'}$, $NR^bS(O)_2NR^{e'}R^{f'}$, halogen, cyano, nitro, hydroxyl, carboxy, $C_{1-6}$alkyl, $C_{1-6}$alkenyl, $C_{1-6}$alkynyl, $C_{1-6}$haloalkyl, $C_{1-6}$alkoxy, $C_{1-6}$haloalkoxy, cycloalkyl, cycloalkylalkyl, cycloalkyloxy, cycloalkylalkyloxy, heterocycloalkyl, heterocycloalkylalkyl, heterocycloalkyloxy, heterocycloalkylalkyloxy, aryl, arylalkyl, aryloxy, arylalkyloxy, heteroaryl, heteroarylalkyl, heteroaryloxy, heteroarylalkyloxy, amino, alkylamino, dialkylamino, acyl, formyl, carbamyl, alkylcarbamyl, dialkylcarbamyl, alkylcarbamyloxy, dialkylcarbamyloxy, acyloxy, alkyloxycarbonyl, carboxy, alkylsulfonyl, alkylsulfinyl, or alkylthio;

each $R^a$, $R^b$, $R^c$, $R^d$, $R^e$, and $R^f$ is, independently, H, $C_{1-6}$alkyl, $C_{1-6}$haloalkyl, $C_{2-6}$ alkenyl, $C_{2-6}$ alkynyl, cycloalkyl, cycloalkylalkyl, heterocycloalkyl, heterocycloalkylalkyl, aryl, arylalkyl, heteroaryl, or heteroarylalkyl; wherein said $C_{1-6}$ alkyl, $C_{1-6}$ haloalkyl, $C_{2-6}$ alkenyl, $C_{2-6}$ alkynyl, cycloalkyl, cycloalkylalkyl, heterocycloalkyl, heterocycloalkylalkyl, aryl, arylalkyl, heteroaryl, and heteroarylalkyl are each optionally substituted with 1, 2, or 3 independently selected $R^g$ groups;

or any $R^c$ and $R^d$, together with the moiety to which they are attached, can form a 3-, 4-, 5-, 6-7- or 8-membered heterocloalkyl ring, wherein said heterocycloalkyl ring is optionally substituted with 1, 2, or 3 independently selected $R^{g'}$ groups;

or any $R^e$ and $R^f$, together with the nitrogen atom to which they are attached, can form a 3-, 4-, 5-, 6-7- or 8-membered heterocycloalkyl ring or 5-, 6-, 7- or 8- membered heteroaryl ring, wherein said heterocycloalkyl or heteroaryl ring is optionally substituted with 1, 2, or 3 independently selected $R^g$ groups;

each $R^g$ is, independently, $OR^u$, $SR^u$, $C(O)R^v$, $C(O)NR^yR^z$, $C(O)OR^v$, $OC(O)R^v$, $OC(O)NR^yR^z$, $NR^yR^z$, $NR^wC(O)R^x$, $NR^wC(O)OR^x$, $NR^wC(O)NR^x$, halogen, cyano, nitro, $C_{1-6}$ alkyl, $C_{1-6}$ haloalkyl, $C_{1-6}$ haloalkoxy, cycloalkyl, cycloalkylalkyl, heterocycloalkyl, heterocycloalkylalkyl, aryl, arylalkyl, heteroaryl, or heteroarylalkyl;

each $R^{g'}$ and $R^{g''}$ is, independently, halogen, cyano, nitro, hydroxyl, $C_{1-6}$alkyl, $C_{1-6}$ haloalkyl, $C_{1-6}$ alkoxy, $C_{1-6}$ haloalkoxy, cycloalkyl, cycloalkylalkyl, heterocycloalkyl, heterocycloalkylalkyl, aryl, arylalkyl, heteroaryl, heteroarylalkyl, amino, alkylamino, dialkylamino, acyl, formyl, carbamyl, alkylcarbamyl, dialkylcarbamyl, alkylcarbamyloxy, dialkylcarbamyloxy, acyloxy, carboxy, alkylsulfonyl, or alkylsulfinyl;

each $R^o$, $R^p$, $R^q$, $R^r$, $R^s$, and $R^t$ is, independently, H, $C_{1-6}$ alkyl, $C_{1-6}$ haloalkyl, $C_{2-6}$ alkenyl, $C_{2-6}$ alkynyl, cycloalkyl, cycloalkylalkyl, heterocycloalkyl, heterocycloalkylalkyl, aryl, arylalkyl, heteroaryl, or heteroarylalkyl; wherein said $C_{1-6}$ alkyl, $C_{1-6}$ haloalkyl, $C_{2-6}$ alkenyl, $C_{2-6}$ alkynyl, cycloalkyl, cycloalkylalkyl, heterocycloalkyl, heterocycloalkylalkyl, aryl, arylalkyl, heteroaryl, and heteroarylalkyl are each optionally substituted with 1, 2, or 3 groups independently selected from halogen, cyano, nitro, $C_{1-6}$alkyl, $C_{1-6}$haloalkyl, amino, alkylamino, dialkylamino, acyl, formyl, acyloxy, carbamyl, alkylcarbamyl, dialkylcarbamyl, alkylcarbamyloxy, and dialkylcarbamyloxy;

or any $R^q$ and $R^r$, together with the moiety to which they are attached, can form a 3-, 4-, 5-, 6-7- or 8-membered heterocycloalkyl ring;

or any $R^s$ and $R^t$, together with the nitrogen atom to which they are attached, can form a 3-, 4-, 5-, 6-7- or 8-membered heterocycloalkyl ring or 5-, 6-, 7- or 8-membered heteroaryl ring;

each $R^{a'}$, $R^{b'}$, $R^{c'}$, $R^{d'}$, $R^{e'}$, and $R^{f'}$ is, independently, H, $C_{1-6}$alkyl, $C_{1-6}$ haloalkyl, cycloalkyl, cycloalkylalkyl, heterocycloalkyl, heterocycloalkylalkyl, aryl, arylalkyl, heteroaryl, or heteroarylalkyl;

or any $R^{c'}$ and $R^{d'}$, together with the moiety to which they are attached, can form a 3-, 4-, 5-, 6-7- or 8-membered heterocycloalkyl ring;

or any $R^{e'}$ and $R^{f'}$, together with the nitrogen atom to which they are attached, can form a 3-, 4-, 5-, 6-7- or 8-membered heterocycloalkyl ring or 5-, 6-, 7- or 8-membered heteroaryl ring; and each $R^u$, $R^v$, $R^w$, $R^x$, $R^y$, and $R^z$ is, independently, H, $C_{1-6}$ alkyl, $C_{1-6}$ haloalkyl, cycloalkyl, cycloalkylalkyl, heterocycloalkyl, heterocycloalkylalkyl, aryl, arylalkyl, heteroaryl, or heteroarylalkyl; provided that the compound is not selected from:

N-(6,7,8,9-tetrahydrodibenzofuran-2-yl)-9H-xanthene-9-acetamide;

2-[(phenylmethylthio)]-N-(6,7,8,9-tetrahydrodibenzofuran-2-yl)-acetamide;

4-oxo-4-[(6,7,8,9-tetrahydro-2-dibenzofuranyl)amino]-butanoic acid methyl ester;

2,2-dimethyl-N,N'-bis(6,7,8,9-tetrahydro-2-dibenzofuranyl)-propanediamide;

3-chloro-N-(6,7,8,9-tetrahydro-2-dibenzofuranyl)benzo[b]thiophene-2-carboxamide;

2-methoxy-4-(methylthio)-N-(6,7,8,9-tetrahydro-2-dibenzofuranyl)-benzamide;

N-(6,7,8,9-tetrahydro-2-dibenzofuranyl)-cyclohexanecarboxamide;

N-(6,7,8,9-tetrahydro-2-dibenzofuranyl)-cyclopentanecarboxamide;

N-(6,7,8,9-tetrahydro-2-dibenzofuranyl)-3-(trifluoromethyl)-benzamide;

N-(6,7,8,9-tetrahydro-2-dibenzofuranyl)-4-(trifluoromethyl)-benzamide;

1-adamantan-1-yl-3-(6,7,8,9-tetrahydro-dibenzofuran-2-yl)-urea;

N-(3-chlorophenyl)-N'-(6,7,8,9-tetrahydro-2-dibenzofuranyl)-urea;

N-(6,7,8,9-tetrahydro-2-dibenzofuranyl)-1,3-benzodioxole-5-carboxamide;

4-(4-morpholinylsulfonyl)-N-(6,7,8,9-tetrahydro-2-dibenzofuranyl)-benzamide;

8-acetamido-a-methyl-1,2,3,4-tetrahydro-3-dibenzofuranacetic acid ethyl ester;

4-(dimethylaminosulfonylamino)-(7,8,9,10-tetrahydro-6H-benzo[b]cyclohepta[d]furan-2-yl)cyclohexanecarboxamide; and 4-(1-pyrrolidinylsulfonyl)- N-(6,7,8,9-tetrahydro-2-dibenzofuranyl)-benzamide;

or pharmaceutically acceptable salt thereof.

In some embodiments, $R^1$ is H, $C_{1-12}$ alkyl, $C_{2-12}$ alkenyl, $C_{2-12}$ alkynyl, $C_{1-12}$ haloalkyl, $C_{1-12}$ haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, heteroarylalkynyl, heteroaryl, heteroarylalkyl, heteroarylalkenyl, or heteroarylalkynyl; wherein said $C_{1-12}$ alkyl, $C_{2-12}$ alkenyl, $C_{2-12}$ alkynyl, $C_{1-12}$ haloalkyl, $C_{1-12}$ haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, heteroarylalkynyl, heteroaryl, heteroarylalkyl, heteroarylalkenyl, and heteroarylalkynyl are each optionally substituted with 1, 2, 3, or 4 independently selected $R^5$ groups.

In some embodiments, $R^1$ is H, $C_{1-12}$ alkyl, $C_{1-12}$ haloalkyl, $C_{1-12}$ haloalkoxy, cycloalkyl, cycloalkylalkyl, heterocycloalkyl, heterocycloalkylalkyl, aryl, arylalkyl, heteroaryl, or heteroarylalkyl; wherein said $C_{1-12}$ alkyl, $C_{1-12}$ haloalkyl, $C_{1-12}$ haloalkoxy, cycloalkyl, cycloalkylalkyl, heterocycloalkyl, heterocycloalkylalkyl, aryl, arylalkyl, heteroaryl, and heteroarylalkyl are each optionally substituted with 1, 2, 3, or 4 independently selected $R^5$ groups.

In some embodiments, $R^1$ is $C_{1-12}$ alkyl, $C_{1-12}$ haloalkyl, aryl, arylalkyl, cycloalkyl, cycloalkylalkyl, heterocycloalkyl, heterocycloalkylalkyl, heteroaryl, or heteroarylalkyl; wherein $C_{1-12}$ alkyl, heterocycloalkyl, heterocycloalkylalkyl, aryl, arylalkyl, and heteroarylalkyl are each optionally substituted with 1, 2, 3, or 4 independently selected $R^5$ groups.

In some embodiments, $R^1$ is methyl, ethyl, n-propyl, isopropyl, isobutyl, n-butyl, tert-butyl, n-pentyl, isopentyl, neopentyl, 2,4,4-trimethylpentyl, n-hexyl, chloromethyl, adamantan-1-yl, cyclohexylmethyl, cyclopentylethyl, pyrrolidin-2-yl, (morpholin-4-yl)-methyl, (piperazin-1-yl)-methyl, [1,4-dioxa-8-aza-spiro[4.5]decan-N-yl]-methyl, thiophen-2-yl, furan-2-yl, pyridine-4-yl, (thiophen-2-yl)-methyl, (pyridin-4-yl)-methyl, (pyridin-4-yl)-ethyl, phenyl, benzyl, or 2-phenyl-ethyl, wherein each is optionally substituted with 1, 2, 3, or 4 independently selected $R^5$ groups.

In some embodiments, $R^1$ is $C_{1-12}$ alkyl, $C_{1-12}$ haloalkyl, aryl, arylalkyl, cycloalkyl, cycloalkylalkyl, heterocycloalkyl, heterocycloalkylalkyl, heteroaryl, or heteroarylalkyl; wherein said is $C_{1-12}$ alkyl, heterocycloalkyl, heterocycloalkylalkyl, aryl, arylalkyl, and heteroarylalkyl are each optionally substituted with 1 or 2 $R^5$ groups.

In some embodiments, wherein $R^1$ is $C_{1-12}$ alkyl, heterocycloalkyl, heterocycloalkylalkyl, aryl, arylalkyl, or heteroarylalkyl, each substituted with 1 or 2 $R^5$ groups independently selected from halogen, nitro, $C_{1-12}$ alkyl, $C_{1-12}$ haloalkyl, heteroaryl, $OR^a$, $NR^eR^f$, $C(O)R^b$, $C(O)OR^b$, $NR^cC(O)OR^d$, and $NR^cC(O)R^d$.

In some embodiments, $R^1$ is methyl, ethyl, n-propyl, isopropyl, isobutyl, n-butyl, tert-butyl, n-pentyl, isopentyl, neopentyl, 2,4,4-trimethylpentyl, n-hexyl, chloromethyl, adamantan-1-yl, cyclohexylmethyl, cyclopentylethyl, pyrrolidin-2-yl, (morpholin-4-yl)-methyl, (piperazin-1-yl)-methyl, [1,4-dioxa-8-aza-spiro[4.5]decan-N-yl]-methyl, thiophen-2-yl, furan-2-yl, pyridine-4-yl, (thiophen-2-yl)-methyl, (pyridin-4-yl)-methyl, (pyridin-4-yl)-ethyl, phenyl, benzyl, or 2-phenyl-ethyl.

In some embodiments, $R^1$ is methyl, ethyl, propyl, (piperazin-1-yl)-methyl, pyrrolidin-2-yl, (pyridine-4-yl)ethyl, phenyl, or 2-phenylethyl; wherein each is substituted with 1 or 2 $R^5$ groups independently selected from chloro, fluoro, nitro, methyl, tert-butyl, trifluoromethyl, pyrimidin-2-yl, hydroxyl, methoxy, ethoxy, tert-butoxy, benzyloxy, amino, N-ethyl-N-methylamino, N-methyl-N-(pyridin-2-yl-ethyl)amino, —C(O)CH$_3$, —C(O)CH$_2$CH$_3$, —C(O)O-(tert-butyl), —NHC(O)O—(tert-butyl), —NHC(O)O-(benzyl), and —NHC(O)-(2-phenylethyl); wherein said ethoxy, N-ethyl-N-methylamino, and —NHC(O)—(2-phenylethyl) are each optionally substituted with 1 $R^g$ group selected from N,N-dimethylamino, hydroxyl, and NHC(O)O-(benzyl).

In some embodiments, $R^1$ is —NR$^3$R$^4$ or —OR$^2$.

In some embodiments, $R^1$ is tert-butylamino, dimethylamino, diethylamino, ethoxy, isopropoxy or morpholino.

In some embodiments, each $R^5$ is, independently, $OR^a$, $SR^a$, $C(O)R^b$, $C(O)NR^eR^f$, $C(O)OR^b$, $OC(O)R^b$, $OC(O)NR^eR^f$, $NR^eR^f$, $NR^cC(O)R^d$, $NR^cC(O)OR^d$, $NR^cC(O)NR^d$, $S(O)R^b$, $S(O)NR^eR^f$, $S(O)_2R^b$, $NR^cS(O)_2R^d$, $NR^bS(O)_2NR^eR^f$, halogen, cyano, nitro, $C_{1-6}$ alkyl, $C_{1-6}$ alkenyl, $C_{1-6}$ alkynyl, $C_{1-6}$ haloalkyl, $C_{1-6}$ haloalkoxy, cycloalkyl, cycloalkylalkyl, heterocycloalkyl, heterocycloalkylalkyl, aryl, arylalkyl, heteroaryl, or heteroarylalkyl; wherein said $C_{1-6}$ alkyl, $C_{1-6}$ alkenyl, $C_{1-6}$ alkynyl, $C_{1-6}$ haloalkyl, $C_{1-6}$ haloalkoxy, cycloalkyl, cycloalkylalkyl, heterocycloalkyl, heterocycloalkylalkyl, aryl, arylalkyl, heteroaryl, and heteroarylalkyl are each optionally substituted with 1, 2, 3, or 4 independently selected $R^8$ groups.

In some embodiments, each $R^5$ is, independently, $OR^a$, $SR^a$, $C(O)R^b$, $C(O)NR^eR^f$, $C(O)OR^b$, $OC(O)R^b$, $OC(O)NR^eR^f$, $NR^eR^f$, $NR^cC(O)R^d$, $NR^cC(O)$ $OR^d$, $NR^cC(O)NR^d$, halogen, cyano, nitro, $C_{1-6}$ alkyl, $C_{1-6}$ haloalkyl, $C_{1-6}$ haloalkoxy, cycloalkyl, cycloalkylalkyl, heterocycloalkyl, heterocycloalkylalkyl, aryl, arylalkyl, heteroaryl, or heteroarylalkyl; wherein said $C_{1-6}$ alkyl, $C_{1-6}$ haloalkyl, $C_{1-6}$ haloalkoxy, cycloalkyl, cycloalkylalkyl, heterocycloalkyl, heterocycloalkylalkyl, aryl, arylalkyl, heteroaryl, and heteroarylalkyl are each optionally substituted with 1, 2, 3, or 4 independently selected $R^8$ groups.

In some embodiments, each $R^5$ is, independently, $OR^a$, $SR^a$, $C(O)R^b$, $C(O)NR^eR^f$, $C(O)OR^b$, $OC(O)R^b$, $OC(O)NR^eR^f$, $NR^eR^f$, $NR^cC(O)R^d$, $NR^cC(O)OR^d$, $NR^cC(O)NR^d$, halogen, cyano, nitro, $C_{1-6}$ alkyl, $C_{1-6}$ haloalkyl, cycloalkyl, heterocycloalkyl, aryl, or heteroaryl; wherein said $C_{1-6}$ alkyl, $C_{1-6}$ haloalkyl, cycloalkyl, heterocycloalkyl, aryl, and heteroaryl are each optionally substituted with 1, 2, 3, or 4 independently selected $R^8$ groups.

In some embodiments, each $R^5$ is, independently, $OR^a$, $SR^a$, $C(O)R^b$, $C(O)NR^eR^f$, $C(O)OR^b$, $OC(O)R^b$, $OC(O)NR^eR^f$, $NR^eR^f$, $NR^cC(O)R^d$, $NR^cC(O)$ $OR^d$, $NR^cC(O)NR^d$, halogen, cyano, nitro, $C_{1-6}$ alkyl, $C_{1-6}$ haloalkyl, cycloalkyl, heterocycloalkyl, aryl, or heteroaryl.

In some embodiments, each $R^5$ is, independently, $OR^a$, $C(O)R^b$, $C(O)OR^b$, $NR^eR^f$, $NR^eC(O)R^d$, $NR^eC(O)OR^d$, halogen, nitro, $C_{1-6}$ alkyl, $C_{1-6}$ haloalkyl, or heteroaryl.

In some embodiments, each $R^5$ is, independently, chloro, fluoro, nitro, methyl, tert-butyl, trifluoromethyl, pyrimidin-2-yl, hydroxyl, methoxy, ethoxy, tert-butoxy, benzyloxy, amino, N-ethyl-N-methylamino, N-methyl-N-(pyridin-2-yl-ethyl)amino, —C(O)CH$_3$, —C(O)CH$_2$CH$_3$, —C(O)O-(tert-butyl), —NHC(O)O-(tert-butyl), —NHC(O)O-(benzyl), and —NHC(O)-(2-phenylethyl); wherein said methyl, tert-butyl, trifluoromethyl, pyrimidin-2-yl, hydroxyl, methoxy, ethoxy, tert-butoxy, benzyloxy, amino, N-ethyl-N-methylamino, N-methyl-N-(pyridin-2-yl-ethyl)amino, —C(O)CH$_3$, —C(O)CH$_2$CH$_3$, —C(O)O-(tert-butyl), —NHC(O)O-(tert-butyl), —NHC(O)O-(benzyl), and —NHC(O)-(2-phenylethyl) are each optionally substituted with 1 $R^g$ group.

In some embodiments, each $R^g$ is, independently, $OR^u$, $SR^u$, $C(O)R^v$, $C(O)NR^yR^z$, $C(O)OR^v$, $OC(O)R^v$, $OC(O)NR^yR^z$, $NR^yR^z$, $NR^wC(O)R^x$, $NR^wC(O)OR^x$, $NR^wC(O)NR^x$, halogen, cyano, nitro, $C_{1-6}$alkyl, $C_{1-6}$haloalkyl, $C_{1-6}$haloalkoxy.

In some embodiments, each $R^g$ is, independently, $OR^u$, $NR^yR^z$, or $NR^wC(O)OR^x$.

In some embodiments, each $R^g$ is, independently, N,N-dimethylamino, hydroxyl, and NHC(O)O-(benzyl).

In some embodiments, $L^1$ is a $C_{3-6}$ alkylene bridge, which is optionally substituted with 1, 2, or 3 groups independently selected from $OR^o$, $SR^o$, $C(O)R^p$, $C(O)NR^sR^t$, $C(O)OR^p$, $OC(O)R^p$, $OC(O)NR^sR^t$, $NR^qC(O)R^r$, $NR^qC(O)OR^r$, $NR^qC(O)NR^r$, oxo, halogen, cyano, nitro, $C_{1-6}$ alkyl, $C_{1-6}$ haloalkyl, $C_{1-6}$ haloalkoxy, cycloalkyl, cycloalkylalkyl, heterocycloalkyl, heterocycloalkylalkyl, heterocycloalkylalkenyl, heterocycloalkylalkynyl, aryl, arylalkyl, heteroaryl, and heteroarylalkyl; wherein said $C_{1-6}$ alkyl, $C_{1-6}$ haloalkyl, $C_{1-6}$ haloalkoxy, cycloalkyl, cycloalkylalkyl, heterocycloalkyl, heterocycloalkylalkyl, aryl, arylalkyl, heteroaryl, and heteroarylalkyl are each optionally substituted with 1, 2, or 3 independently selected $R^6$ groups.

In some embodiments, $L^1$ is a $C_{3-6}$ alkylene bridge, which is optionally substituted with 1, 2, or 3 groups independently selected from $OR^o$, $SR^o$, $C(O)R^p$, $C(O)NR^sR^t$, $C(O)OR^p$, $NR^qC(O)R^r$, $NR^qC(O)OR^r$, $NR^qC(O)NR^r$, oxo, halogen, cyano, nitro, $C_{1-6}$ alkyl, $C_{1-6}$ haloalkyl, cycloalkyl, cycloalkylalkyl, heterocycloalkyl, heterocycloalkylalkyl, heterocycloalkylalkenyl, heterocycloalkylalkynyl, aryl, arylalkyl, heteroaryl, and heteroarylalkyl.

In some embodiments, $L^1$ is an unsubstituted $C_{3-6}$alkylene bridge.

In some embodiments, $L^1$ is an unsubstituted $C_3$alkylene bridge.

In some embodiments, $L^1$ is an unsubstituted $C_4$alkylene bridge.

In some embodiments, $L^1$ is an unsubstituted $C_5$alkylene bridge

In some embodiments, $L^1$ is an unsubstituted $C_6$alkylene bridge

In some embodiments:
$R^1$ is H, $C_{1-12}$ alkyl, $C_{2-12}$ alkenyl, $C_{2-12}$ alkynyl, $C_{1-12}$ haloalkyl, $C_{1-12}$ haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, heteroarylalkynyl, heteroaryl, heteroarylalkyl, heteroarylalkenyl, or heteroarylalkynyl; wherein said $C_{1-12}$ alkyl, $C_{2-12}$ alkenyl, $C_{2-12}$ alkynyl, $C_{1-12}$ haloalkyl, $C_{1-12}$ haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, heteroarylalkynyl, heteroaryl, heteroarylalkyl, heteroarylalkenyl, and heteroarylalkynyl are each optionally substituted with 1, 2, 3, or 4 independently selected $R^5$ groups; and $L^1$ is a $C_{3-6}$ alkylene bridge, which is optionally substituted with 1, 2, or 3 groups independently selected from $OR^o$, $SR^o$, $C(O)R^p$, $C(O)NR^sR^t$, $C(O)OR^p$, $OC(O)R^p$, $OC(O)NR^sR^t$, $NR^qC(O)R^r$, $NR^qC(O)OR^r$, $NR^qC(O)NR^r$, oxo, halogen, cyano, nitro, $C_{1-6}$ alkyl, $C_{1-6}$ alkenyl, $C_{1-6}$ alkynyl, $C_{1-6}$ haloalkyl, $C_{1-6}$ haloalkoxy, cycloalkyl, cycloalkylalkyl, heterocycloalkyl, heterocycloalkylalkyl, heterocycloalkylalkenyl, heterocycloalkylalkynyl, aryl, arylalkyl, heteroaryl, and heteroarylalkyl; wherein said $C_{1-6}$ alkyl, $C_{1-6}$ alkenyl, $C_{1-6}$ alkynyl, $C_{1-6}$ haloalkyl, $C_{1-6}$ haloalkoxy, cycloalkyl, cycloalkylalkyl, heterocycloalkyl, heterocycloalkylalkyl, aryl, arylalkyl, heteroaryl, and heteroarylalkyl are each optionally substituted with 1, 2, or 3 independently selected $R^6$ groups.

In some embodiments:
$R^1$ is H, $C_{1-12}$ alkyl, $C_{1-12}$ haloalkyl, $C_{1-12}$ haloalkoxy, cycloalkyl, cycloalkylalkyl, heterocycloalkyl, heterocycloalkylalkyl, aryl, arylalkyl, heteroaryl, or heteroarylalkyl; wherein said $C_{1-12}$ alkyl, $C_{1-12}$ haloalkyl, $C_{1-12}$ haloalkoxy, cycloalkyl, cycloalkylalkyl, heterocycloalkyl, heterocycloalkylalkyl, aryl, arylalkyl, heteroaryl, and heteroarylalkyl are each optionally substituted with 1, 2, 3, or 4 independently selected $R^5$ groups; and $L^1$ is a $C_{3-6}$ alkylene bridge, which is optionally substituted with 1, 2, or 3 groups independently selected from $OR^o$, $SR^o$, $C(O)R^p$, $C(O)NR^sR^t$, $C(O)OR^p$, $NR^qC(O)R^r$, $NR^qC(O)OR^r$, $NR^qC(O)NR^r$, oxo, halogen, cyano, nitro, $C_{1-6}$ alkyl, $C_{1-6}$ haloalkyl, cycloalkyl, cycloalkylalkyl, heterocycloalkyl, heterocycloalkylalkyl, heterocycloalkylalkenyl, heterocycloalkylalkynyl, aryl, arylalkyl, heteroaryl, and heteroarylalkyl.

In some embodiments:
$R^1$ is $C_{1-12}$ alkyl, $C_{1-12}$ haloalkyl, aryl, arylalkyl, cycloalkyl, cycloalkylalkyl, heterocycloalkyl, heterocycloalkylalkyl, heteroaryl, or heteroarylalkyl; wherein $C_{1-12}$ alkyl, heterocycloalkyl, heterocycloalkylalkyl, aryl, arylalkyl, and heteroarylalkyl are each optionally substituted with 1, 2, 3, or 4 independently selected $R^5$ groups; and $L^1$ is a $C_{3-6}$ alkylene bridge, which is optionally substituted with 1, 2, or 3 groups independently selected from $OR^o$, $SR^o$, $C(O)R^p$, $C(O)NR^sR^t$, $C(O)OR^p$, $NR^qC(O)R^r$, $NR^qC(O)OR^r$, $NR^qC(O)NR^r$, oxo, halogen, cyano, nitro, $C_{1-6}$ alkyl, $C_{1-6}$ haloalkyl, cycloalkyl, cycloalkylalkyl, heterocycloalkyl, heterocycloalkylalkyl, heterocycloalkylalkenyl, heterocycloalkylalkynyl, aryl, arylalkyl, heteroaryl, and heteroarylalkyl.

In some embodiments:
$R^1$ is $C_{1-12}$ alkyl, $C_{1-12}$ haloalkyl, aryl, arylalkyl, cycloalkyl, cycloalkylalkyl, heterocycloalkyl, heterocycloalkylalkyl, heteroaryl, or heteroarylalkyl; wherein $C_{1-12}$ alkyl, heterocycloalkyl, heterocycloalkylalkyl, aryl, arylalkyl, and heteroarylalkyl are each optionally substituted with 1, 2, 3, or 4 independently selected $R^5$ groups; and $L^1$ is an unsubstituted $C_{3-6}$ alkylene bridge.

In some embodiments:
$R^1$ is $C_{1-12}$ alkyl, $C_{1-12}$ haloalkyl, aryl, arylalkyl, cycloalkyl, cycloalkylalkyl, heterocycloalkyl, heterocycloalkylalkyl, heteroaryl, or heteroarylalkyl; wherein $C_{1-12}$ alkyl, heterocycloalkyl, heterocycloalkylalkyl, aryl, arylalkyl, and heteroarylalkyl are each optionally substituted with 1, 2, 3, or 4 independently selected $R^5$ groups;

$L^1$ is an unsubstituted $C_{3-6}$ alkylene bridge; and each $R^5$ is, independently, $OR^a$, $SR^a$, $C(O)R^b$, $C(O)NR^eR^f$, $C(O)OR^b$, $OC(O)R^b$, $OC(O)NR^eR^f$, $NR^eR^f$, $NR^cC(O)R^d$, $NR^cC(O)OR^d$, $NR^cC(O)NR^d$, halogen, cyano, nitro, $C_{1-6}$ alkyl, $C_{1-6}$ haloalkyl, $C_{1-6}$ haloalkoxy, cycloalkyl, cycloalkylalkyl, heterocycloalkyl, heterocycloalkylalkyl, aryl, arylalkyl, heteroaryl, or heteroarylalkyl; wherein said $C_{1-6}$ alkyl, $C_{1-6}$ haloalkyl, $C_{1-6}$ haloalkoxy, cycloalkyl, cycloalkylalkyl, heterocycloalkyl, heterocycloalkylalkyl, aryl, arylalkyl, heteroaryl, and heteroarylalkyl are each optionally substituted with 1, 2, 3, or 4 independently selected $R^8$ groups.

In some embodiments:
$R^1$ is $C_{1-12}$ alkyl, $C_{1-12}$ haloalkyl, aryl, arylalkyl, cycloalkyl, cycloalkylalkyl, heterocycloalkyl, heterocycloalkylalkyl, heteroaryl, or heteroarylalkyl; wherein $C_{1-12}$ alkyl, heterocycloalkyl, heterocycloalkylalkyl, aryl, arylalkyl, and heteroarylalkyl are each optionally substituted with 1, 2, 3, or 4 independently selected $R^5$ groups;

$L^1$ is an unsubstituted $C_{3-6}$ alkylene bridge; and each $R^5$ is, independently, $OR^a$, $SR^a$, $C(O)R^b$, $C(O)NR^eR^f$, $C(O)OR^b$, $OC(O)R^b$, $OC(O)NR^eR^f$, $NR^eR^f$, $NR^cC(O)R^d$, $NR^cC(O)OR^d$, $NR^cC(O)NR^d$, halogen, cyano, nitro, $C_{1-6}$ alkyl, $C_{1-6}$ haloalkyl, cycloalkyl, heterocycloalkyl, aryl, or heteroaryl; wherein said $C_{1-6}$ alkyl, $C_{1-6}$ haloalkyl, cycloalkyl, heterocycloalkyl, aryl, and heteroaryl are each optionally substituted with 1, 2, 3, or 4 independently selected $R^8$ groups.

In some embodiments:
$R^1$ is $C_{1-12}$ alkyl, $C_{1-12}$ haloalkyl, aryl, arylalkyl, cycloalkyl, cycloalkylalkyl, heterocycloalkyl, heterocycloalkylalkyl, heteroaryl, or heteroarylalkyl; wherein $C_{1-12}$ alkyl, heterocycloalkyl, heterocycloalkylalkyl, aryl, arylalkyl, and heteroarylalkyl are each optionally substituted with 1, 2, 3, or 4 independently selected $R^5$ groups;

$L^1$ is an unsubstituted $C_{3-6}$ alkylene bridge; and each $R^5$ is, independently, $OR^a$, $SR^a$, $C(O)R^b$, $C(O)NR^eR^f$, $C(O)OR^b$, $OC(O)R^b$, $OC(O)NR^eR^f$, $NR^eR^f$, $NR^cC(O)R^d$, $NR^cC(O)OR^d$, $NR^cC(O)NR^d$, halogen, cyano, nitro, $C_{1-6}$ alkyl, $C_{1-6}$ haloalkyl, cycloalkyl, heterocycloalkyl, aryl, or heteroaryl.

In some embodiments:
$R^1$ is $C_{1-12}$ alkyl, $C_{1-12}$ haloalkyl, aryl, arylalkyl, cycloalkyl, cycloalkylalkyl, heterocycloalkyl, heterocycloalkylalkyl, heteroaryl, or heteroarylalkyl; wherein $C_{1-12}$ alkyl, heterocycloalkyl, heterocycloalkylalkyl, aryl, arylalkyl, and heteroarylalkyl are each optionally substituted with 1, 2, 3, or 4 independently selected $R^5$ groups;

$L^1$ is an unsubstituted $C_{3-6}$ alkylene bridge; and each $R^5$ is, independently, $OR^a$, $C(O)R^b$, $C(O)OR^b$, $NR^eR^f$, $NR^cC(O)R^d$, $NR^cC(O)OR^d$, halogen, nitro, $C_{1-6}$ alkyl, $C_{1-6}$ haloalkyl, or heteroaryl.

In some embodiments:
$R^1$ is $C_{1-12}$ alkyl, $C_{1-12}$ haloalkyl, aryl, arylalkyl, cycloalkyl, cycloalkylalkyl, heterocycloalkyl, heterocycloalkylalkyl, heteroaryl, or heteroarylalkyl; wherein $C_{1-12}$ alkyl, heterocycloalkyl, heterocycloalkylalkyl, aryl, arylalkyl, and heteroarylalkyl are each optionally substituted with 1, 2, 3, or 4 independently selected $R^5$ groups;

$L^1$ is an unsubstituted $C_{3-6}$ alkylene bridge;

each $R^5$ is, independently, $OR^a$, $C(O)R^b$, $C(O)OR^b$, $NR^eR^f$, $NR^cC(O)R^d$, $NR^cC(O)OR^d$, halogen, nitro, $C_{1-6}$ alkyl, $C_{1-6}$ haloalkyl, or heteroaryl; and each $R^g$ is, independently, $OR^u$, $SR^u$, $C(O)R^v$, $C(O)NR^yR^z$, $C(O)OR^v$, $OC(O)R^v$, $OC(O)NR^yR^z$, $NR^yR^z$, $NR^wC(O)R^x$, $NR^wC(O)OR^x$, $NR^wC(O)NR^x$, halogen, cyano, nitro, $C_{1-6}$ alkyl, $C_{1-6}$ haloalkyl, $C_{1-6}$ haloalkoxy.

In some embodiments:
$R^1$ is $C_{1-12}$ alkyl, $C_{1-12}$ haloalkyl, aryl, arylalkyl, cycloalkyl, cycloalkylalkyl, heterocycloalkyl, heterocycloalkylalkyl, heteroaryl, or heteroarylalkyl; wherein $C_{1-12}$ alkyl, heterocycloalkyl, heterocycloalkylalkyl, aryl, arylalkyl, and heteroarylalkyl are each optionally substituted with 1, 2, 3, or 4 independently selected $R^5$ groups;

$L^1$ is an unsubstituted $C_{3-6}$ alkylene bridge;

each $R^5$ is, independently, $OR^a$, $C(O)R^b$, $C(O)OR^b$, $NR^eR^f$, $NR^cC(O)R^d$, $NR^cC(O)OR^d$, halogen, nitro, $C_{1-6}$ alkyl, $C_{1-6}$ haloalkyl, or heteroaryl; and each $R^g$ is, independently, $OR^u$, $NR^yR^z$, or $NR^wC(O)OR^x$.

In some embodiments:
$R^1$ is $C_{1-12}$ alkyl, $C_{1-12}$ haloalkyl, aryl, arylalkyl, cycloalkyl, cycloalkylalkyl, heterocycloalkyl, heterocycloalkylalkyl, heteroaryl, or heteroarylalkyl; wherein said is $C_{1-12}$ alkyl, heterocycloalkyl, heterocycloalkylalkyl, aryl, arylalkyl, and heteroarylalkyl are each optionally substituted with 1 or 2 $R^5$ groups; and $L^1$ is an unsubstituted $C_{3-6}$ alkylene bridge.

In some embodiments:
$R^1$ is $C_{1-12}$ alkyl, $C_{1-12}$ haloalkyl, aryl, arylalkyl, cycloalkyl, cycloalkylalkyl, heterocycloalkyl, heterocycloalkylalkyl, heteroaryl, or heteroarylalkyl; wherein said is $C_{1-12}$ alkyl, heterocycloalkyl, heterocycloalkylalkyl, aryl, arylalkyl, and heteroarylalkyl are each optionally substituted with 1 or 2 $R^5$ groups;

$L^1$ is an unsubstituted $C_{3-6}$ alkylene bridge;

each $R^5$ is, independently, $OR^a$, $SR^a$, $C(O)R^b$, $C(O)NR^eR^f$, $C(O)OR^b$, $OC(O)R^b$, $OC(O)NR^eR^f$, $NR^eR^f$, $NR^cC(O)R^d$, $NR^cC(O)OR^d$, $NR^cC(O)NR^d$, halogen, cyano, nitro, $C_{1-6}$ alkyl, $C_{1-6}$ haloalkyl, $C_{1-6}$ haloalkoxy, cycloalkyl, cycloalkylalkyl, heterocycloalkyl, heterocycloalkylalkyl, aryl, arylalkyl, heteroaryl, or heteroarylalkyl; wherein said $C_{1-6}$ alkyl, $C_{1-6}$ haloalkyl, $C_{1-6}$ haloalkoxy, cycloalkyl, cycloalkylalkyl, heterocycloalkyl, heterocycloalkylalkyl, aryl, arylalkyl, heteroaryl, and heteroarylalkyl are each optionally substituted with 1, 2, 3, or 4 independently selected $R^8$ groups.

In some embodiments:
$R^1$ is $C_{1-12}$ alkyl, $C_{1-12}$ haloalkyl, aryl, arylalkyl, cycloalkyl, cycloalkylalkyl, heterocycloalkyl, heterocycloalkylalkyl, heteroaryl, or heteroarylalkyl; wherein said is $C_{1-12}$ alkyl, heterocycloalkyl, heterocycloalkylalkyl, aryl, arylalkyl, and heteroarylalkyl are each optionally substituted with 1 or 2 $R^5$ groups;

$L^1$ is an unsubstituted $C_{3-6}$ alkylene bridge;

each $R^5$ is, independently, $OR^a$, $SR^a$, $C(O)R^b$, $C(O)NR^eR^f$, $C(O)OR^b$, $OC(O)R^b$, $OC(O)NR^eR^f$, $NR^eR^f$, $NR^cC(O)R^d$, $NR^cC(O)OR^d$, $NR^cC(O)NR^d$, halogen, cyano, nitro, $C_{1-6}$alkyl, $C_{1-6}$ haloalkyl, cycloalkyl, heterocycloalkyl, aryl, or heteroaryl; wherein said $C_{1-6}$alkyl, $C_{1-6}$ haloalkyl, cycloalkyl, heterocycloalkyl, aryl, and heteroaryl are each optionally substituted with 1, 2, 3, or 4 independently selected $R^8$ groups.

In some embodiments:
$R^1$ is $C_{1-12}$ alkyl, $C_{1-12}$ haloalkyl, aryl, arylalkyl, cycloalkyl, cycloalkylalkyl, heterocycloalkyl, heterocycloalkylalkyl, heteroaryl, or heteroarylalkyl; wherein said is $C_{1-12}$ alkyl, heterocycloalkyl, heterocycloalkylalkyl, aryl, arylalkyl, and heteroarylalkyl are each optionally substituted with 1 or 2 $R^5$ groups;

$L^1$ is an unsubstituted $C_{3-6}$ alkylene bridge; and each $R^5$ is, independently, $OR^a$, $SR^a$, $C(O)R^b$, $C(O)NR^eR^f$, $C(O)OR^b$, $OC(O)R^b$, $OC(O)NR^eR^f$, $NR^eR^f$, $NR^cC(O)R^d$, $NR^cC(O)OR^d$, $NR^cC(O)NR^d$, halogen, cyano, nitro, $C_{1-6}$ alkyl, $C_{1-6}$ haloalkyl, cycloalkyl, heterocycloalkyl, aryl, or heteroaryl.

In some embodiments:
$R^1$ is $C_{1-12}$ alkyl, $C_{1-12}$ haloalkyl, aryl, arylalkyl, cycloalkyl, cycloalkylalkyl, heterocycloalkyl, heterocycloalkylalkyl, heteroaryl, or heteroarylalkyl; wherein said is $C_{1-12}$ alkyl, heterocycloalkyl, heterocycloalkylalkyl, aryl, arylalkyl, and heteroarylalkyl are each optionally substituted with 1 or 2 $R^5$ groups;

$L^1$ is an unsubstituted $C_{3-6}$ alkylene bridge; and each $R^5$ is, independently, $OR^a$, $C(O)R^b$, $C(O)OR^b$, $NR^eR^f$, $NR^cC(O)R^d$, $NR^cC(O)OR^d$, halogen, nitro, $C_{1-6}$ alkyl, $C_{1-6}$ haloalkyl, or heteroaryl.

In some embodiments:
$R^1$ is $C_{1-12}$ alkyl, $C_{1-12}$ haloalkyl, aryl, arylalkyl, cycloalkyl, cycloalkylalkyl, heterocycloalkyl, heterocycloalkylalkyl, heteroaryl, or heteroarylalkyl; wherein said is $C_{1-12}$ alkyl, heterocycloalkyl, heterocycloalkylalkyl, aryl, arylalkyl, and heteroarylalkyl are each optionally substituted with 1 or 2 $R^5$ groups;

$L^1$ is an unsubstituted $C_{3-6}$ alkylene bridge;

each $R^5$ is, independently, $OR^a$, $C(O)R^b$, $C(O)OR^b$, $NR^eR^f$, $NR^cC(O)R^d$, $NR^cC(O)OR^d$, halogen, nitro, $C_{1-6}$ alkyl, $C_{1-6}$ haloalkyl, or heteroaryl; and each $R^g$ is, independently, $OR^u$, $SR^u$, $C(O)R^v$, $C(O)NR^yR^z$, $C(O)OR^v$, $OC(O)R^v$, $OC(O)NR^yR^z$, $NR^yR^z$, $NR^wC(O)R^x$, $NR^wC(O)OR^x$, $NR^wC(O)NR^x$, halogen, cyano, nitro, $C_{1-6}$ alkyl, $C_{1-6}$ haloalkyl, $C_{1-6}$ haloalkoxy.

In some embodiments:
$R^1$ is $C_{1-12}$ alkyl, $C_{1-12}$ haloalkyl, aryl, arylalkyl, cycloalkyl, cycloalkylalkyl, heterocycloalkyl, heterocycloalkylalkyl, heteroaryl, or heteroarylalkyl; wherein said is $C_{1-12}$ alkyl, heterocycloalkyl, heterocycloalkylalkyl, aryl, arylalkyl, and heteroarylalkyl are each optionally substituted with 1 or 2 $R^5$ groups;

$L^1$ is an unsubstituted $C_{3-6}$ alkylene bridge;

each $R^5$ is, independently, $OR^a$, $C(O)R^b$, $C(O)OR^b$, $NR^eR^f$, $NR^cC(O)R^d$, $NR^cC(O)OR^d$, halogen, nitro, $C_{1-6}$ alkyl, $C_{1-6}$ haloalkyl, or heteroaryl; and each $R^g$ is, independently, $OR^u$, $NR^yR^z$, or $NR^wC(O)OR^x$.

In some embodiments:
$R^1$ is methyl, ethyl, n-propyl, isopropyl, isobutyl, n-butyl, tert-butyl, n-pentyl, isopentyl, neopentyl, 2,4,4-trimethylpentyl, n-hexyl, chloromethyl, adamantan-1-yl, cyclohexylmethyl, cyclopentylethyl, pyrrolidin-2-yl, (morpholin-4-yl)-methyl, (piperazin-1-yl)-methyl, [1,4-dioxa-8-aza-spiro[4.5]decan-N-yl]-methyl, thiophen-2-yl, furan-2-yl, pyridine-4-yl, (thiophen-2-yl)-methyl, (pyridin-4-yl)-methyl, (pyridin-4-yl)-ethyl, phenyl, benzyl, or 2-phenyl-ethyl, wherein each is optionally substituted with 1, 2, 3, or 4 independently selected $R^5$ groups; and $L^1$ is an unsubstituted $C_{3-6}$ alkylene bridge.

In some embodiments:
$R^1$ is methyl, ethyl, n-propyl, isopropyl, isobutyl, n-butyl, tert-butyl, n-pentyl, isopentyl, neopentyl, 2,4,4-trimethylpentyl, n-hexyl, chloromethyl, adamantan-1-yl, cyclohexylmethyl, cyclopentylethyl, pyrrolidin-2-yl, (morpholin-4-yl)-methyl, (piperazin-1-yl)-methyl, [1,4-dioxa-8-aza-spiro[4.5]decan-N-yl]-methyl, thiophen-2-yl, furan-2-yl, pyridine-4-yl, (thiophen-2-yl)-methyl, (pyridin-4-yl)-methyl, (pyridin-4-yl)-ethyl, phenyl, benzyl, or 2-phenyl-ethyl, wherein each is optionally substituted with 1, 2, 3, or 4 independently selected $R^5$ groups;

$L^1$ is an unsubstituted $C_{3-6}$ alkylene bridge; and each $R^5$ is, independently, chloro, fluoro, nitro, methyl, tert-butyl, trifluoromethyl, pyrimidin-2-yl, hydroxyl, methoxy, ethoxy, tert-butoxy, benzyloxy, amino, N-ethyl-N-methylamino, N-methyl-N-(pyridin-2-yl-ethyl)amino, —C(O)CH$_3$, —C(O)CH$_2$CH$_3$, —C(O)O-(tert-butyl), —NHC(O)O-(tert-butyl), —NHC(O)O-(benzyl), and —NHC(O)-(2-phenylethyl); wherein said methyl, tert-butyl, trifluoromethyl, pyrimidin-2-yl, hydroxyl, methoxy, ethoxy, tert-butoxy, benzyloxy, amino, N-ethyl-N-methylamino, N-methyl-N-(pyridin-2-yl-ethyl)amino, —C(O)CH$_3$, —C(O)CH$_2$CH$_3$, —C(O)O-(tert-butyl), —NHC(O)O-(tert-butyl), —NHC(O)O-(benzyl), and —NHC(O)—(2-phenylethyl) are each optionally substituted with 1 $R^g$ group.

In some embodiments:
$R^1$ is methyl, ethyl, n-propyl, isopropyl, isobutyl, n-butyl, tert-butyl, n-pentyl, isopentyl, neopentyl, 2,4,4-trimethylpentyl, n-hexyl, chloromethyl, adamantan-1-yl, cyclohexylmethyl, cyclopentylethyl, pyrrolidin-2-yl, (morpholin-4-yl)-methyl, (piperazin-1-yl)-methyl, [1,4-dioxa-8-aza-spiro[4.5]decan-N-yl]-methyl, thiophen-2-yl, furan-2-yl, pyridine-4-yl, (thiophen-2-yl)-methyl, (pyridin-4-yl)-methyl, (pyridin-4-yl)-ethyl, phenyl, benzyl, or 2-phenyl-ethyl, wherein each is optionally substituted with 1, 2, 3, or 4 independently selected $R^5$ groups;

$L^1$ is an unsubstituted $C_{3-6}$ alkylene bridge;

each $R^5$ is, independently, chloro, fluoro, nitro, methyl, tert-butyl, trifluoromethyl, pyrimidin-2-yl, hydroxyl, methoxy, ethoxy, tert-butoxy, benzyloxy, amino, N-ethyl-N-methylamino, N-methyl-N-(pyridin-2-yl-ethyl)amino, —C(O)CH$_3$, —C(O)CH$_2$CH$_3$, —C(O)O-(tert-butyl), —NHC(O)O-(tert-butyl), —NHC(O)O-(benzyl), and —NHC(O)-(2-phenylethyl); wherein said methyl, tert-butyl, trifluoromethyl, pyrimidin-2-yl, hydroxyl, methoxy, ethoxy, tert-butoxy, benzyloxy, amino, N-ethyl-N-methylamino, N-methyl-N-(pyridin-2-yl-ethyl)amino, —C(O)CH$_3$, —C(O)CH$_2$CH$_3$, —C(O)O-(tert-butyl), —NHC(O)O-(tert-butyl), —NHC(O)O-(benzyl), and —NHC(O)-(2-phenylethyl) are each optionally substituted with 1 $R^g$ group; and each $R^1$ is, independently, $OR^u$, $NR^yR^z$, or $NR^wC(O)OR^x$.

In some embodiments:
$R^1$ is methyl, ethyl, n-propyl, isopropyl, isobutyl, n-butyl, tert-butyl, n-pentyl, isopentyl, neopentyl, 2,4,4-trimethylpentyl, n-hexyl, chloromethyl, adamantan-1-yl, cyclohexylmethyl, cyclopentylethyl, pyrrolidin-2-yl, (morpholin-4-yl)-methyl, (piperazin-1-yl)-methyl, [1,4-dioxa-8-aza-spiro[4.5]decan-N-yl]-methyl, thiophen-2-yl, furan-2-yl, pyridine-4-yl, (thiophen-2-yl)-methyl, (pyridin-4-yl)-methyl, (pyridin-4-yl)-ethyl, phenyl, benzyl, or 2-phenyl-ethyl, wherein each is optionally substituted with 1, 2, 3, or 4 independently selected $R^5$ groups;

$L^1$ is an unsubstituted $C_{3-6}$ alkylene bridge;

each $R^5$ is, independently, chloro, fluoro, nitro, methyl, tert-butyl, trifluoromethyl, pyrimidin-2-yl, hydroxyl, methoxy, ethoxy, tert-butoxy, benzyloxy, amino, N-ethyl-N-methylamino, N-methyl-N-(pyridin-2-yl-ethyl)amino, —C(O)CH$_3$, —C(O)CH$_2$CH$_3$, —C(O)O-(tert-butyl), —NHC(O)O-(tert-butyl), —NHC(O)O-(benzyl), and —NHC(O)-(2-phenylethyl); wherein said methyl, tert-butyl, trifluoromethyl, pyrimidin-2-yl, hydroxyl, methoxy, ethoxy, tert-butoxy, benzyloxy, amino, N-ethyl-N-methylamino, N-methyl-N-(pyridin-2-yl-ethyl)amino, —C(O)CH$_3$, —C(O)CH$_2$CH$_3$, —C(O)O-(tert-butyl), —NHC(O)O-(tert-butyl), —NHC(O)O-(benzyl), and —NHC(O)-(2-phenylethyl) are each optionally substituted with 1 $R^g$ group; and each $R^g$ is, independently, N,N-dimethylamino, hydroxyl, and NHC(O)O-(benzyl).

In some embodiments:

$R^1$ is methyl, ethyl, n-propyl, isopropyl, isobutyl, n-butyl, tert-butyl, n-pentyl, isopentyl, neopentyl, 2,4,4-trimethylpentyl, n-hexyl, chloromethyl, adamantan-1-yl, cyclohexylmethyl, cyclopentylethyl, pyrrolidin-2-yl, (morpholin-4-yl)-methyl, (piperazin-1-yl)-methyl, [1,4-dioxa-8-aza-spiro[4.5]decan-N-yl]-methyl, thiophen-2-yl, furan-2-yl, pyridine-4-yl, (thiophen-2-yl)-methyl, (pyridin-4-yl)-methyl, (pyridin-4-yl)-ethyl, phenyl, benzyl, or 2-phenyl-ethyl; and $L^1$ is an unsubstituted $C_{3-6}$ alkylene bridge.

In some embodiments:

$R^1$ is methyl, ethyl, propyl, (piperazin-1-yl)-methyl, pyrrolidin-2-yl, (pyridine-4-yl)ethyl, phenyl, or 2-phenylethyl; wherein each is substituted with 1 or 2 $R^5$ groups.

$L^1$ is an unsubstituted $C_{3-6}$ alkylene bridge;

each $R^5$ is, independently, chloro, fluoro, nitro, methyl, tert-butyl, trifluoromethyl, pyrimidin-2-yl, hydroxyl, methoxy, ethoxy, tert-butoxy, benzyloxy, amino, N-ethyl-N-methylamino, N-methyl-N-(pyridin-2-yl-ethyl)amino, —C(O)CH$_3$, —C(O)CH$_2$CH$_3$, —C(O)O-(tert-butyl), —NHC(O)O-(tert-butyl), —NHC(O)O-(benzyl), and —NHC(O)-(2-phenylethyl); wherein said ethoxy, N-ethyl-N-methylamino, and —NHC(O)-(2-phenylethyl) are each optionally substituted with 1 $R^g$ group; and each $R^g$ is, independently, N,N-dimethylamino, hydroxyl, or NHC(O)O-(benzyl).

In some embodiments:

$R^1$ is —OR$^2$ or —NR$^3$R$^4$; and $L^1$ is an unsubstituted $C_{4-6}$ alkylene bridge.

In some embodiments:

$R^1$ is tert-butylamino, dimethylamino, diethylamino, ethoxy, isopropoxy or morpholino; and $L^1$ is an unsubstituted $C_{4-6}$ alkylene bridge.

In some embodiments, when $L^1$ is a $C_4$ alkylene bridge, $R_1$ is not a group selected from (9H-xanthan-9-yl)methyl, (phenylmethyl)thiomethyl, 3-oxo-3-methoxy-propyl, 2,2-dimethyl-N-(1,2,3,4-tetrahydro-8-dibenzofuranyl)-ethanamidyl, 3-chlorobenzo[b]thiophen-2-yl, 2-methoxy-4-(methylthio)-phenyl, cyclohexyl, cyclopentyl, 3-(trifluoromethyl)phenyl, 4-(trifluoromethyl)phenyl, adamantan-1-yl-amino, 3-chloroanilinyl, 1,2-benzodioxol-5-yl, 4-(morpholinylsulfonyl)-phenyl, and 4-(pyrrolidinylsulfonyl)-phenyl.

In some embodiments, when $L^1$ is a $C_4$ alkylene bridge, $R_1$ is not a group selected from (9H-xanthan-9-yl)methyl, (phenylmethyl)thiomethyl, 3-oxo-3-methoxy-propyl, 2,2-dimethyl-N-(1,2,3,4-tetrahydro-8-dibenzofuranyl)-ethanamidyl, 3-chlorobenzo[b]thiophen-2-yl, 2-methoxy-4-(methylthio)-phenyl, cyclohexyl, 3-(trifluoromethyl)phenyl, adamantan-1-yl-amino, 3-chloroanilinyl, 1,2-benzodioxol-5-yl, 4-(morpholinylsulfonyl)-phenyl, 4-(dimethylaminosulfonylamino)-cyclohex-1-yl, and 4-(pyrrolidinylsulfonyl)-phenyl; wherein each is optionally substituted with 1, 2, 3, or 4 independently selected $R^5$ groups.

In some embodiments, when $L^1$ is a $C_4$ alkylene bridge, $R_1$ is not selected from a heterocycloalkylalkyl group containing an aromatic ring fused to the non-aromatic cyclic hydrocarbon moiety. In some embodiments, when $L^1$ is a $C_4$ alkylene bridge, $R_1$ is not selected from $C_{13-15}$ heterocycloalkylalkyl. In some embodiments, when $L^1$ is a $C_4$ alkylene bridge, $R_1$ is not selected from $C_{1-4}$ heterocycloalkylalkyl. In some embodiments, when $L^1$ is a $C_4$ alkylene bridge, $R_1$ is not selected from $C_{13}$-$C_{15}$ heterocycloalkylalkyl. In some embodiments, when $L^1$ is a $C_4$ alkylene bridge, $R_1$ is not selected from (9H-xanthan-9-yl)methyl which is optionally substituted with 1 or 2 $R^5$ groups. In some embodiments, when $L^1$ is a $C_4$ alkylene bridge, $R_1$ is not selected from (9H-xanthan-9-yl)methyl.

In some embodiments, $R_1$ is not selected from a heterocycloalkylalkyl group containing an aromatic ring fused to the non-aromatic cyclic hydrocarbon moiety. In some embodiments, $R_1$ is not selected from $C_{13-15}$ heterocycloalkylalkyl. In some embodiments, $R_1$ is not selected from $C_{14}$ heterocycloalkylalkyl. In some embodiments, $R_1$ is not selected from $C_{13}$-$C_{15}$ heterocycloalkylalkyl. In some embodiments, $R_1$ is not selected from (9H-xanthan-9-yl)methyl which is optionally substituted with 1, 2, 3, or 4 independently selected $R^5$ groups. In some embodiments, $R_1$ is not selected from (9H-xanthan-9-yl)methyl.

In some embodiments, when $L^1$ is a $C_4$ alkylene bridge, $R_1$ is not selected from a heterocycloalkyl group containing an aromatic ring fused to the non-aromatic cyclic hydrocarbon moiety. In some embodiments, when $L^1$ is a $C_4$ alkylene bridge, $R_1$ is not selected from a heterocycloalkyl group containing 2 oxygen atoms. In some embodiments, when $L^1$ is a $C_4$ alkylene bridge, $R_1$ is not selected from a 9-membered heterocycloalkyl group containing an aromatic ring fused to the non-aromatic cyclic hydrocarbon moiety. In some embodiments, when $L^1$ is a $C_4$ alkylene bridge, $R_1$ is not selected from 1,2-benzodioxol-5-yl which is optionally substituted with 1, 2, 3, or 4 independently selected $R^5$ groups. In some embodiments, when $L^1$ is a $C_4$ alkylene bridge, $R_1$ is not selected from 1,2-benzodioxol-5-yl.

In some embodiments, $R_1$ is not selected from a heterocycloalkyl group containing an aromatic ring fused to the non-aromatic cyclic hydrocarbon moiety. In some embodiments, $R_1$ is not selected from a heterocycloalkyl group containing 2 oxygen atoms. In some embodiments, $R_1$ is not selected from a 9-membered heterocycloalkyl group containing an aromatic ring fused to the non-aromatic cyclic hydrocarbon moiety. In some embodiments, $R_1$ is not selected from 1,2-benzodioxol-5-yl which is optionally substituted with 1, 2, 3, or 4 independently selected $R^5$ groups. In some embodiments, $R_1$ is not selected from 1,2-benzodioxol-5-yl.

In some embodiments, when $L^1$ is a $C_4$ alkylene bridge, $R^1$ is not selected from cyclohexyl and cyclopentyl which are each optionally substituted with 1, 2, 3, or 4 independently selected $R^5$ groups. In some embodiments, when $L^1$ is a $C_4$ alkylene bridge, $R^1$ is not selected from cyclopentyl or cyclohexyl, each of which is optionally substituted with 1, 2, 3, or 4 independently selected $R^5$ groups. In some embodiments, when $L^1$ is a $C_4$ alkylene bridge, $R^1$ is not selected from cyclopentyl or cyclohexyl, each of which is optionally substituted with 1 $R^5$ group. In some embodiments, when $L^1$ is a $C_4$ alkylene bridge, $R^1$ is not selected from cyclohexyl. In some embodiments, when $L^1$ is a $C_4$ alkylene bridge, $R^1$ is not selected from cyclopentyl or cyclohexyl. In some embodiments, when $L^1$ is a $C_4$ alkylene bridge, $R^1$ is not selected from cycloalkyl which is further optionally substituted. In some embodiments, when $L^1$ is a $C_4$ alkylene bridge, $R^1$ is not selected from $C_4$-$C_7$ cycloalkyl which is further optionally substituted. In some embodiments, when $L^1$ is a $C_4$ alkylene bridge, $R^1$ is not selected from $C_5$-$C_6$ cycloalkyl which is further optionally substituted.

In some embodiments, $R^1$ is not selected from cyclohexyl and cyclopentyl which are each optionally substituted with 1, 2, 3, or 4 independently selected $R^5$ groups. In some embodiments, $R^1$ is not selected from cyclopentyl or cyclohexyl, each of which is optionally substituted with 1, 2, 3, or 4 independently selected $R^5$ groups. In some embodiments, $R^1$ is not selected from cyclopentyl or cyclohexyl, each of which is optionally substituted with 1 $R^5$ group. In some embodiments, $R^1$ is not selected from cyclohexyl. In some embodiments, $R^1$ is not selected from cyclopentyl or cyclohexyl. In some embodiments, $R^1$ is not selected from cycloalkyl which is further optionally substituted. In some embodiments, $R^1$ is not selected from $C_4$-$C_7$ cycloalkyl which is further optionally substituted In some embodiments, $R^1$ is not selected from $C_5$-$C_6$ cycloalkyl which is further optionally substituted.

In some embodiments, when $L^1$ is a $C_4$ alkylene bridge, $R^1$ is not selected from a 9-membered heteroaryl ring having 1 heteroatom selected from sulfur. In some embodiments, when $L^1$ is a $C_4$ alkylene bridge, $R^1$ is not selected from a 9-membered heteroaryl ring having 1 heteroatom selected from sulfur; wherein said 9-membered heteroaryl ring is optionally substituted with 1 or 2 $R^5$ groups. In some embodiments, when $L^1$ is a $C_4$ alkylene bridge, $R^1$ is not selected from benzo[b]thiophen-2-yl which is optionally substituted with 1 or 2 $R^5$ groups. In some embodiments, when $L^1$ is a $C_4$ alkylene bridge, $R^1$ is not selected from benzo[b]thiophen-2-yl which is optionally substituted with 1 chloro group. In some embodiments, when $L^1$ is a $C_4$ alkylene bridge, $R^1$ is not selected from 3-chlorobenzo[b]thiophen-2-yl.

In some embodiments, $R^1$ is not selected from a 9-membered heteroaryl ring having 1 heteroatom selected from sulfur. In some embodiments, $R^1$ is not selected from a 9-membered heteroaryl ring having 1 heteroatom selected from sulfur; wherein said 9-membered heteroaryl ring is optionally substituted with 1 or 2 $R^5$ groups. In some embodiments, $R^1$ is not selected from benzo[b]thiophen-2-yl which is optionally substituted with 1 or 2 $R^5$ groups. In some embodiments, $R^1$ is not selected from benzo[b]thiophen-2-yl which is optionally substituted with 1 chloro group. In some embodiments, $R^1$ is not selected from 3-chlorobenzo[b]thiophen-2-yl.

In some embodiments, when $L^1$ is a $C_4$ alkylene bridge, then $R^1$ is not selected from phenyl substituted with 1 to 2 groups selected from methoxy, methylthio, trifluoromethyl, morpholin-4-yl-sulfonyl, and pyrrolidin-2-yl; wherein said phenyl is further optionally substituted. In some embodiments, $R^1$ is not selected from phenyl substituted with 1 to 2 groups selected from methoxy, methylthio, trifluoromethyl, morpholin-4-yl-sulfonyl, and pyrrolidin-2-yl; wherein said phenyl is further optionally substituted.

In some embodiments, when $L^1$ is a $C_4$ alkylene bridge and $R^1$ is phenyl substituted with 1, 2, 3, or 4 independently selected $R^5$ groups, then $R^5$ is not selected from $OR^a$ and $SR^a$; wherein $R^1$ is selected from $C_{1-6}$ alkyl. In some embodiments, when $L^1$ is a $C_4$ alkylene bridge and $R^1$ is phenyl substituted with 1, 2, 3, or 4 independently selected $R^5$ groups, then $R^5$ is not selected from $OR^a$ and $SR^a$; wherein $R^1$ is selected from $C_{1-6}$ alkyl, which is optionally substituted with 1, 2, or 3 independently selected $R^g$ groups. In some embodiments, when $L^1$ is a $C_4$ alkylene bridge and $R^1$ is phenyl substituted with 1, 2, 3, or 4 independently selected $R^5$ groups, then $R^5$ is not selected from $OR^a$ and $SR^a$; wherein $R^1$ is selected from $C_{1-3}$ alkyl. In some embodiments, when $L^1$ is a $C_4$ alkylene bridge and $R^1$ is phenyl substituted with 1, 2, 3, or 4 independently selected $R^5$ groups, then $R^5$ is not selected from methylthio and methoxy.

In some embodiments, when $R^1$ is phenyl substituted with 1, 2, 3, or 4 independently selected $R^5$ groups, then $R^5$ is not selected from $OR^a$ and $SR^a$; wherein $R^a$ is selected from $C_{1-6}$ alkyl. In some embodiments, when $R^1$ is phenyl substituted with 1, 2, 3, or 4 independently selected $R^g$ groups, then $R^5$ is not selected from $OR^a$ and $SR^a$; wherein $R^a$ is selected from $C_{1-6}$ alkyl, which is optionally substituted with 1, 2, or 3 independently selected $R^g$ groups. In some embodiments, when $R^1$ is phenyl substituted with 1, 2, 3, or 4 independently selected $R^5$ groups, then $R^5$ is not selected from $OR^a$ and $SR^a$; wherein $R^a$ is selected from $C_{1-3}$ alkyl. In some embodiments, when $R^1$ is phenyl substituted with 1, 2, 3, or 4 independently selected $R^5$ groups, then $R^5$ is not selected from methylthio and methoxy.

In some embodiments, when $L^1$ is a $C_4$ alkylene bridge and $R^1$ is phenyl substituted with 1, 2, 3, or 4 independently selected $R^5$ groups, then $R^5$ is not selected from $C_{1-6}$ haloalkyl and $C_{1-6}$ alkyl substituted with 1, 2, 3, or 4 independently selected $R^8$ groups selected from halogen. In some embodiments, when $L^1$ is a $C_4$ alkylene bridge and $R^1$ is phenyl substituted with 1, 2, 3, or 4 independently selected $R^5$ groups, then $R^5$ is not selected from $C_{1-3}$ haloalkyl and $C_{1-6}$ alkyl, wherein said $C_{1-6}$ alkyl is substituted with 1, 2, 3, or 4 independently selected $R^8$ groups selected from halogen. In some embodiments, $L^1$ is a $C_4$ alkylene bridge and $R^1$ is phenyl substituted with 1, 2, 3, or 4 independently selected $R^8$ groups, then $R^5$ is not selected from trifluromethyl. In some embodiments, $L^1$ is a $C_4$ alkylene bridge, then $R^5$ is not selected from $C_{1-6}$ haloalkyl and $C_{1-6}$ alkyl, wherein said $C_{1-6}$ alkyl is substituted with 1, 2, 3, or 4 independently selected $R^8$ groups selected from halogen. In some embodiments, $L^1$ is a $C_4$ alkylene bridge, then $R^5$ is not selected from $C_{1-3}$ haloalkyl and $C_{1-6}$ alkyl, wherein said $C_{1-6}$ alkyl is substituted with 1, 2, 3, or 4 independently selected groups selected from halogen.

In some embodiments, when $R^1$ is phenyl substituted with 1, 2, 3, or 4 independently selected $R^5$ groups, then $R^5$ is not selected from $C_{1-6}$ haloalkyl and $C_{1-6}$ alkyl, wherein said $C_{1-6}$ alkyl is substituted with 1, 2, 3, or 4 independently selected $R^8$ groups selected from halogen. In some embodiments, when $R^1$ is phenyl substituted with 1, 2, 3, or 4 independently selected $R^5$ groups, then $R^5$ is not selected from $C_{1-3}$ haloalkyl and $C_{1-6}$ alkyl, wherein said $C_{1-6}$ alkyl is substituted with 1, 2, 3, or 4 independently selected $R^8$ groups selected from halogen. In some embodiments, when $R^1$ is phenyl substituted with 1, 2, 3, or 4 independently selected $R^5$ groups, then $R^5$ is not selected from trifluromethyl. In some embodiments, $R^5$ is not selected from $C_{1-6}$ haloalkyl and $C_{1-6}$ alkyl, wherein said $C_{1-6}$ alkyl is substituted with 1, 2, 3, or 4 independently selected $R^8$ groups selected from halogen.

In some embodiments, when $L^1$ is a $C_4$ alkylene bridge and $R^1$ is phenyl substituted with 1, 2, 3, or 4 independently selected $R^5$ groups, then $R^5$ is not selected from $S(O)_2R^b$; wherein $R^b$ is heteroaryl. In some embodiments, when $L^1$ is a $C_4$ alkylene bridge and $R^1$ is phenyl substituted with 1, 2, 3, or 4 independently selected $R^5$ groups, then $R^5$ is not selected from $S(O)_2R^b$; wherein $R^b$ is heteroaryl, which is optionally substituted with 1, 2, or 3 independently selected $R^g$ groups. In some embodiments, when $L^1$ is a $C_4$ alkylene bridge and $R^1$ is phenyl substituted with 1, 2, 3, or 4 independently selected $R^5$ groups, then $R^5$ is not selected from $S(O)_2R^b$; wherein $R^b$ is morpholinyl or pyrrolidinyl. In some embodiments, when $L^1$ is a $C_4$ alkylene bridge, then $R^5$ is not selected from $S(O)_2R^b$; wherein $R^b$ is heteroaryl. In some embodiments, when $L^1$ is a $C_4$ alkylene bridge, then $R^5$ is not selected from $S(O)_2R^b$; wherein $R^b$ is heteroaryl substituted with 1, 2, or 3 independently selected $R^g$ groups. In some embodiments, when $L^1$ is a $C_4$ alkylene bridge, then $R^5$ is not selected from $S(O)_2R^b$.

In some embodiments, when $R^1$ is phenyl substituted with 1, 2, 3, or 4 independently selected $R^5$ groups, then $R^5$ is not selected from $S(O)_2R^b$; wherein $R^b$ is heteroaryl. In some embodiments, when $R^1$ is phenyl substituted with 1, 2, 3, or 4 independently selected $R^5$ groups, then $R^5$ is not selected from $S(O)_2R^b$; wherein $R^b$ is heteroaryl, which is optionally substituted with 1, 2, or 3 independently selected $R^g$ groups. In some embodiments, when $R^1$ is phenyl substituted with 1, 2, 3, or 4 independently selected $R^5$ groups, then $R^5$ is not selected from $S(O)_2R^b$; wherein $R^b$ is morpholinyl or pyrrolidinyl. In some embodiments, $R^5$ is not selected from $S(O)_2R^b$; wherein $R^b$ is heteroaryl. In some embodiments, $R^5$ is not selected from $S(O)_2R^b$; wherein $R^b$ is heteroaryl substituted with 1, 2, or 3 independently selected $R^g$ groups. In some embodiments, $R^5$ is not selected from $S(O)_2R^b$.

In some embodiments, when $L^1$ is a $C_4$ alkylene bridge, then $R^1$ is not selected from 2-methoxy-4-(methylthio)-phenyl, 3-(trifluoromethyl)phenyl, 4-(morpholinylsulfonyl)-phenyl, and 4-(pyrrolidinylsulfonyl)-phenyl. In some embodiments, $R^1$ is not selected from 2-methoxy-4-(methylthio)-phenyl, 3-(trifluoromethyl)phenyl, 4-(morpholinylsulfonyl)-phenyl, and 4-(pyrrolidinylsulfonyl)-phenyl.

In some embodiments, when $L^1$ is a $C_4$ alkylene bridge, then $R^1$ is not selected from phenyl which is further optionally substituted. In some embodiments, $R^1$ is not selected from phenyl which is further optionally substituted.

In some embodiments, when $L^1$ is a $C_4$ alkylene bridge and $R^1$ is $C_{1-3}$ alkyl substituted with 1, 2, 3, or 4 independently selected $R^5$ groups, then $R^5$ is not selected from arylalkyl, $C(O)R^b$, and $C(O)NR^eR^f$.

In some embodiments, when $R^1$ is $C_{1-3}$ alkyl substituted with 1, 2, 3, or 4 independently selected $R^5$ groups, then $R^5$ is not selected from arylalkyl, $C(O)R^b$, and $C(O)NR^eR^f$.

In some embodiments, when $L^1$ is a $C_4$ alkylene bridge and $R^1$ is $C_{1-3}$ alkyl substituted with 1, 2, 3, or 4 independently selected $R^5$ groups, then $R^5$ is not selected arylalkyl, $C(O)R^b$, and $C(O)NR^eR^f$; wherein:
  $R^b$ is selected from $C_{1-6}$alkyl;
  $R^e$ is H; and
  $R^f$ is 12- to 14-membered heterocycloalkyl ring; wherein said heterocycloalkyl ring is optionally substituted with 1, 2, or 3 independently selected $R^g$ groups.

In some embodiments, when $R^1$ is $C_{1-3}$ alkyl substituted with 1, 2, 3, or 4 independently selected $R^5$ groups, then $R^5$ is not selected arylalkyl, $C(O)R^b$, and $C(O)NR^eR^f$; wherein:
  $R^b$ is selected from $C_{1-6}$alkyl;
  $R^e$ is H; and
  $R^f$ is 12- to 14-membered heterocycloalkyl ring; wherein said heterocycloalkyl ring is optionally substituted with 1, 2, or 3 independently selected $R^g$ groups.

In some embodiments, when $L^1$ is a $C_4$ alkylene bridge and $R^1$ is $C_{1-3}$ alkyl, then $R^5$ is not selected arylalkyl, $C(O)R^b$, and $C(O)NR^eR^f$; wherein:
  $R^b$ is selected from $C_{1-3}$alkyl;
  $R^e$ is H; and
  $R^f$ is 13-membered heterocycloalkyl ring; wherein said heterocycloalkyl ring is optionally substituted with 1, 2, or 3 independently selected $R^g$ groups.

In some embodiments, $R^1$ is $C_{1-3}$ alkyl substituted with 1, 2, 3, or 4 independently selected $R^5$ groups, then $R^5$ is not selected arylalkyl, $C(O)R^b$, and $C(O)NR^eR^f$; wherein:
  $R^b$ is selected from $C_{1-3}$alkyl;
  $R^e$ is H; and
  $R^f$ is 13-membered heterocycloalkyl ring; wherein said heterocycloalkyl ring is optionally substituted with 1, 2, or 3 independently selected $R^g$ groups.

In some embodiments, when $L^1$ is a $C_4$ alkylene bridge and $R^1$ is $C_{1-6}$ alkyl, then $R^5$ is not selected from $SR^a$; wherein $R^a$ is arylalkyl. In some embodiments, when $L^1$ is a $C_4$ alkylene bridge and $R^1$ is $C_{1-6}$alkyl, then $R^5$ is not selected from $SR^a$; wherein $R^a$ is arylalkyl, which is optionally substituted with 1, 2, or 3 independently selected $R^g$ groups. In some embodiments, when $L^1$ is a $C_4$ alkylene bridge and $R^1$ is $C_{1-6}$ alkyl, then $R^5$ is not selected from $SR^a$; wherein $R^a$ is benzyl. In some embodiments, when $L^1$ is a $C_4$ alkylene bridge and $R^1$ is methyl, then $R^5$ is not selected from $SR^a$. In some embodiments, when $L^1$ is a $C_4$ alkylene bridge and $R^1$ is methyl, then $R^5$ is not selected from $SR^a$; wherein $R^a$ is benzyl.

In some embodiments, when $R^1$ is $C_{1-6}$ alkyl, then $R^5$ is not selected from $SR^a$; wherein $R^a$ is arylalkyl. In some embodiments, when $R^1$ is $C_{1-6}$alkyl, then $R^5$ is not selected from $SR^a$; wherein $R^a$ is arylalkyl, which is optionally substituted with 1, 2, or 3 independently selected $R^g$ groups. In some embodiments, when $R^1$ is $C_{1-6}$ alkyl, then $R^5$ is not selected from $SR^a$; wherein $R^a$ is benzyl. In some embodiments, when $R^1$ is methyl, then $R^5$ is not selected from $SR^a$. In some embodiments, $R^1$ is methyl, then $R^5$ is not selected from $SR^a$; wherein $R^a$ is benzyl.

In some embodiments, when $L^1$ is a $C_4$ alkylene bridge and $R^1$ is $C_{1-12}$ alkyl substituted with 1, 2, 3, or 4 independently selected $R^5$ groups, then $R^5$ is not selected from —$C(O)R^b$. In some embodiments, when $L^1$ is a $C_4$ alkylene bridge and $R^1$ is $C_{1-12}$ alkyl substituted with 1, 2, 3, or 4 independently selected $R^5$ groups, then $R^5$ is not selected from —$C(O)R^b$; wherein $R^b$ is $C_{1-6}$ alkyl. In some embodiments, when $L^1$ is a $C_4$ alkylene bridge and $R^1$ is $C_{1-12}$ alkyl substituted with 1, 2, 3, or 4 independently selected $R^5$ groups, then $R^5$ is not selected from —$C(O)R^b$; wherein $R^b$ is $C_{1-6}$ alkyl which is optionally substituted with 1, 2, or 3 independently selected $R^g$ groups. In some embodiments, when $L^1$ is a $C_4$ alkylene bridge and $R^1$ is $C_{1-12}$ alkyl substituted with 1, 2, 3, or 4 independently selected $R^5$ groups, then $R^5$ is not selected from —$C(O)R^b$; wherein $R^b$ is methyl. In some embodiments, when $L^1$ is a $C_4$ alkylene bridge and $R^1$ is ethyl substituted with 1, 2, 3, or 4 independently selected $R^5$ groups, $R^5$ is not —$C(O)R^b$. In some embodiments, when $L^1$ is a $C_4$ alkylene bridge and $R^1$ is ethyl substituted with 1, 2, 3, or 4 independently selected $R^5$ groups, then $R^5$ is not selected from —$C(O)R^b$; wherein $R^b$ is $C_{1-6}$ alkyl. In some embodiments, when $L^1$ is a $C_4$ alkylene bridge and $R^1$ is ethyl substituted with 1, 2, 3, or 4 independently selected $R^5$ groups, then $R^5$ is not selected from —$C(O)R^b$; wherein $R^b$ is $C_{1-6}$ alkyl which is optionally substituted with 1, 2, or 3 independently selected $R^g$ groups. In some embodiments, when $L^1$ is a $C_4$ alkylene bridge and $R^1$ is ethyl substituted with 1, 2, 3, or 4 independently selected $R^5$ groups, then $R^5$ is not selected from —$C(O)R^b$; wherein $R^b$ is methyl.

In some embodiments, when $R^1$ is $C_{1-12}$ alkyl substituted with 1, 2, 3, or 4 independently selected $R^5$ groups, then $R^5$ is not selected from —$C(O)R^b$. In some embodiments, when $R^1$ is $C_{1-12}$ alkyl substituted with 1, 2, 3, or 4 independently selected $R^5$ groups, then $R^5$ is not selected from —$C(O)R^b$; wherein $R^b$ is $C_{1-6}$ alkyl. In some embodiments, when $R^1$ is $C_{1-12}$ alkyl substituted with 1, 2, 3, or 4 independently selected $R^5$ groups, then $R^5$ is not selected from —$C(O)R^b$;

wherein $R^b$ is $C_{1-6}$ alkyl which is optionally substituted with 1, 2, or 3 independently selected $R^g$ groups. In some embodiments, when $R^1$ is $C_{1-12}$ alkyl substituted with 1, 2, 3, or 4 independently selected $R^5$ groups, then $R^5$ is not selected from selected from —C(O)$R^b$; wherein $R^b$ is methyl. In some embodiments, when $R^1$ is ethyl substituted with 1, 2, 3, or 4 independently selected $R^5$ groups, $R^5$ is not selected from —C(O)$R^b$. In some embodiments, when $R^1$ is ethyl substituted with 1, 2, 3, or 4 independently selected $R^5$ groups, then $R^5$ is not selected from —C(O)$R^b$; wherein $R^b$ is $C_{1-6}$ alkyl. In some embodiments, when $R^1$ is ethyl substituted with 1, 2, 3, or 4 independently selected $R^5$ groups, then $R^5$ is not selected from —C(O)$R^b$; wherein $R^b$ is $C_{1-6}$ alkyl which is optionally substituted with 1, 2, or 3 independently selected $R^g$ groups. In some embodiments, when $R^1$ is ethyl substituted with 1, 2, 3, or 4 independently selected $R^5$ groups, then $R^5$ is not selected from —C(O)$R^b$; wherein $R^b$ is methyl.

In some embodiments, when $L^1$ is a $C_4$ alkylene bridge and $R^1$ is $C_{1-12}$alkyl substituted with 1, 2, 3, or 4 independently selected $R^5$ groups, then $R^5$ is not selected from —C(O)NR$^e$R$^f$. In some embodiments, when $L^1$ is a $C_4$ alkylene bridge and $R^1$ is $C_{1-12}$alkyl substituted with 1, 2, 3, or 4 independently selected $R^5$ groups, then $R^5$ is not selected from —C(O)NR$^e$R$^f$; wherein $R^f$ is heterocycloalkyl. In some embodiments, when $L^1$ is a $C_4$ alkylene bridge and $R^1$ is $C_{1-12}$alkyl substituted with 1, 2, 3, or 4 independently selected $R^5$ groups, then $R^5$ is not selected from —C(O)NR$^e$R$^f$; wherein $R^f$ is heterocycloalkyl which is optionally substituted with 1, 2, or 3 independently selected $R^g$ groups. In some embodiments, when $L^1$ is a $C_4$ alkylene bridge and $R^1$ is $C_{1-12}$ alkyl substituted with 1, 2, 3, or 4 independently selected $R^5$ groups, then $R^5$ is not selected from —C(O)NR$^e$R$^f$; wherein $R^f$ is 13-membered heterocycloalkyl ring. In some embodiments, when $L^1$ is a $C_4$ alkylene bridge and $R^1$ is $C_{1-12}$alkyl substituted with 1, 2, 3, or 4 independently selected $R^5$ groups, then $R^5$ is not selected from —C(O)NR$^e$R$^f$; wherein $R^e$ is H and $R^f$ is 1,2,3,4-tetrahydro-8-dibenzofuranyl. In some embodiments, when $L^1$ is a $C_4$ alkylene bridge and $R^1$ is propyl substituted with 1, 2, 3, or 4 independently selected $R^5$ groups, then $R^5$ is not selected from —C(O)NR$^e$R$^f$; wherein $R^f$ is heterocycloalkyl. In some embodiments, when $L^1$ is a $C_4$ alkylene bridge and $R^1$ is propyl substituted with 1, 2, 3, or 4 independently selected $R^5$ groups, then $R^5$ is not selected from —C(O)NR$^e$R$^f$; wherein $R^f$ is 13-membered heterocycloalkyl ring. In some embodiments, when $L^1$ is a $C_4$ alkylene bridge and $R^1$ is propyl substituted with 1, 2, 3, or 4 independently selected $R^5$ groups, then $R^5$ is not selected from —C(O)NR$^e$R$^f$; wherein $R^f$ is heterocycloalkyl which is optionally substituted with 1, 2, or 3 independently selected $R^g$ groups. In some embodiments, when $L^1$ is a $C_4$ alkylene bridge and $R^1$ is propyl substituted with 1, 2, 3, or 4 independently selected $R^5$ groups, then $R^5$ is not selected from —C(O)NR$^e$R$^f$; wherein $R^e$ is H and $R^f$ is 1,2,3,4-tetrahydro-8-dibenzofuranyl.

In some embodiments, when $R^1$ is $C_{1-12}$ alkyl substituted with 1, 2, 3, or 4 independently selected $R^5$ groups, then $R^5$ is not selected from —C(O)NR$^e$R$^f$. In some embodiments, when $R^1$ is $C_{1-12}$ alkyl substituted with 1, 2, 3, or 4 independently selected $R^5$ groups, then $R^5$ is not selected from —C(O)NR$^e$R$^f$; wherein $R^f$ is heterocycloalkyl. In some embodiments, when $R^1$ is $C_{1-12}$alkyl substituted with 1, 2, 3, or 4 independently selected $R^5$ groups, then $R^5$ is not selected from —C(O)NR$^e$R$^f$; wherein $R^f$ is heterocycloalkyl which is optionally substituted with 1, 2, or 3 independently selected $R^g$ groups. In some embodiments, when $R^1$ is $C_{1-12}$ alkyl substituted with 1, 2, 3, or 4 independently selected $R^5$ groups, then $R^5$ is not selected from —C(O)NR R$^e$; wherein $R^f$ is 13-membered heterocycloalkyl ring. In some embodiments, when $R^1$ is $C_{1-12}$alkyl substituted with 1, 2, 3, or 4 independently selected $R^5$ groups, then $R^5$ is not selected from —C(O)NR$^e$R$^f$; wherein $R^e$ is H and $R^f$ is 1,2,3,4-tetrahydro-8-dibenzofuranyl. In some embodiments, when $R^1$ is propyl substituted with 1, 2, 3, or 4 independently selected $R^5$ groups, then $R^5$ is not selected from —C(O)NR$^e$R$^f$; wherein $R^f$ is heterocycloalkyl. In some embodiments, when $R^1$ is propyl substituted with 1, 2, 3, or 4 independently selected $R^5$ groups, then $R^5$ is not selected from —C(O)NR$^e$R$^f$; wherein $R^f$ is 13-membered heterocycloalkyl ring. In some embodiments, when $R^1$ is propyl substituted with 1, 2, 3, or 4 independently selected $R^5$ groups, then $R^5$ is not selected from —C(O)NR$^e$R$^f$; wherein $R^f$ is heterocycloalkyl which is optionally substituted with 1, 2, or 3 independently selected $R^g$ groups. In some embodiments, when $R^1$ is propyl substituted with 1, 2, 3, or 4 independently selected $R^5$ groups, then $R^5$ is not selected from —C(O)NR$^e$R$^f$; wherein $R^e$ is H and $R^f$ is 1,2,3,4-tetrahydro-8-dibenzofuranyl.

In some embodiments, when $L^1$ is a $C_4$ alkylene bridge, $R^1$ is not selected from NR$^3$R$^4$. In some embodiments, when $L^1$ is a $C_4$ alkylene bridge and $R^1$ is NR$^3$R$^4$, then $R^3$ is not a group selected from cycloalkyl and aryl; wherein said cycloalkyl and aryl are each optionally substituted with 1, 2, 3, or 4 independently selected $R^7$ groups. In some embodiments, when $L^1$ is a $C_4$ alkylene bridge, then $R^1$ is not selected from adamantan-1-yl-amino and 3-chloroanilinyl; wherein said adamantan-1-yl-amino and 3-chloroanilinyl are each optionally substituted with 1, 2, 3, or 4 independently selected $R^7$ groups.

In some embodiments, $R^1$ is not selected from NR$^3$R$^4$. In some embodiments, when $R^1$ is NR$^3$R$^4$, then $R^3$ is not a group selected from cycloalkyl and aryl; wherein said cycloalkyl and aryl are each optionally substituted with 1, 2, 3, or 4 independently selected $R^7$ groups. In some embodiments, $R^1$ is not selected from adamantan-1-yl-amino and 3-chloroanilinyl; wherein said adamantan-1-yl-amino and 3-chloroanilinyl are each optionally substituted with 1, 2, 3, or 4 independently selected $R^7$ groups.

In some embodiments, when $L^1$ is a $C_4$ alkylene bridge substituted by $C_{1-6}$ alkyl which is further substituted by 1, 2, or 3 independently selected $R^6$ groups, then $R^6$ is not selected from alkyloxycarbonyl. In some embodiments, when $L^1$ is a $C_4$ alkylene bridge substituted by $C_{1-6}$ alkyl which is further substituted by 1, 2, or 3 independently selected $R^6$ groups, then $R^6$ is not selected from alkyloxycarbonyl and carboxy. In some embodiments, $R^6$ is not selected from alkyloxycarbonyl and carboxy.

In some embodiments, when $L^1$ is a $C_5$ alkylene bridge and $R^1$ is cyclohexane which is further substituted by 1, 2, or 3 independently selected $R^6$ groups, then $R^5$ is not selected from NR$^b$S(O)$_2$NR$^e$R$^f$. In some embodiments, $R^5$ is not selected from NR$^b$S(O)$_2$NR$^e$R$^f$.

In some embodiments, the compound is not selected from N-(6,7,8,9-tetrahydro-dibenzofuran-2-yl)-acetamide; 2,2,2-trifluoro-N-(6,7,8,9-tetrahydro-dibenzofuran-2-yl)-acetamide; 2-ethoxy-N-(6,7,8,9-tetrahydro-dibenzofuran-2-yl)-acetamide; 3-(6,7,8,9-tetrahydro-dibenzofuran-2-ylcarbamoyl)-acrylic acid; 3-phenyl-N-(6,7,8,9-tetrahydro-dibenzofuran-2-yl)-acrylamide; 3-(4-chloro-phenyl)-N-(6,7,8,9-tetrahydro-dibenzofuran-2-yl)-acrylamide; N-(7,8,9,10-tetrahydro-6H-benzo[b]-cyclohepta[d]furan-2-yl) acetamide; and N-(6,7,8,9,10,11-hexahydrobenzo[b] cycloocta[d]furan-2-yl)acetamide; or pharmaceutically acceptable salt thereof.

In some embodiments, $R^1$ is not $C_{2-12}$ alkenyl or arylalkylene, which are each optionally substituted by 1, 2, 3, or 4 independently selected $R^5$ groups.

In some embodiments, the compound is:

2,2-Dimethyl-N-(6,7,8,9-tetrahydro-dibenzofuran-2-yl)-propionamide;
3-Methyl-N-(6,7,8,9-tetrahydro-dibenzofuran-2-yl)-butyramide;
3,3-Dimethyl-N-(6,7,8,9-tetrahydro-dibenzofuran-2-yl)-butyramide;
2-Phenyl-N-(6,7,8,9-tetrahydro-dibenzofuran-2-yl)-acetamide;
Adamantane-1-carboxylic acid (6,7,8,9-tetrahydro-dibenzofuran-2-yl)-amide;
4-tert-Butyl-N-(6,7,8,9-tetrahydro-dibenzofuran-2-yl)-benzamide;
2-Cyclohexyl-N-(6,7,8,9-tetrahydro-dibenzofuran-2-yl)-acetamide;
N-(6,7,8,9-Tetrahydro-dibenzofuran-2-yl)-propionamide;
N-(6,7,8,9-Tetrahydro-dibenzofuran-2-yl)-isobutyramide;
N-(6,7,8,9-Tetrahydro-dibenzofuran-2-yl)-butyramide;
N-(6,7,8,9-Tetrahydro-dibenzofuran-2-yl)-acetamide;
2-Methyl-N-(6,7,8,9-tetrahydro-dibenzofuran-2-yl)-benzamide;
4-Methoxy-N-(6,7,8,9-tetrahydro-dibenzofuran-2-yl)-benzamide;
4-Methyl-N-(6,7,8,9-tetrahydro-dibenzofuran-2-yl)-pentanamide;
4-Nitro-N-(6,7,8,9-tetrahydro-dibenzofuran-2-yl)-benzamide;
4-Amino-N-(6,7,8,9-tetrahydro-dibenzofuran-2-yl)-benzamide;
4-Chloro-N-(6,7,8,9-tetrahydro-dibenzofuran-2-yl)-benzamide;
N-(6,7,8,9-Tetrahydro-dibenzofuran-2-yl)-benzamide;
4-Fluoro-N-(6,7,8,9-tetrahydrodibenzo[b,d]furan-2-yl)benzamide;
3-Phenyl-N-(6,7,8,9-tetrahydrodibenzo[b,d]furan-2-yl)propanamide;
N-(6,7,8,9-Tetrahydrodibenzo[b,d]furan-2-yl)hexanamide;
N-(2,3-Dihydro-1H-cyclopenta[b]benzofuran-7-yl)-3,3-dimethyl-butyramide;
N-(2,3-Dihydro-1H-cyclopenta(b)benzofuran-7-yl)-2,2-dimethyl-propionamide;
N-(2,3-Dihydro-1H-cyclopenta[b]benzofuran-7-yl)-3-methyl-butyramide;
3,3-Dimethyl-N-[7,8,9,10-tetrahydro-6H-benzo[b]-cyclohepta[d]furan-2-yl]butyramide;
12,2-Dimethyl-N-(6,7,8,9-tetrahydro-5H-10-oxa-benzo[a]azulen-3-yl)-propionamide;
3-Methyl-N-[7,8,9,10-tetrahydro-6H-benzo[b]-cyclohepta[d]furan-2-yl]butyramide;
2-Cyclohexyl-N-[7,8,9,10-tetrahydro-6H-benzo[b]-cyclohepta[d]furan-2-yl]acetamide;
2-(4-Fluorophenyl)-N-(7,8,9,10-tetrahydro-6H-benzo[b]cyclohepta[d]furan-2-yl)acetamide;
N-(7,8,9,10-Tetrahydro-6H-benzo[b]cyclohepta[d]furan-2-yl)pentanamide;
Ethyl 4-oxo-4-(7,8,9,10-tetrahydro-6H-benzo[b]cyclohepta[d]furan-2-ylamino)butanoate;
4-tert-Butyl-N-(7,8,9,10-tetrahydro-6H-benzo[b]cyclohepta[d]furan-2-yl)benzamide;
N-(7,8,9,10-Tetrahydro-6H-benzo[b]cyclohepta[d]furan-2-yl)propanamide;
N-(7,8,9, 10-Tetrahydro-6H-benzo[b]cyclohepta[d]furan-2-yl)hexanamide;
3-Phenyl-N-(7,8,9,10-tetrahydro-6H-benzo[b]cyclohepta[d]furan-2-yl)propanamide;
N-(7,8,9,10-Tetrahydro-6H-benzo[b]cyclohepta[d]furan-2-yl)-2-thien-2-ylacetamide;
N-7,8,9,10-Tetrahydro-6H-benzo[b]cyclohepta[d]furan-2-yl-4-(trifluoromethyl)benzamide;
2-Chloro-N-7,8,9,10-tetrahydro-6H-benzo[b]cyclohepta[d]furan-2-ylacetamide;
2-Morpholin-4-yl-N-7,8,9,10-tetrahydro-6H-benzo[b]cyclohepta[d]furan-2-ylacetamide;
$N^2$-[2-(Dimethylamino)ethyl]-$N^2$-methyl-$N^1$-7,8,9,10-tetrahydro-6H-benzo[b]cyclohepta[d]furan-2-ylglycinamide;
$N^2$-Methyl-$N^2$-(2-pyridin-2-ylethyl)-$N^1$-7,8,9,10-tetrahydro-6H-benzo[b]cyclohepta[d]furan-2-ylglycinamide;
2-(1,4-Dioxa-8-azaspiro[4.5]dec-8-yl)-N-7,8,9,10-tetrahydro-6H-benzo[b]cyclohepta[d]furan-2-ylacetamide;
2-(4-Methylpiperazin-1-yl)-N-7,8,9,10-tetrahydro-6H-benzo[b]cyclohepta[d]furan-2-ylacetamide;
2-(2-Hydroxyethoxy)-N-7,8,9,10-tetrahydro-6H-benzo[b]cyclohepta[d]furan-2-ylacetamide;
$N^2$-Ethyl-$N^2$-methyl-$N^1$-7,8,9,10-tetrahydro-6H-benzo[b]cyclohepta[d]furan-2-ylglycinamide;
$N^2$-(2-Hydroxyethyl)-$N^2$-methyl-$N^1$-7,8,9,10-tetrahydro-6H-benzo[b]cyclohepta[d]furan-2-ylglycinamide;
2-tert-Butoxy-N-7,8,9,10-tetrahydro-6H-benzo[b]cyclohepta[d]furan-2-ylacetamide;
Benzyl [(1S)-1-methyl-2-oxo-2-(7,8,9,10-tetrahydro-6H-benzo[b]cyclohepta[d]furan-2-ylamino)ethyl]carbamate;
2-(4-Pyrimidin-2-ylpiperazin-1-yl)-N-7,8,9,10-tetrahydro-6H-benzo[b]cyclohepta[d]furan-2-ylacetamide;
tert-Butyl [2-oxo-2-(7,8,9,10-tetrahydro-6H-benzo[b]cyclohepta[d]furan-2-ylamino)ethyl]carbamate;
$N^1$-7,8,9,10-Tetrahydro-6H-benzo[b]cyclohepta[d]furan-2-ylglycinamide;
tert-Butyl [(1S)-1-benzyl-2-oxo-2-(7,8,9,10-tetrahydro-6H-benzo[b]cyclohepta[d]furan-2-ylamino)ethyl]carbamate;
tert-Butyl (2S)-2-[(7,8,9,10-tetrahydro-6H-benzo[b]cyclohepta[d]furan-2-ylamino)carbonyl]pyrrolidine-1-carboxylate;
tert-Butyl [(1S)-2-oxo-1-(pyridin-4-ylmethyl)-2-(7,8,9,10-tetrahydro-6H-benzo[b]cyclohepta[d]furan-2-ylamino)ethyl]carbamate;
tert-Butyl [(1S)-1-methyl-2-oxo-2-(7,8,9,10-tetrahydro-6H-benzo[b]cyclohepta[d]furan-2-ylamino)ethyl]carbamate;
N-7,8,9,10-Tetrahydro-6H-benzo[b]cyclohepta[d]furan-2-yl-L-prolinamide;
N-[(Benzyloxy)carbonyl]-L-phenylalanyl-N'-7,8,9,10-tetrahydro-6H-benzo[b]cyclohepta[d]furan-2-yl-L-alaninamide;
tert-Butyl {(1R,2R)-2-(benzyloxy)-1-[(7,8,9,10-tetrahydro-6H-benzo[b]cyclohepta[d]furan-2-ylamino)carbonyl]propyl}carbamate;
1-Acetyl-N-7,8,9,10-tetrahydro-6H-benzo[b]cyclohepta[d]furan-2-yl-L-prolinamide;
1-methyl-N-7,8,9,10-tetrahydro-6H-benzo[b]cyclohepta[d]furan-2-yl-L-prolinamide;
3,3-Dimethyl-N-[6,7,8,9,10,11-hexahydro-benzo[b]-cycloocta[d]furan-2-yl]butyramide;
2,2-Dimethyl-N-[6,7,8,9,10,11-hexahydro-benzo[b]-cycloocta[d]-furan-2-yl]propionamide;

3-Methyl-N-[6,7,8,9,10,11-hexahydro-benzo[b]-cycloocta[d]-furan-2-yl]butyramide;
2-Cyclohexyl-N-[6,7,8,9,10,11-hexahydro-benzo[b]-cycloocta[d]furan-2-yl]acetamide;
N-(6,7,8,9,10,11-Hexahydrobenzo[b]cycloocta[d]furan-2-yl)-3,5,5-trimethylhexanamide;
N-(6,7,8,9,10,11-Hexahydrobenzo[b]cycloocta[d]furan-2-yl)thiophene-2-carboxamide;
4-tert-Butyl-N-(6,7,8,9,10,11-hexahydrobenzo[b]cycloocta[d]furan-2-yl)benzamide;
N-(6,7,8,9,10,11-Hexahydrobenzo[b]cycloocta[d]furan-2-yl)-3-methylbenzamide;
3-Cyclopentyl-N-(6,7,8,9,10,11-hexahydrobenzo[b]cycloocta[d]furan-2-yl)propanamide;
N-(6,7,8,9,10,11-Hexahydrobenzo[b]cycloocta[d]furan-2-yl)hexanamide;
N-(6,7,8,9,10,11-Hexahydrobenzo[b]cycloocta[d]furan-2-yl)-3-phenylpropanamide;
N-(6,7,8,9,10,11-Hexahydrobenzo[b]cycloocta[d]furan-2-yl)acetamide;
N-(6,7,8,9,10,11-Hexahydrobenzo[b]cycloocta[d]furan-2-yl)-2-furamide;
N-(6,7,8,9,10,11-Hexahydrobenzo[b]cycloocta[d]furan-2-yl)-2-phenylacetamide;
N-(6,7,8,9,10,11-Hexahydrobenzo[b]cycloocta[d]furan-2-yl)-2,6-dimethoxybenzamide;
N-(6,7,8,9,10,11-Hexahydrobenzo[b]cycloocta[d]furan-2-yl)isonicotinamide;
N-(6,7,8,9,10,11-Hexahydrobenzo[b]cycloocta[d]furan-2-yl)-2-pyridin-4-ylacetamide;
2-Chloro-N-6,7,8,9,10,11-hexahydrobenzo[b]cycloocta[d]furan-2-ylacetamide;
N-6,7,8,9,10,11-Hexahydrobenzo[b]cycloocta[d]furan-2-yl-2-hydroxyacetamide;
N-6,7,8,9,10,11-Hexahydrobenzo[b]cycloocta[d]furan-2-ylpentanamide; or
N-6,7,8,9,10,11-Hexahydrobenzo[b]cycloocta[d]furan-2-ylheptanamide;

or pharmaceutically acceptable salt thereof.

In some embodiments, the compound is:
1-tert-butyl-3-(6,7,8,9-tetrahydro-dibenzofuran-2-yl)-urea;
1,1-diethyl-3-(6,7,8,9-tetrahydro-dibenzofuran-2-yl)-urea;
ethyl 7,8,9,10-tetrahydro-6H-benzo[b]cyclohepta[d]furan-2-ylcarbamate;
N-(6,7,8,9,10,11-hexahydrobenzo[b]cycloocta[d]furan-2-yl)morpholine-4-carboxamide;
N'-(6,7,8,9,10,11-hexahydrobenzo[b]cycloocta[d]furan-2-yl)-N,N-dimethylurea; or
isopropyl 6,7,8,9,10,11-hexahydrobenzo[b]cycloocta[d]furan-2-ylcarbamate;

or pharmaceutically acceptable salt thereof.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

It is further appreciated that certain features of the invention, which are, for clarity, described in the context of separate embodiments, can also be provided in combination in a single embodiment. Conversely, various features of the invention which are, for brevity, described in the context of a single embodiments, can also be provided separately or in any suitable subcombination.

The term "n-membered" where n is an integer typically describes the number of ring-forming atoms in a moiety where the number of ring-forming atoms is n. For example, piperidinyl is an example of a 6-membered heterocycloalkyl ring and 1,2,3,4-tetrahydro-naphthalene is an example of a 10-membered cycloalkyl group.

For compounds of the invention in which a variable appears more than once, each variable can be a different moiety independently selected from the group defining the variable. For example, where a structure is described having two R groups that are simultaneously present on the same compound, the two R groups can represent different moieties independently selected from the group defined for R.

As used herein, the phrase "optionally substituted" means unsubstituted or substituted. As used herein, the term "substituted" means that a hydrogen atom is removed and replaced by a substitutent. As used herein, the phrase "substituted with oxo" means that two hydrogen atoms are removed from a carbon atom and replaced by an oxygen bound by a double bond to the carbon atom. It is understood that substitution at a given atom is limited by valency.

As used herein, the term "acyl", employed alone or in combination with other terms, refers to a group of formula —C(O)-alkyl, wherein said alkyl group has 1 to 6 carbons.

As used herein, the term "alkyl", employed alone or in combination with other terms, refers to a saturated hydrocarbon group that may be straight-chain or branched. In some embodiments, the alkyl group contains 1 to 12, 1 to 8, or 1 to 6 carbon atoms. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, n-heptyl, n-octyl, and the like. In some embodiments, the alkyl moiety is methyl, ethyl, n-propyl, isopropyl, n-butyl, isobutyl, tert-butyl, n-pentyl, isopentyl, neopentyl, n-hexyl, or 2,4,4-trimethylpentyl.

As used herein, the term "alkylamino" refers to a group of formula —NH(alkyl), wherein the alkylene group and alkyl group each have 1 to 6 carbons.

As used herein, the term "alkylcarbamyl" refers to a group of formula —C(O)—NH(alkyl), wherein the alkyl group has 1 to 6 carbons.

As used herein, the term "alkylcarbamyloxy" refers to a group of formula —OC(O)NH(alkyl), wherein the alkyl group has 1 to 6 carbons.

As used herein, the term "alkylene" refers to a divalent alkyl linking group. Examples of alkylene groups include, but are not limited to, ethan-1,2-diyl, propan-1,3-diyl, propan-1,2-diyl, butan-1,4-diyl, butan-1,3-diyl, butan-1,2-diyl, 2-methyl-propan-1,3-diyl, and the like.

As used herein, the term "alkylene bridge" refers to a straight-chain divalent alkyl linking group.

As used herein, "alkenyl", employed alone or in combination with other terms, refers to an alkyl group having one or more double carbon-carbon bonds. In some embodiments, the alkenyl moiety contains 2 to 10 or 2 to 6 carbon atoms. Example alkenyl groups include, but are not limited to, ethenyl, n-propenyl, isopropenyl, n-butenyl, sec-butenyl, and the like.

As used herein, the term "alkenylene", employed alone or in combination with other terms, refers to a divalent alkenyl group. In some embodiments, the alkenylene moiety contains 2 to 12 carbon atoms. In some embodiments, the alkenylene moiety contains 2 to 6 carbon atoms. Example alkenylene groups include, but are not limited to, ethen-1,2-diyl, propen-1,3-diyl, propen-1,2-diyl, buten-1,4-diyl, buten-1,3-diyl, buten-1,2-diyl, 2-methyl-propen-1,3-diyl, and the like.

As used herein, "alkynyl", employed alone or in combination with other terms, refers to an alkyl group having one or more triple carbon-carbon bonds. Example alkynyl groups include, but are not limited to, ethynyl, propyn-1-yl, propyn-2-yl, and the like. In some embodiments, the alkynyl moiety contains 2 to 10 or 2 to 6 carbon atoms.

As used herein, the term "alkynylene", employed alone or in combination with other terms, refers to a divalent alkynyl group. In some embodiments, the alkynylene moiety contains 2 to 12 carbon atoms. In some embodiments, the alkynylene moiety contains 2 to 6 carbon atoms. Example alkynylene groups include, but are not limited to, ethyn-1,2-diyl, propyn-1,3,-diyl, 1-butyn-1,4-diyl, 1-butyn-1,3-diyl, 2-butyn-1,4-diyl, and the like.

As used herein, the term "alkoxy", employed alone or in combination with other terms, refers to an group of formula —O-alkyl. Example alkoxy groups include methoxy, ethoxy, propoxy (e.g., n-propoxy and isopropoxy), t-butoxy, and the like.

As used herein, the term "alkyloxycarbonyl" refers to a group of formula —C(O)O-alkyl, wherein the alkyl group has 1 to 6 carbon atoms.

As used herein, the term "alkylsulfinyl" refers to a group of formula —S(O)-alkyl, wherein the alkyl group has 1 to 6 carbons.

As used herein, the term "alkylsulfonyl" refers to a group of formula —S(O)$_2$-alkyl, wherein the alkyl group has 1 to 6 carbons.

As used herein, the term "alkylthio" refers to a group of formula —S-alkyl, wherein the alkyl group has 1 to 6 carbon atoms.

As used herein, the term "amino", employed alone or in combination with other terms, refers to a group of formula —NH$_2$.

As used herein, the term "aryl", employed alone or in combination with other terms, refers to a monocyclic or polycyclic (e.g., having 2, 3 or 4 fused or covalently linked rings) aromatic hydrocarbon moiety, such as, but not limited to, phenyl, 1-naphthyl, 2-naphthyl, anthracenyl, phenanthrenyl, and the like. In some embodiments, aryl groups have from 6 to 20 carbon atoms, about 6 to 10 carbon atoms, or about 6 to 8 carbons atoms.

As used herein, the term "arylalkyl" refers to a group of formula -alkylene-aryl. In some embodiments, the alkyl portion of the arylalkyl group has 1 to 6 carbon atoms. In some embodiments, the alkyl portion of the arylalkyl group is methyl. In some embodiments, the arylalkyl group is benzyl.

As used herein, the term "arylalkenyl" refers to a group of formula -alkenylene-aryl.

As used herein, the term "arylalkynyl" refers to a group of formula -alkynylene-aryl.

As used herein, the term "aryloxy" refers to a group of formula —O-aryl.

As used herein, the term "carbamyl" refers to a group of formula —C(O)NH$_2$.

As used herein, the term "carbonyl", employed alone or in combination with other terms, refers to a —C(O)— group, which is a divalent one-carbon moiety further bonded to an oxygen atom with a double bond.

As used herein, the term "carboxy" refers to a group of formula —C(O)OH.

As used herein, the term "cycloalkyl", employed alone or in combination with other terms, refers to a non-aromatic cyclic hydrocarbon moiety, which may optionally contain one or more alkenylene or alkynylene groups as part of the ring structure. Cycloalkyl groups can include mono- or polycyclic (e.g., having 2, 3 or 4 fused or covalently linked rings) ring systems. Also included in the definition of cycloalkyl are moieties that have one or more aromatic rings fused (i.e., having a bond in common with) to the cycloalkyl ring, for example, benzo derivatives of pentane, pentene, hexane, and the like. The term "cycloalkyl" also includes bridgehead cycloalkyl groups and spirocycloalkyl groups. As used herein, "bridgehead cycloalkyl groups" refers to non-aromatic cyclic hydrocarbon moieties containing at least one bridgehead carbon, such as admantan-1-yl. As used herein, "spirocycloalkyl groups" refers to non-aromatic hydrocarbon moieties containing at least two rings fused at a single carbon atom, such as spiro[2.5]octane and the like. In some embodiments, the cycloalkyl group has 3 to 14 ring members, 3 to 10 ring members, or 3 to 8 ring members. One or more ring-forming carbon atoms of a cycloalkyl group can be oxidized to form carbonyl linkages. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. In some embodiments, the cycloalkyl group is admanatan-1-yl.

As used herein, the term "cycloalkylalkyl" refers to a group of formula -alkylene-cycloalkyl. In some embodiments, the alkyl portion of the cycloalkylalkyl group has 1 to 6 carbon atoms. In some embodiments, the alkyl portion of the cycloalkylalkyl group has 1 to 2 carbons. In some embodiments, the cycloalkylalkyl group is cyclohexylmethyl or cyclopentylethyl.

As used herein, the term "cycloalkylalkenyl" refers to a group of formula -alkenylene-cycloalkyl.

As used herein, the term "cycloalkylalkynyl" refers to a group of formula -alkynylene-cycloalkyl.

As used herein, the term "cycloalkyloxy" refers to a group of formula —O-cycloalkyl.

As used herein, the term "cyano" refers to a group of formula —CN, wherein the carbon and nitrogen atoms are bound together by a triple bond.

As used herein, the term "dialkylamino" refers to a group of formula —N(alkyl)$_2$, wherein the alkylene group and two alkyl groups each has, independently, 1 to 6 carbons.

As used herein, the term "dialkylcarbamyl" refers to a group of formula —C(O)—N(alkyl)$_2$, wherein the alkyl groups each has, independently, 1 to 6 carbons.

As used herein, the term "dialkylcarbamyloxyl" refers to a group of formula —OC(O)N(alkyl)$_2$, wherein the alkyl groups each has, independently, 1 to 6 carbon atoms.

As used herein, the term "formyl", employed alone or in combination with other terms, refers to a group of formula —C(O)—H.

As used herein, "haloalkoxy", employed alone or in combination with other terms, refers to a group of formula —O-haloalkyl. An example haloalkoxy group is OCF$_3$.

As used herein, the term "haloalkyl", employed alone or in combination with other terms, refers to an alkyl group having from one halogen atom to 2n+1 halogen atoms which may be the same or different, where "n" is the number of carbon atoms in the alkyl group.

As used herein, the terms "halo" and "halogen", employed alone or in combination with other terms, refer to fluoro, chloro, bromo, and iodo.

As used herein, the term "heteroaryl", "heteroaryl ring", or "heteroaryl group", employed alone or in combination with other terms, refers to a monocyclic or polycyclic (e.g., having 2, 3 or 4 fused or covalently linked rings) aromatic hydrocarbon moiety, having one or more heteroatom ring members selected from nitrogen, sulfur and oxygen. When the heteroaryl group contains more than one heteroatom ring member, the heteroatoms may be the same or different. Example heteroaryl groups include, but are not limited to, pyrrolyl, azolyl, oxazolyl, thiazolyl, imidazolyl, furyl, thienyl, quinolinyl, isoquinolinyl, indolyl, benzothienyl, benzofuranyl, benzisoxazolyl, imidazo[1,2-b]thiazolyl or the like. In some embodiments, the heteroaryl group has 5 to 10 carbon atoms.

As used herein, the term "heteroarylalkyl" refers to a group of formula -alkylene-heteroaryl. In some embodiments, the alkyl portion of the heteroaryl group has 1 to 6 carbon atoms.

As used herein, the term "heteroarylalkenyl" refers to a group of formula -alkenylene-heteroaryl.

As used herein, the term "heteroarylalkynyl" refers to a group of formula -alkynylene-heteroaryl.

As used herein, the term "heteroaryloxy" refers to a group of formula —O-heteroaryl.

As used herein, the term "heterocycloalkyl", "heterocycloalkyl ring", or "heterocycloalkyl group", employed alone or in combination with other terms, refers to non-aromatic ring system, which may optionally contain one or more alkenylene or alkynylene groups as part of the ring structure, and which has at least one heteroatom ring member selected from nitrogen, sulfur and oxygen. When the heterocycloalkyl groups contains more than one heteroatom, the heteroatoms may be the same or different. Heterocycloalkyl groups can include mono- or polycyclic (e.g., having 2, 3 or 4 fused or covalently bonded rings) ring systems. Also included in the definition of heterocycloalkyl are moieties that have one or more aromatic rings fused (i.e., having a bond in common with) to the non-aromatic ring, for example, 1,2,3,4-tetrahydro-quinoline and the like. Heterocycloalkyl groups can also include bridgehead heterocycloalkyl groups and spiroheterocycloalkyl groups. As used herein, "bridgehead heterocycloalkyl group" refers to a heterocycloalkyl moiety containing at least one bridgehead atom, such as azaadmantan-1-yl and the like. As used herein, "spiroheterocycloalkyl group" refers to a heterocycloalkyl moiety containing at least two rings fused at a single atom, such as [1,4-dioxa-8-aza-spiro[4.5]decan-N-yl] and the like. In some embodiments, the heterocycloalkyl group has 3 to 20 ring-forming atoms, 3 to 10 ring-forming atoms, or about 3 to 8 ring forming atoms. The carbon atoms or hetereoatoms in the ring(s) of the heterocycloalkyl group can be oxidized to form a carbonyl, or sulfonyl group (or other oxidized linkage) or a nitrogen atom can be quaternized.

As used herein, the term "heterocycloalkylalkyl" refers to a group of formula -alkyl-heterocycloalkyl. In some embodiments, the alkyl portion of the heterocycloalkylalkyl group has 1 to 6 carbon atoms. In some embodiments, the alkyl portion of the heterocycloalkylalkyl group is methylene. In some embodiments, the heterocycloalkylalkyl group is (tetrahydrofur-2-yl)methyl.

As used herein, the term "heterocycloalkylalkenyl" refers to a group of formula -alkenylene-heterocycloalkyl.

As used herein, the term "heterocycloalkylalkynyl" refers to a group of formula -alkynylene-heterocycloalkyl.

As used herein, the term "heterocycloalkyloxy" refers to a group of formula —O-heterocycloalkyl.

As used herein, the term "hydroxyl" refers to a group of formula —OH.

As used herein, the term "nitro" refers to a group of formula —NO$_2$.

As used herein, the term "sulfinyl", employed alone or in combination with other terms, refers to —S(O)— group, which is a divalent one-sulfur moiety further bonded to an oxygen atom with a double bond.

As used herein, the term "sulfonyl", employed alone or in combination with other terms, refers to a —S(O)$_2$— group, which is a divalent one-sulfur moiety further bonded to two oxygen atoms via double bonds.

As used herein, the term "thio", employed alone or in combination with other terms, refers to a —S— group, which is a divalent one-sulfur moiety.

The compounds in this invention may contain one or more asymmetric centers, which can thus give rise to optical isomers (enantiomers) and diastereomers. While shown without respect to the stereochemistry in Formula I, the present invention includes such optical isomers (enantiomers) and diastereomers (geometric isomers); as well as the racemic and resolved, enantiomerically pure R and S stereoisomers; as well as other mixtures of the R and S stereoisomers and pharmaceutically acceptable salts thereof. The use of these compounds is intended to cover the racemic mixture or either of the chiral enantiomers.

Optical isomers can be obtained in pure form by standard procedures known to those skilled in the art, and include, but are not limited to, diastereomeric salt formation, kinetic resolution, and asymmetric synthesis. See, for example, Jacques, et al., Enantiomers, Racemates and Resolutions (Wiley Interscience, New York, 1981); Wilen, S. H., et al., Tetrahedron 33:2725 (1977); Eliel, E. L. Stereochemistry of Carbon Compounds (McGraw-Hill, N.Y., 1962); Wilen, S. H. Tables of Resolving Agents and Optical Resolutions p. 268 (E. L. Eliel, Ed., Univ. of Notre Dame Press, Notre Dame, Ind. 1972), each of which is incorporated herein by reference in their entireties. It is also understood that this invention encompasses all possible regioisomers, and mixtures thereof, which can be obtained in pure form by standard separation procedures known to those skilled in the art, and include, but are not limited to, column chromatography, thin-layer chromatography, and high-performance liquid chromatography.

One skilled in the art will also recognize that it is possible for tautomers to exist for the compounds of the present invention. The present invention includes all such tautomers even though not shown in the formulas herein.

Compounds of the invention can also include all isotopes of atoms occurring in the intermediates or final compounds. Isotopes include those atoms having the same atomic number but different mass numbers. For example, isotopes of hydrogen include tritium and deuterium.

The compounds of the present invention also include pharmaceutically acceptable salts of the compounds disclosed herein. As used herein, the term "pharmaceutically acceptable salt" refers to a salt formed by the addition of a pharmaceutically acceptable acid or base to a compound disclosed herein. As used herein, the phrase "pharmaceutically acceptable" refers to a substance that is acceptable for use in pharmaceutical applications from a toxicological perspective and does not adversely interact with the active ingredient. Pharmaceutically acceptable salts, including mono- and bi- salts, include, but are not limited to, those derived from organic and inorganic acids such as, but not limited to, acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, and similarly known acceptable acids. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in their entireties.

In some embodiments, the compounds of Formula I are prodrugs. As used herein, "prodrug" refers to a moiety that releases a compound of the invention when administered to a patient. Prodrugs can be prepared by modifying functional groups present in the compounds in such a way that the modifications are cleaved, either in routine manipulation or in vivo, to the parent compounds. Examples of prodrugs include compounds of the invention as described herein that contain one or more molecular moieties appended to a hydroxyl, amino, sulfhydryl, or carboxyl group of the compound, and that when administered to a patient, cleaves in vivo to form the free hydroxyl, amino, sulfhydryl, or carboxyl group, respectively. Examples of prodrugs include, but are not limited to, acetate, formate and benzoate derivatives of alcohol and amine functional groups in the compounds of the invention. Preparation and use of prodrugs is discussed in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are incorporated herein by reference in their entireties.

Pharmaceutical Compositions, Methods and Uses

The compounds of Formula I, and embodiments thereof, are useful in treating disorders treatable by potassium channel modulators. Disorders that are treatable by potassium channel modulators includes those disorders whose symptomatology, progression, development, and/or pathology affected by the potassium channel modulation. These disorders include, but are not limited to, cardiovascular diseases; central nervous system disorders; and urinary incontinence.

As used herein, the term "central nervous system disorder" refers to a disorder associated with the nervous system of a patient, including, but not limited to the brain, spinal cord, and nerves. As used herein, the term "cardiovascular disease" refers to a disorder, injury, or disease that detrimentally affects the heart or blood vessels.

In some embodiments, the present invention provides a method of treating ischemic heart disease, myocardial infarction, cardiac arrhythmia, hypertension, or angina pectoris in an individual in need thereof, comprising administering to said individual a therapeutically effective amount of a compound of Formula I.

In some embodiments, the present invention provides a method of treating epilepsy, episodic ataxia type 1, paroxysmal dyskinesia, neurodegenerative spincerebrallar ataxia, Parkinson's disease, Alzheimer's disease, or multiple sclerosis in an individual in need of treatment thereof, comprising administering to said individual a therapeutically effective amount of a compound of Formula I.

In some embodiments, the present invention provides a method of treating depression, generalized anxiety disorder, bulimia nervosa, or anorexia nervosa in an individual in need thereof, comprising administering to said individual a therapeutically effective amount of a compound of Formula I.

In some embodiments, the present invention provides a method of treating type I diabetes or type II diabetes in an individual in need thereof, comprising administering to said individual a therapeutically effective amount of a compound of Formula I.

In some embodiments, the present invention provides a method of treating allergy or asthma in an individual in need thereof, comprising administering to said individual a therapeutically effective amount of a compound of Formula I.

In some embodiments, the present invention provides a method of treating urinary incontinence, irritable bowel syndrome, or irritable bladder syndrome in an individual in need thereof, comprising administering to said individual a therapeutically effective amount of a compound of Formula I.

In some embodiments, the present invention provides a method of treating pain or inflammation in an individual in need thereof, comprising administering to said individual a therapeutically effective amount of a compound of Formula I.

In some embodiments, the present invention provides a method of modulating a potassium channel in an individual in need thereof, comprising administering to said individual a therapeutically effective amount of a compound of Formula I.

The methods may utilize all of the embodiments for the compounds of Formula I hereinbefore described, including various combinations and subcombinations of the embodiments.

The present invention further provides a use of a compound of Formula I, or pharmaceutically acceptable salt thereof, for the production of medicament for use in the treatment of disorders remedied or alleviated by potassium channel modulation.

In some embodiments, the present invention provides a use of a compound of Formula I, or pharmaceutically acceptable salt thereof, for the production of medicament for use in the treatment of ischemic heart disease, myocardial infarction, cardiac arrhythmia, hypertension, or angina pectoris.

In some embodiments, the present invention provides a use of a compound of Formula I, or pharmaceutically acceptable salt thereof, for the production of medicament for use in the treatment of epilepsy, episodic ataxia type 1, paroxysmal dyskinesia, neurodegenerative spincerebrallar ataxia, Parkinson's disease, Alzheimer's disease, or multiple sclerosis.

In some embodiments, the present invention provides a use of a compound of Formula I, or pharmaceutically acceptable salt thereof, for the production of medicament for use in the treatment of depression, generalized anxiety disorder, bulimia nervosa, or anorexia nervosa, In some embodiments, the present invention provides a use of a compound of Formula I, or pharmaceutically acceptable salt thereof, for the production of medicament for use in the treatment of type I diabetes or type II diabetes.

In some embodiments, the present invention provides a use of a corn pound of Formula I, or pharmaceutically acceptable salt thereof, for the production of medicament for use in the treatment of allergy or asthma.

In some embodiments, the present invention provides a use of a corn pound of Formula I, or pharmaceutically acceptable salt thereof, for the production of medicament for use in the treatment of urinary incontinence, irritable bowel syndrome, or irritable bladder syndrome.

In some embodiments, the present invention provides a use of a corn pound of Formula I, or pharmaceutically acceptable salt thereof, for the production of medicament for use in the treatment of pain or inflammation.

The uses may utilize all of the embodiments for the compounds of Formula I hereinbefore described, including various combinations and subcombinations of the embodiments.

The present invention further provides a compound of Formula I, or pharmaceutically acceptable salt thereof, for use in a method of treatment of disorders remedied or alleviated by potassium channel modulation.

In some embodiments, the present invention provides a compound of Formula I, or pharmaceutically acceptable salt thereof, for use in a method of treatment of ischemic heart disease, myocardial infarction, cardiac arrhythmia, hypertension, or angina pectoris by therapy.

In some embodiments, the present invention provides a compound of Formula I, or pharmaceutically acceptable salt thereof, for use in a method of treatment of epilepsy, episodic ataxia type 1, paroxysmal dyskinesia, neurodegenerative spincerebrallar ataxia, Parkinson's disease, Alzheimer's disease, or multiple sclerosis by therapy.

In some embodiments, the present invention provides a compound of Formula I, or pharmaceutically acceptable salt thereof, for use in a method of treatment of depression, generalized anxiety disorder, bulimia nervosa, or anorexia nervosa by therapy.

In some embodiments, the present invention provides a compound of Formula I, or pharmaceutically acceptable salt thereof, for use in a method of treatment of type I diabetes or type II diabetes by therapy.

In some embodiments, the present invention provides a compound of Formula I, or pharmaceutically acceptable salt thereof, for use in a method of treatment of allergy or asthma by therapy.

In some embodiments, the present invention provides a compound of Formula I, or pharmaceutically acceptable salt thereof, for use in a method of treatment of urinary incontinence, irritable bowel syndrome, or irritable bladder syndrome by therapy.

In some embodiments, the present invention provides a compound of Formula I, or pharmaceutically acceptable salt thereof, for use in a method of treatment of pain or inflammation by therapy.

The compounds for use in method of treatment can include all of the embodiments for the compounds of Formula I hereinbefore described, including various combinations and subcombinations of the embodiments.

As used herein, the term "individual" refers to any animal, including mammals, preferably mice, rats, other rodents, rabbits, dogs, cats, swine, cattle, sheep, horses, or primates, and most preferably humans. In some embodiments, the individual is an adult, child, or infant. In some embodiments, the individual is a mammal. In some embodiments, the individual is a human.

The phrase "therapeutically effective amount" refers to the amount of a compound of the invention that elicits the biological or medicinal response in a tissue, system, animal, individual, patient, or human that is being sought by a researcher, veterinarian, medical doctor or other clinician. The desired biological or medicinal response may include preventing the disorder in an individual (e.g., preventing the disorder in an individual that may be predisposed to the disorder, but does not yet experience or display the pathology or symptomatology of the disease). The desired biological or medicinal response may also include inhibiting the disorder in an individual that is experiencing or displaying the pathology or symptomatology of the disorder (i.e., arresting or slowing further development of the pathology and/or symptomatology). The desired biological or medicinal response may also include ameliorating the disorder in an individual that is experiencing or displaying the pathology or symptomatology of the disease (i.e., reversing the pathology or symptomatology).

The therapeutically effective amount provided in the treatment of a specific disorder will vary depending the specific disorder(s) being treated, the size, age, and response pattern of the individual the severity of the disorder(s), the judgment of the attending clinician, the manner of administration, and the purpose of the administration, such as prophylaxis or therapy. In general, effective amounts for daily oral administration may be about 0.01 to 50 mg/kg, preferably about 0.1 to 10 mg/kg and effective amounts for parenteral administration may be about 0.01 to 10 mg/kg, preferably about 0.1 to 5 mg/kg.

The compounds of the invention may be administered orally or parenterally, neat or in combination with one or more conventional pharmaceutically acceptable carriers or excipients. Accordingly, the present invention provides a pharmaceutical composition which comprises a compound of Formula I, or a pharmaceutically salt thereof, and a pharmaceutically acceptable carrier. The pharmaceutical compositions can include all of the embodiments for the compounds of Formula I hereinbefore described, including various combinations and subcombinations of the embodiments.

Solid carriers suitable for use in the compositions of the invention include one or more substances which may also act as flavoring agents, lubricants, solubilizers, suspending agents, fillers, glidants, compression aides, binders, tablet-disintegrating agents or encapsulating materials. In powders, the carrier may be a finely divided solid which is in admixture with a finely divided active ingredient. As used herein, the term "active ingredient" refers to a compound of Formula I, or a pharmaceutically acceptable salt thereof. In tablets, the active ingredient may be mixed with a carrier having the necessary compression properties in suitable proportions and compacted in the shape and size desired. The powders and tablets may contain up to 99% by weight of the active ingredient. Solid carriers suitable for use in the composition of the invention include calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Any pharmaceutically acceptable liquid carrier suitable for preparing solutions, suspensions, emulsions, syrups and elixirs may be employed in the compositions of the invention. The active ingredient may be dissolved or suspended in a pharmaceutically acceptable liquid carrier such as water, an organic solvent, or a pharmaceutically acceptable oil or fat, or a mixture thereof. The liquid composition may contain other suitable pharmaceutical additives such as solubilizers, emulsifiers, buffers, preservatives, sweeteners, flavoring agents, suspending agents, thickening agents, coloring agents, viscosity regulators, stabilizers, osmo-regulators, or the like. Suitable examples of liquid carriers for oral and parenteral administration include water (particularly containing additives as above, e.g., cellulose derivatives, preferably sodium carboxymethyl cellulose solution), alcohols (including monohydric alcohols and polyhydric alcohols, e.g., glycols) or their derivatives, or oils (e.g., fractionated coconut oil and arachis oil). For parenteral administration the carrier may also be an oily ester such as ethyl oleate or isopropyl myristate. Sterile liquid carriers can be used in sterile liquid form compositions for parenteral administration. The liquid carrier for pressurized compositions can be halogenated hydrocarbon or other pharmaceutically acceptable propellant.

Compositions of the invention which are sterile solutions or suspensions are suitable for intramuscular, intraperitoneal or subcutaneous injection. Sterile solutions may also be administered intravenously. Inventive compositions suitable for oral administration may be in either liquid or solid composition form.

The compounds of the invention can be administered rectally or vaginally in the form of a conventional suppository. For administration by intranasal or intrabronchial inhalation or insufflation, the compounds of the present invention can be formulated into an aqueous or partially aqueous solution, which can then be utilized in the form of an aerosol. The compounds of the present invention can also be administered transdermally through the use of a transdermal patch containing the active compound and a carrier that is inert to the active compound, is non-toxic to the skin, and allows delivery of the agent for systemic absorption into the blood stream via the skin. The carrier can take any number of forms such as creams and ointments, pastes, gels, and occlusive devices. The creams and ointments can be viscous liquid or semisolid emulsions of either the oil-in-water or water-in-oil type. Pastes comprised of absorptive powders dispersed in petroleum or hydrophilic petroleum containing the active ingredient can also be suitable. A variety of occlusive devices can be used to release the active ingredient into the blood stream such as a semipermeable membrane covering a reservoir containing the active ingredient with or without a carrier, or a matrix containing the active ingredient. Other occlusive devices are known in the literature.

The pharmaceutical composition can be administered in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

In some embodiments of the methods, uses, and compositions herein, the compounds of Formula I, or pharmaceutically acceptable salts thereof, are administered as prodrugs as described herein.

Syntheses and Processes

The compounds of the present invention can be prepared in a variety of ways known to one skilled in the art of organic synthesis. The compounds of the present invention can be synthesized using the methods as hereinafter described below, together with synthetic methods known in the art of synthetic organic chemistry or variations thereon as appreciated by those skilled in the art.

The compounds of present invention can be conveniently prepared in accordance with the procedures outlined in the schemes below, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures. Those skilled in the art of organic synthesis will recognize that the nature and order of the synthetic steps presented may be varied for the purpose of optimizing the formation of the compounds of the invention.

The processes described herein can be monitored according to any suitable method known in the art. For example, product formation can be monitored by spectroscopic means, such as nuclear magnetic resonance spectroscopy (e.g., $^1$H or $^{13}$C NMR) infrared spectroscopy, spectrophotometry (e.g., UV-visible), or mass spectrometry, or by chromatography such as high performance liquid chromatography (HPLC) or thin layer chromatography.

Preparation of compounds can involve the protection and deprotection of various chemical groups. The need for protection and deprotection, and the selection of appropriate protecting groups can be readily determined by one skilled in the art. The chemistry of protecting groups can be found, for example, in Greene, et al., Protective Groups in Organic Synthesis, 2d. Ed., Wiley & Sons, 1991, which is incorporated herein by reference in its entirety.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

The compounds of Formula I can be produced as shown in Schemes 1, 2, or 3. In Scheme 1, step (a), a cycloalkanone oxime of Formula II, such as cyclohexanone oxime or cycloheptanone oxime, is treated with a base, such as potassium tert-butoxide, in a suitable solvent, such as DMF, to generate the oxime alkoxide which, in step (b), is then mixed with a para-halo substituted nitrobenzene of Formula III (X is halogen), such as 4-fluoronitrobenzene or 4-chloronitrobenzene, to generate the O-nitrophenyl oxime of Formula IV. In step (c), the O-nitrophenyl oxime of Formula IV is treated with an acid, such as aqueous hydrochloric acid, in a suitable solvent, such as isopropanol, and then heated to 80-120° C. to provide the nitro-benzofuran of Formula V. In step (d), the nitro-benzofuran of Formula V can be reduced by hydrogenolysis in the presence of a metal catalyst, such as palladium on carbon or Raney nickel, in a suitable solvent, such as ethanol, to give the amino-benzofuran of Formula VI. In step (e), the amino-benzofuran of Formula VI can be treated with an acylating agent of Formula VII (Y is halogen, $C_{1-12}$ alkoxy, hydroxyl, amino, OC(O)R$^{3y}$, or OC(O)R$_1$; and R$^{3y}$ is $C_{1-12}$ alkyl) to provide the target amido-benzofuran of Formula I. For example, the amino-benzofuran of Formula VI can be treated with an acylating agent, such as an acid chloride, in the presence of base, such as triethylamine or pyridine, in a suitable solvent, such dichloromethane or acetonitrile. Alternatively, the amino-benzofuran of Formula VI can be treated with a carboxylic acid in the presence of coupling reagents, such as 1-(3-dimethylaminopropyl)-3-ethylcarbodiimide and N-hydroxybenzotriazole, and a base, such as triethylamine or diisopropylethylamine, in a suitable solvent, such as dichloromethane, to provide the target amido-benzofuran of Formula I. Similarly, urea-benzofurans and carbamate-benzofurans, wherein R$^1$ is NR$^3$R$^4$ or OR$^2$, respectively, can be formed by treatment of the amino-benzofuran of Formula VI with a carbamoyl halide or haloformate of formula R$^1$—C(O)-halogen. Further, urea-benzofurans, wherein R$^1$ is NR$^3$R$^4$ and R$^3$ is H, can be formed by treatment of the amino-benzofuran of Formula VI with an isocyanate of formula R$^4$—N=C=O. In the cases where R$^1$ contains a protecting group, this protecting group can be removed under known conditions.

Scheme 1

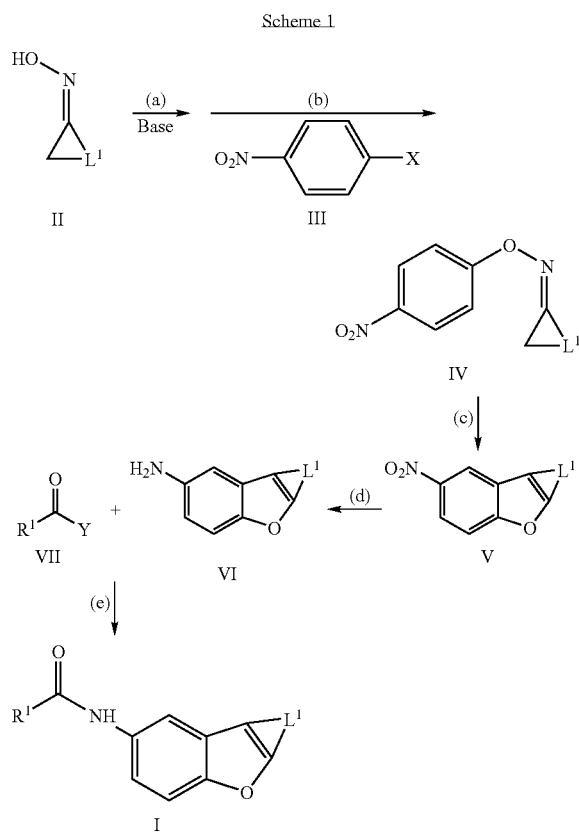

In Scheme 2, step (i), protection of 4-aminophenol of Formula VIII with a suitable protecting group, G, such as dimethylsulfamoyl chloride (G=S(O)$_2$N(CH$_3$)$_2$), in the presence of a base, such as triethylamine, in a suitable solvent, such as tetrahydrofuran, provides the protected aniline-phenol of Formula IX. In step (ii), oxidation of the protected aniline-phenol with a suitable oxidizing agent, such as 2,3-dichloro-5,6-dicyanobenzoquinone, in a suitable solvent, such as dichloromethane, provides the benzoquinoneimine of Formula X. In step (iii), treatment of a suitable β-ketoester of Formula Xi (R$^{10}$ is C$_{1-6}$ alkyl, cycloalkyl, cycloalkylalkyl, heterocycloalkylalkyl, aryl, arylalkyl, heteroaryl, or heteroarylalkyl), such as 2-cyclohexanone carboxylic acid ethyl ester, with a base, such as potassium tert-butoxide or sodium hydride, in a suitable solvent, such as tetrahydrofuran, followed by treatment with the benzoquinoneimine and then an appropriate acid, such as acetic acid, provides the phenolic cycloalkanone of Formula XIIa. In step (iv), treatment of the phenolic cycloalkanone with an acid, such as hydrochloric acid, in a solvent, such as dioxane or acetic acid, provides upon heating at 80-120° C., first the protected amino-benzofuran which upon further heating gives the target amino-benzofuran of Formula VI. As an alternative, in step (v), the benzoquinoneimine of Formula X can be treated at elevated temperatures, such as 60-100° C., with a suitable enamine of Formula XIII (R$^{11}$ and R$^{12}$ are independently selected from C$_{1-6}$ alkyl, cycloalkyl, cycloalkylalkyl, heterocycloalkylalkyl, aryl, arylalkyl, heteroaryl, or heteroarylalkyl), such as 1-(4-morpholino)cyclohexene, in a solvent, such as chloroform, to generate the sulfonamido-benzofuran of Formula XII. In step (iv), cleavage of the sulfonamido-benzofuran is achieved by treating the compound with an acid, such as hydrochloric acid, in a suitable solvent, such as acetic acid, at elevated temperatures, such as 80-120° C., to provide the target amino-benzofuran of Formula VI. Compounds of Formula I can then be produced from the amino-benzofuran of Formula VI by following Scheme 1, step (e).

Scheme 2

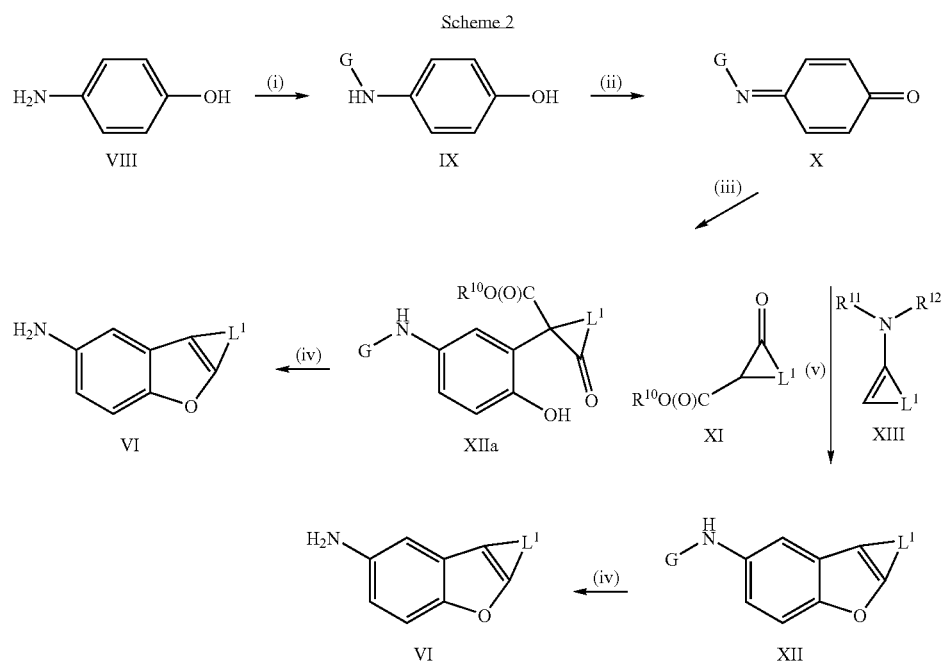

Compounds of Formula I wherein $R^1$ is alkyl substituted with 1 $R^5$ group selected from $NR^eR^f$ or $OR^a$ can be obtained as shown in Scheme 3. Accordingly, in Scheme 3, step (f), treatment of the haloacetyl amido-benzofuran of Formula XIV ($R^{13}$ is $C_{1-12}$alkylene; and Z is halogen), such as chloroacetyl amido-benzofuran, with an amine of formula $HNR^eR^f$ in the presence of a base, such as cesium carbonate, in a suitable solvent, such as acetonitrile, generates the aminoacetyl amido-benzofuran of Formula XV. Alternatively, treatment of the haloacetyl amido-benzofuran of Formula XIV, such as chloroacetyl amido-benzofuran, with an alcohol of formula $HOR^a$ in the presence of a base, such as potassium tert-butoxide, in a suitable solvent, such as dimethylformamide, generates the alkoxyacetyl amido-benzofuran. Alternatively, treatment of the chloroacetyl amido-benzofuran with water in the presence of a base, such cesium carbonate, in a suitable solvent, such as acetonitrile, generates the hydroxyacetyl amido-benzofuran.

Scheme 3

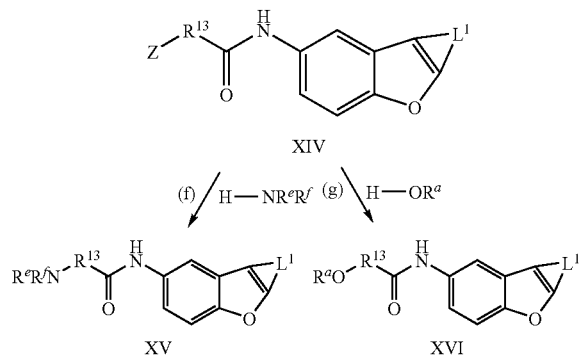

In the cases where $R^1$ in the amido-benzofuran contains a tert-butyl carbamate, the tert-butyl carbamate could be cleaved by standard conditions, such as trifluoroacetic acid in dichloromethane, to generate the free amine. Similarly, in the cases where $R^1$ in the amido-benzofuran contains a benzyl carbamate, the benzyl carbamate could be cleaved by standard conditions, such as hydrogenolysis in the presence of palladium on carbon in ethanol, to generate the free amine.

In accordance with the Schemes herein, the present invention further provides synthetic processes for producing the compounds of Formula I, and embodiments thereof. The synthetic processes of the invention may used to produce any of the embodiments of the compounds of Formula I hereinbefore described. In some embodiments, the synthetic process for producing a compound of Formula I comprises reacting a compound of Formula VI:

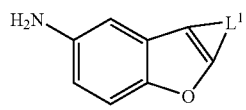

with a compound of Formula VII:

under conditions and for a time sufficient to produce a compound of Formula I;

wherein:

Y is halogen, $C_{1-12}$alkoxy, hydroxyl, amino, $OC(O)R^{yy}$, or $OC(O)R_1$; and $R^{yy}$ is $C_{1-12}$ alkyl.

In some embodiments, the conditions for producing the compound of Formula I from the compounds of Formula VI and VII include a base. In some embodiments, the base is triethylamine or pyridine. In some embodiments, the solvent is dichloromethane or acetonitrile. In some embodiments, the conditions for producing the compound of Formula I from the compounds of Formula VI and VII include a coupling agent. In some embodiments, the coupling agent comprises 1-(3-dimethylaminopropyl)-3-ethylcarbodiimide and N-hydroxybenzotriazole.

In some embodiments, the compound of Formula VI is produced by a process that comprises reducing the nitro group of a compound of Formula V:

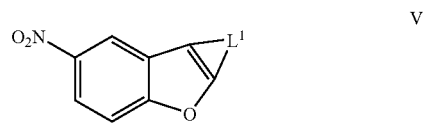

under conditions and for a time sufficient to produce a compound of Formula VI.

In some embodiments, the reducing of the compound of Formula V comprises reacting a compound of Formula V with a reducing agent comprising zinc, tin, iron, lithium aluminum hydride, a sulfide, hot liquid paraffin, aluminum hydride-aluminum chloride, hydrazine, sodium dihydro(trithio)borate, or hydrogen gas.

In some embodiments, the solvent for the reduction is ethanol or isopropanol.

In some embodiments, the compound of Formula V is produced by a process that comprises:

a) reacting a compound of Formula II:

with a base to under conditions and for a time sufficient to form the alkoxide of the compound of Formula II;

b) treating the alkoxide of the compound of Formula II with a compound of Formula III:

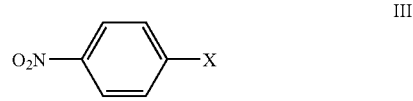

under conditions and for a time sufficient to form a compound of Formula IV:

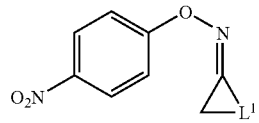

and c) treating the compound of Formula IV with an acid under conditions and for a time sufficient to produce a compound of Formula V;

wherein X is halogen.

In some embodiments, the base in (a) is potassium tert-butoxide, potassium hydroxide, sodium hydroxide, sodium methoxide, sodium tert-butoxide. In some embodiments, the base in (a) is potassium tert-butoxide.

In some embodiments, the solvent for step (a) is dimethylformamide ("DMF").

In some embodiments, X is chloro or fluoro. In some embodiments, X is chloro.

In some embodiments, the acid in (c) is hydrochloric acid, sulfuric acid, phosphoric acid, or nitric acid. In some embodiments, the acid in (c) is hydrochloric acid.

In some embodiments, the solvent for step (c) is isopropanol.

In some embodiments, the conditions for step (c) comprise heating the reaction mixture to a temperature of about 80° C. to about 120° C.

In some embodiments, the compound of Formula VI is produced by a process that comprises reacting a compound of Formula XII:

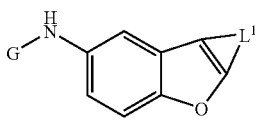

under conditions and for a time sufficient to form a compound of Formula VI;

wherein G is a protecting group.

Suitable protecting groups include, but are not limited to, the protecting groups listed for primary amines in Greene, et al., Protective Groups in Organic Synthesis, 2d. Ed., Wiley & Sons, 1991, which is incorporated herein by reference in its entirety.

In some embodiments, G is $—S(O)_2—R^9$ and $R^9$ is $C_{2-12}$ dialkylamino. In some embodiments, G is $—S(O)_2—R^9$ and $R^9$ is dimethylamino.

In some embodiments, the conditions for the reaction of the compound of Formula XII to form a compound of Formula VI comprise heating the reaction mixture to a temperature of about 80° C. to about 120° C.

In some embodiments, the conditions for the reaction of the compound of Formula XII to form a compound of Formula VI comprise treatment with an acid, such as hydrochloric acid in a solvent, such as dioxane or acetic acid. In some embodiments, the conditions for the reaction of the compound of Formula XII to form a compound of Formula VI comprise treatment with an acid, such as hydrochloric acid in a solvent, such as dioxane or acetic acid; and heating to a temperature of about 80° C. to about 120° C.

In some embodiments, the conditions for the reaction of compound of Formula XII to form a compound of Formula VI comprises treatment with an acid. In some embodiments, the acid is hydrochloric acid, sulfuric acid, phosphoric acid, or nitric acid. In some embodiments, the acid is hydrochloric acid.

In some embodiments, the compound of Formula XII is produced by a process comprising:

a) reacting a compound of Formula IX:

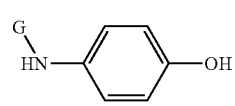

with an oxidizing agent under conditions and for a time sufficient to produce a compound of Formula X:

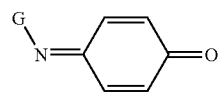

and b) reacting a compound of Formula X with a compound of Formula XIII:

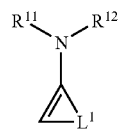

under conditions and for a time sufficient to produce a compound of Formula XII;

wherein:

$R^{11}$ and $R^{12}$ are each, independently, $C_{1-6}$ alkyl, cycloalkyl, cycloalkylalkyl, heterocycloalkylalkyl, aryl, arylalkyl, heteroaryl, or heteroarylalkyl; and G is a protecting group.

In some embodiments, the oxidizing agent in (a) is 2,3-dichloro-5,6-dicyanobenzoquinone.

In some embodiments, the conditions for (b) comprise treatement with an acid. In some embodiments, the acid is hydrochloric acid. In some embodiments, the conditions for (c) comprise heating the reaction mixture to a temperature of about 80° C. to about 120° C.

In some embodiments, $R^{11}$ and $R^{12}$ are each, independently, $C_{1-6}$ alkyl.

In some embodiments, G is $—S(O)_2—R^9$ and $R^9$ is $C_{2-12}$ dialkylamino. In some embodiments, G is $—S(O)_2—R^9$ and $R^9$ is dimethylamino.

In some embodiments, the compound of Formula VI is produced by a process that comprises reacting a compound of Formula XIIa:

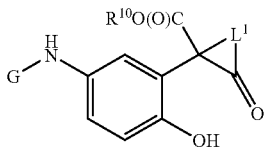

under conditions and for a time sufficient to form a compound of Formula VI;

wherein G is a protecting group.

Suitable protecting groups include, but are not limited to, the protecting groups listed for primary amines in Greene, et al., Protective Groups in Organic Synthesis, 2d. Ed., Wiley & Sons, 1991, which is incorporated herein by reference in its entirety.

In some embodiments, G is —S(O)$_2$—R$^9$ and R$^9$ is C$_{2-12}$ dialkylamino. In some embodiments, G is —S(O)$_2$—R$^9$ and R$^9$ is dimethylamino.

In some embodiments, the conditions for the reaction of the compound of Formula XIIa to form a compound of Formula VI comprise heating the reaction mixture to a temperature of about 80° C. to about 120° C.

In some embodiments, the conditions for the reaction of compound of Formula XIIa to form a compound of Formula VI comprises treatment with an acid. In some embodiments, the acid is hydrochloric acid, sulfuric acid, phosphoric acid, or nitric acid. In some embodiments, the acid is hydrochloric acid.

In some embodiments, the compound of Formula XIIa is produced by a process comprising:

a) reacting a compound of Formula IX:

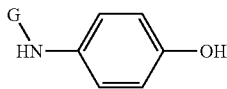

with an oxidizing agent under conditions and for a time sufficient to produce a compound of Formula X:

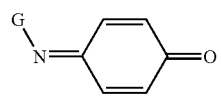

b) reacting a compound of Formula XI:

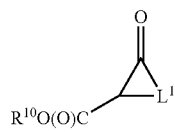

with a base;

c) reacting the compound of Formula X with the reaction mixture of b); under conditions and for a time sufficient to produce a compound of Formula XIIa;

wherein:

R$^{10}$ is C$_{1-6}$ alkyl, cycloalkyl, cycloalkylalkyl, heterocycloalkylalkyl, aryl, arylalkyl, heteroaryl, or heteroarylalkyl; and G is a protecting group.

In some embodiments, R$^{10}$ is C$_{1-6}$ alkyl.

In some embodiments, the oxidizing agent in (a) is 2,3-dichloro-5,6-dicyanobenzoquinone.

In some embodiments, the base in (b) is potassium tert-butoxide or sodium hydride.

In some embodiments, the conditions for (c) comprise treatment with an acid. In some embodiments, the acid is hydrochloric acid. In some embodiments, the conditions for (c) comprise heating the reaction mixture to a temperature of about 80° C. to about 120° C.

In some embodiments, G is —S(O)$_2$—R$^9$ and R$^9$ is C$_{2-12}$ dialkylamino. In some embodiments, G is —S(O)$_2$—R$^9$ and R$^9$ is dimethylamino.

The present invention further comprises a synthetic process for producing a compound of Formula I comprising reacting a compound of Formula XIV:

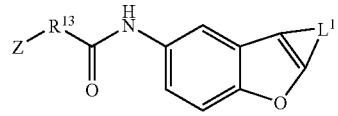

with a compound of formula H—NR$^e$R$^f$ under conditions and for a time sufficient to produce a compound of Formula I;

wherein:
R$^1$ is C$_{1-12}$ alkyl substituted with 1 R$^5$ group;
R$^5$ is NR$^e$R$^f$;
R$^{13}$ is C$_{1-12}$alkylene; and
Z is halogen.

In some embodiments, R$^{13}$ is C$_{1-3}$ alkylene. In some embodiments, R$^{13}$ is C$_{1-2}$ alkylene. In some embodiments, R$^{13}$ is C$_1$ alkylene.

In some embodiments, Z is chloro.

In some embodiments, the conditions comprise treating the reaction mixture with a base. In some embodiments, the base is cesium carbonate. In some embodiments, the conditions comprise a solvent. In some embodiments, the solvent is acetonitrile.

The present invention further provides a synthetic process for producing a compound of Formula I comprising reacting a compound of Formula XIV:

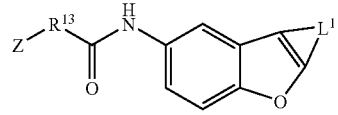

with a compound of formula H—OR$^a$ under conditions and for a time sufficient to produce a compound of Formula I;

wherein:
R$^1$ is C$_{1-12}$ alkyl substituted with 1 R$^5$ group;
R$^5$ is OR$^a$;
R$^{13}$ is C$_{1-12}$alkylene; and
Z is halogen.

In some embodiments, $R^{13}$ is $C_{1-3}$ alkylene. In some embodiments, $R^{13}$ is $C_{1-2}$ alkylene. In some embodiments, $R^{13}$ is $C_1$ alkylene.

In some embodiments, Z is chloro.

In some embodiments, the conditions comprise treating the reaction mixture with a base. In some embodiments, the base is cesium carbonate. In some embodiments, the conditions comprise a solvent. In some embodiments, the solvent is acetonitrile.

The present invention further provides a synthetic process for producing a compound of Formula I, comprising reacting a compound of formula $R^4$—N=C=O with a compound of formula VI:

VI under conditions and for a time sufficient to produce a compound of Formula I;

wherein:

$R^1$ is $NR^3R^4$; and $R^3$ is H.

EXAMPLES

In order that the invention disclosed herein may be more efficiently understood, examples are provided below. It should be understood that these examples are for illustrative purposes only and are not to be construed as limiting the invention in any manner.

The following abbreviations are used herein: "Me" is methyl; "min" is minute(s); "h" is hour(s); "Mp" is melting point; "MS" is mass spectrometry; "ESI" is electron spray ionization.

Preparation 1

6,7,8,9-TETRAHYDRO-DIBENZOFURAN-2-YLAMINE

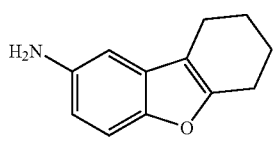

Method A:

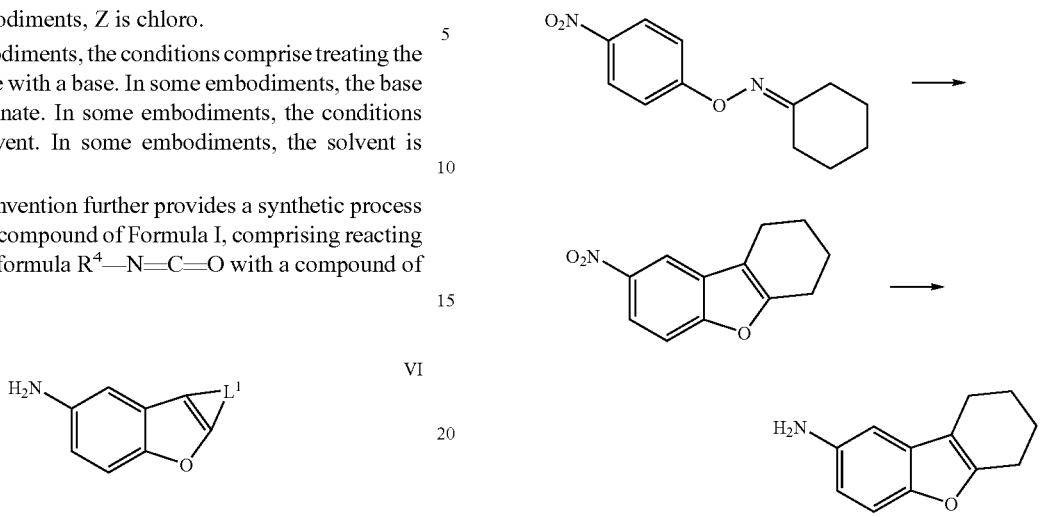

Following method A, potassium t-butoxide (37 g, 320 mmol) was added in portions to a cooled (2° C.) solution of cyclohexanone oxime (35 g, 300 mmol) in DMF (350 mL). The cooled reaction mixture was stirred for 20 minutes and then 1-chloro-4-nitrobenzene (50 g, 320 mmol) was added in portions. The reaction mixture was stirred at ~10° C. for 30 minutes and then allowed to warm to room temperature and stirred for an additional 4 hours. The reaction mixture was concentrated under reduced pressure to remove the DMF and then treated with water (300 mL). The precipitate was collected by filtration and washed with water. Recrystallization of the crude material from isopropanol and column chromatography provided cyclohexanone O-(4-nitro-phenyl)-oxime (48 g). Cyclohexanone O-(4-nitro-phenyl)-oxime (48 g, 205 mmol) was dissolved in warm isopropanol (350 mL) and 12 N hydrochloric acid (94 mL) was added. The reaction mixture was heated to reflux for 3.5 hours and then cooled in an ice bath. The solid was collected by filtration, washed with water and cold isopropanol, and dried in an oven to give 8-nitro-1,2,3,4-tetrahydro-dibenzofuran (33 g, 150 mmol). A mixture of 8-nitro-1,2,3,4-tetrahydro-dibenzofuran (11 g, 50 mmol) and Raney nickel (~11 g wet weight) in ethanol (200 mL) was hydrogenated at 50 PSI on a Parr shaker overnight. The mixture was filtered through Celite® and the filtrate was concentrated. The crude solid was recrystallized from hexane to give 6,7,8,9-tetrahydro-dibenzofuran-2-YLAMINE (7.6 g). Mp 71-72° C.

Method B:

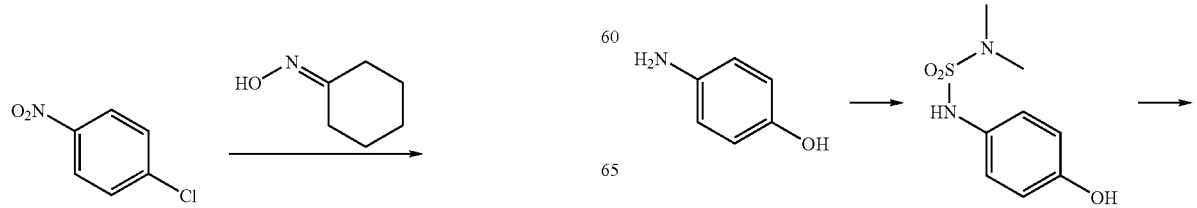

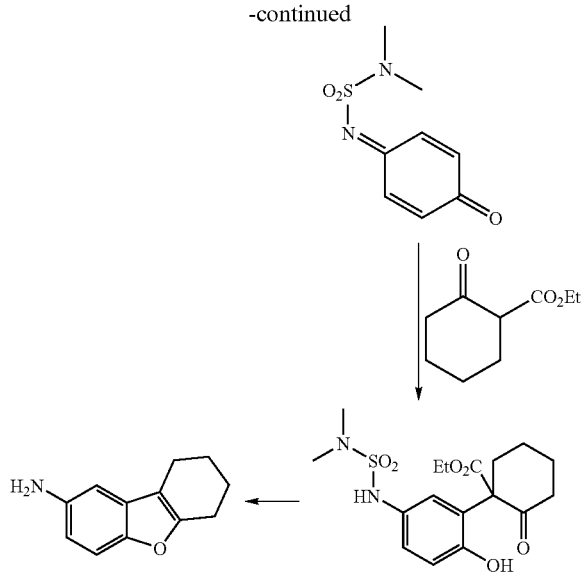

Following method B, dimethylsulfamoyl chloride (60 mL, 550 mmol) was added to a gently refluxing solution of 4-aminophenol (55 g, 500 mmol) and triethylamine (56 g, 550 mmol) in tetrahydrofuran (350 mL). The reaction mixture was refluxed for 2 h and then cooled to room temperature and then filtered to remove the solids. The filtrate was diluted with ethyl acetate and washed with 2 N HCl and brine, dried (Na₂SO₄) and concentrated to give crude N'-(4-hydroxy-phenyl)-N,N-dimethyl-sulfamide (108 g). The crude N'-(4-hydroxy-phenyl)-N,N-dimethyl-sulfamide (108 g, 500 mmol) was dissolved in dichloromethane (750 mL) and 2,3-dichloro-5,6-dicyanobenzoquinone (130 g, 550 mmol) was added. The reaction mixture was stirred for 35 minutes and then filtered. The solids were washed with dichloromethane and the filtrate was concentrated. The crude material was purified by column chromatography to provide the benzoquinoneimine (85 g). Potassium t-butoxide (0.30 g, 2.5 mmol) was added to a cooled (2° C.) solution of 2-cyclohexanonecarboxylic acid ethyl ester (4.2 mL, 25 mmol) in tetrahydrofuran (60 mL). The reaction mixture was stirred at 2° C. for 10 min and then a solution of benzoquinoneimine (5.4 g, 25 mmol) in tetrahydrofuran (45 mL) was added. After 1 hour, the mixture was quenched with glacial acetic acid (0.14 mL) and stirred at 2° C. for 40 min, and then concentrated. The crude material was dissolved in ethyl acetate and washed with brine, dried (Na₂SO₄), and concentrated. The material was purified by flash column chromatography (elution with 30% ethyl acetate-hexane) to provide the desired phenolic cyclohexanone (6.8 g). The phenolic cyclohexanone (0.96 g, 2.5 mmol) was dissolved in dioxane (10 mL) and 6 N hydrochloric acid (10 mL) was added and the mixture was heated to reflux for 2.5 hours. The reaction mixture was diluted with water and made basic with concentrated ammonium hydroxide. The mixture was extracted with ethyl acetate. The combined organic extracts were washed with water and brine, dried (Na₂SO₄) and concentrated. Analytical analysis indicated complete furan formation, but incomplete sulfonyl urea hydrolysis. The crude mixture was dissolved in acetic acid (10 mL) and 6 N HCl (10 mL) was added. The mixture was refluxed for 12 hours. After cooling to room temperature, the reaction mixture was cooled to 0° C. and concentrated ammonium hydroxide was added until basic. The mixture was extracted with ethyl acetate. The combined organic extracts were washed with 20% aqueous ammonium hydroxide and brine, dried (Na₂SO₄) and concentrated. Column chromatography purification provided 6,7,8,9-tetrahydro-dibenzofuran-2-ylamine (74 mg).

Method C:

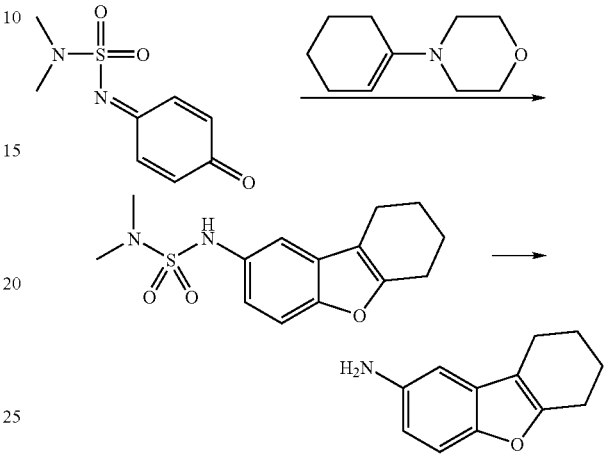

Following method C, the benzoquinoneimine (11 g, 50 mmol) was dissolved in chloroform (130 mL) and 1-(4-morpholino)cyclohexene (9.3 mL, 55 mmol) was added. The reaction mixture was stirred for 40 minutes and then concentrated under reduced pressure. The crude material was dissolved in 2 N HCl (200 mL) and heated to reflux for 35 minutes. After cooling to room temperature, the reaction mixture was cooled in an ice bath and diluted with water (200 mL). The aqueous mixture was extracted with ethyl acetate and the combined extracts were washed with water and brine, dried (NaSO₄), and concentrated. The crude material was purified by flash column chromatography (elution with 20% ethyl acetate-hexane) to provide sulfamoyl tetrahydrodibenzofuran (10 g). The sulfamoyl tetrahydrodibenzofuran (9.5 g, 32 mmol) was dissolved in glacial acetic acid (100 mL) and then 6 N HCl (100 mL) was added. The resulting mixture was heated to reflux for 70 hours. The reaction mixture was then concentrated, diluted with water (200 mL) and made basic with the slow addition of concentrated ammonium hydroxide. The mixture was extracted with ethyl acetate and the combined organic extracts were washed with brine, dried (Na₂SO₄), and concentrated. The crude product was purified by column chromatography (elution with chloroform) to give 6,7,8,9-tetrahydro-dibenzofuran-2-ylamine (5.6 g). Mp 72-73°.

Preparation 2

2,3-DIHYDRO-1H-CYCLOPENTA[B]BENZOFURAN-7-YLAMINE

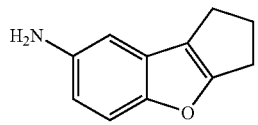

Method A:

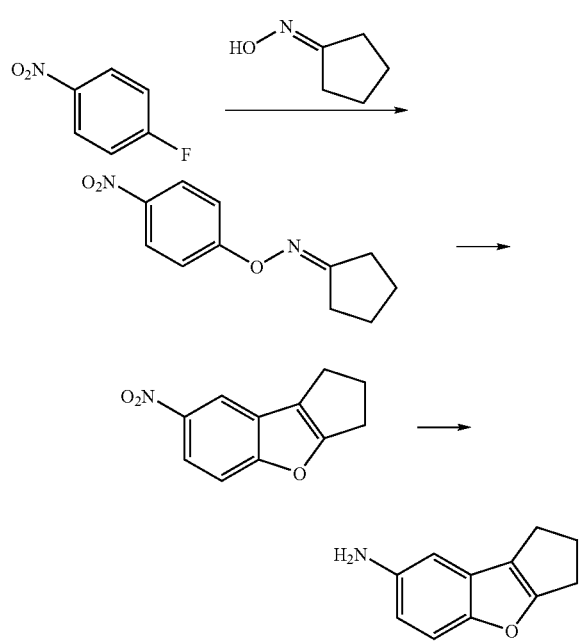

The core molecule was synthesized following method A. Potassium t-butoxide (12 g, 110 mmol) was added in portions to a cooled (0° C.) solution of cyclopentanone oxime (9.9 g, 100 mmol) in DMF (150 mL). The cooled reaction mixture was stirred for 20 minutes and then 1-fluoro-4-nitrobenzene (14 g, 100 mmol) was added in portions. The reaction mixture was stirred at ~10° C. for 30 minutes and then allowed to warm to room temperature and stirred for an additional 4 hours. The reaction mixture was concentrated under reduced pressure to remove the DMF and then treated with water (300 mL). The precipitate was collected by filtration and washed with water to provide cyclopentanone O-(4-nitro-phenyl)-oxime (17 g). Cyclopentanone O-(4-nitro-phenyl)-oxime (14 g, 62 mmol) was dissolved in glacial acetic acid (40 mL) and 1.9 N hydrochloric acid (40 mL) was added. The reaction mixture was stirred at room temperature for 50 minutes and then concentrated. The solid was mixed with water (250 mL) and allowed to stand for 1 hour. The crude mixture was extracted with ethyl acetate and the combined organic phases were dried (Na$_2$SO$_4$) and concentrated. The crude material was dissolved in toluene (350 mL) and p-toluenesulfonic acid (2.0 g, 10 mmol) was added. The reaction mixture was heated to reflux for 4 hours and water was removed with a Dean-Stark trap. The reaction mixture was diluted with ethyl acetate and washed with saturated aqueous sodium bicarbonate and brine. The organic phase was dried (Na$_2$SO$_4$) and concentrated to give 5-nitro-2,3-dihydro-1H-cyclopenta[b]benzofuran (10 g). A mixture of give 5-nitro-2,3-dihydro-1H-cyclopenta[b]benzofuran (5.4 g, 27 mmol) and Raney nickel (~5 g wet weight) in ethanol (50 mL) was hydrogenated at 50 PSI on a Parr shaker for 2 hours. The mixture was filtered through Celite® and the filtrate was concentrated. The crude solid was purified by column chromatography to provide 2,3-dihydro-1H-cyclopenta[b]benzofuran-7-ylamine (4.0 g). Mp 86.5-88.5° C.

Preparation 3

7,8,9,10-TETRAHYDRO-6H-BENZO[B]-CYCLOHEPTA[D]FURAN-2-YLAMINE

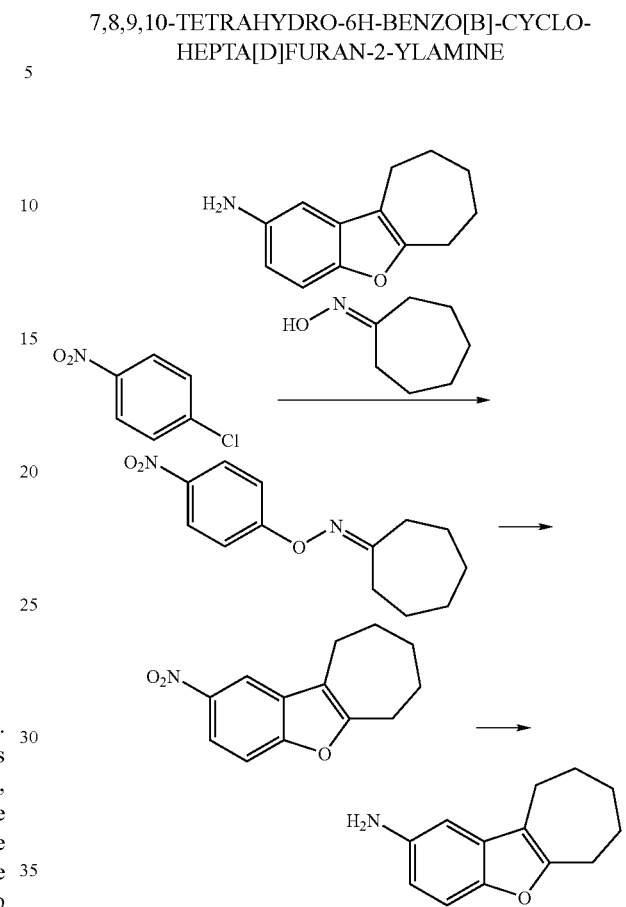

Potassium t-butoxide (19 g, 1600 mmol) was added in portions to a cooled (2° C.) solution of cycloheptanone oxime (19 g, 150 mmol) in DMF (150 mL). The cooled reaction mixture was stirred for 40 minutes and then 1-chloro-4-nitrobenzene (25 g, 160 mmol) in DMF (50 mL) was added over 5 minutes. The reaction mixture was stirred at ~10° C. for 30 minutes and then allowed to warm to room temperature and stirred for an additional 2 hours, and then stood at ambient temperature for 16 hours. The reaction mixture poured into water (1600 mL) with stirring. The mixture was stirred for an additional 20 minutes and then allowed to stand at room temperature for 5 hours. The precipitate was collected by filtration and washed with water. Recrystallization of the crude material from hexane provided cycloheptanone O-(4-nitro-phenyl)-oxime (30 g). Cycloheptanone O-(4-nitro-phenyl)-oxime (12 g, 50 mmol) was dissolved in warm isopropanol (120 mL) and 12 N hydrochloric acid (17 mL) was added. The reaction mixture was heated to reflux for 4 hours and then cooled in an ice bath. The solid was collected by filtration, washed with water and cold isopropanol, and dried in an oven to give 2-nitro-7,8,9,10-tetrahydro-6H-benzo[b]-cyclohepta[d]furan (7.8 g, 34 mmol). A mixture of 2-nitro-7,8,9,10-tetrahydro-6H-benzo[b]-cyclohepta[d]furan (5.8 g, 25 mmol) and Raney nickel (-5.6 g wet weight) in ethanol (270 mL) was hydrogenated at 50 PSI on a Parr shaker overnight. The mixture was filtered through Celite® and the filtrate was concentrated. The crude solid was purified by flash column chromatography (gradient elution with 15-25% ethyl acetate-hexanes) to give 7,8,9,10-tetrahydro-6H-benzo[b]-cyclohepta[d]furan-2-ylamine (4.6 g). Mp 98-99° C.

Preparation 4

6,7,8,9,10,11-HEXAHYDRO-BENZO[B]-CYCLOOCTA[D]FURAN-2-YLAMINE

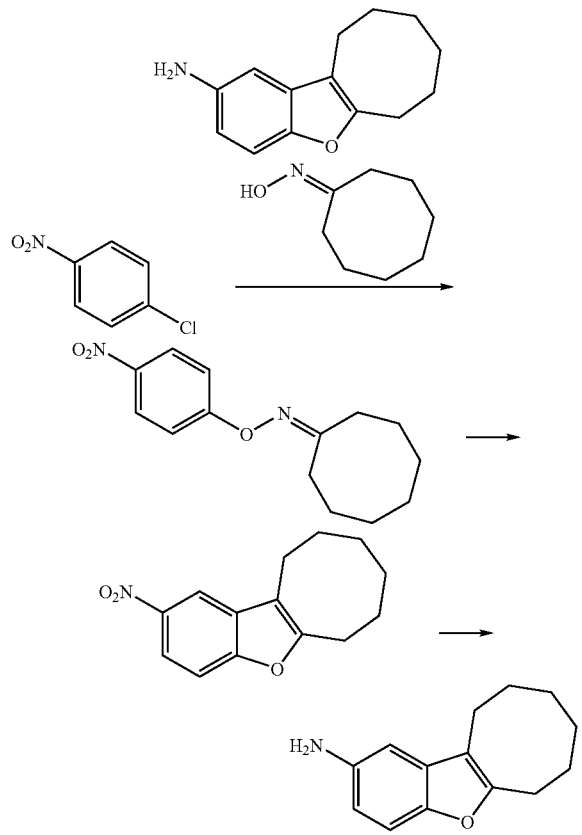

The core molecule was synthesized by the following procedure. Potassium t-butoxide (5.9 g, 53 mmol) was added in portions to a cooled (5° C.) solution of cycloheptanone oxime (7.5 g, 53 mmol) in DMF (100 mL). The cooled reaction mixture was stirred for 50 minutes and then 1-chloro-4-nitrobenzene (7.9 g, 50 mmol) in DMF (25 mL) was added over 5 minutes. The reaction mixture was stirred at ~10° C. for 30 minutes and then allowed to warm to room temperature and stirred for an additional 4 hours. The reaction mixture was concentrated under reduced pressure and the crude material was dissolved in ether and washed with water and brine. The organic phase was dried ($Na_2SO_4$) and concentrated to provide cyclooctanone O-(4-nitro-phenyl)-oxime (5.7 g). Cyclooctanone O-(4-nitro-phenyl)-oxime (5.3 g, 20 mmol) was dissolved in warm isopropanol (120 mL) and 12 N hydrochloric acid (6.8 mL) was added. The reaction mixture was heated to reflux for 5 hours and then cooled in an ice bath. The solid was collected by filtration, washed with water and cold isopropanol, and dried in an oven. The crude solid was purified by flash column chromatography (elution with 2% ethyl acetate-hexanes) to give 2-nitro-6,7,8,9,10,11-hexahydro-benzo[b]-cycloocta[d]furan (3.5 g, 14 mmol). A mixture of 2-nitro-6,7,8,9,10,11-hexahydro-benzo[b]-cycloocta[d]furan (3.4 g, 14 mmol) and Raney nickel (-4.1 g wet weight) in ethanol (170 mL) was hydrogenated at 50 PSI on a Parr shaker overnight. The mixture was filtered through Celite® and the filtrate was concentrated. The crude solid was purified by flash column chromatography (elution with 20% ethyl acetate-hexanes) to give 6,7,8,9,10,11-Hexahydro-benzo[b]-cycloocta[d]furan-2-ylamine (2.3 g). Mp 97-98° C.

Example 1

2,2-DIMETHYL-N-(6,7,8,9-TETRAHYDRO-DIBENZOFURAN-2-YL)-PROPIONAMIDE

Triethylamine (2.0 mL, 14 mmol) was added to a cooled (0° C.) solution of 6,7,8,9-tetrahydro-dibenzofuran-2-ylamine (0.86 g, 4.6 mmol). The reaction mixture was stirred for 10 minutes at 0° C. and then trimethylacetyl chloride (0.60 mL, 4.8 mmol) was added. The ice bath was removed and the reaction mixture was stirred for 30 min and then concentrated. The crude material was dissolved in chloroform and washed with 10% aqueous ammonium hydroxide, water, and brine, dried ($Na_2SO_4$) and concentrated. The crude material was recrystallized from acetonitrile to provide 2,2-dimethyl-N-(6,7,8,9-tetrahydro-dibenzofuran-2-yl)-propionamide (0.80 g). Mp 210-211° C.; Anal. Calcd. for $C_{17}H_{21}NO_2$: C, 75.25; H, 7.80; N, 5.16; Found: C, 75.33; H, 7.64; N, 5.07.

Example 2

3-METHYL-N-(6,7,8,9-TETRAHYDRO-DIBENZOFURAN-2-YL)-BUTYRAMIDE

Following the procedure for Example 1, tetrahydro-dibenzofuran-2-ylamine (1.1 g, 6.0 mmol), isovaleryl chloride (0.82 g, 6.6 mmol), and triethylamine (2.6 mL, 18 mmol) in tetrahydrofuran (11 mL) provided 3-methyl-N-(6,7,8,9-tetrahydro-dibenzofuran-2-yl)-butyramide (0.69 g) after recrystallization from t-butyl methyl ether. Mp 154-157° C.; Anal. Calcd. for $C_{17}H_{21}NO_2$: C, 75.25; H, 7.80; N, 5.16; Found: C, 75.20; H, 7.87; N, 5.26.

Example 3

3,3-DIMETHYL-N-(6,7,8,9-TETRAHYDRO-DIBENZOFURAN-2-YL)-BUTYRAMIDE

Following the procedure of Example 1, tetrahydro-dibenzofuran-2-ylamine (1.1 g, 6.0 mmol), t-butylacetyl chloride (0.93 mL, 6.6 mmol), and triethylamine (2.6 mL, 18 mmol) in tetrahydrofuran (11 mL) provided 3,3-dimethyl-N-(6,7,8,9- tetrahydro-dibenzofuran-2-yl)-butyramide (0.92 g). Mp 164-165° C.; Anal. Calcd. for $C_{18}H_{23}NO_2$: C, 75.76; H, 8.12; N, 4.91; Found: C, 75.62; H, 8.18; N, 5.00.

Example 4

2-PHENYL-N-(6,7,8,9-TETRAHYDRO-DIBENZOFURAN-2-YL)-ACETAMIDE

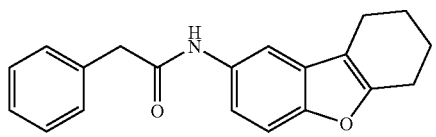

Following the procedure of Example 1, tetrahydro-dibenzofuran-2-ylamine (0.78 g, 4.1 mmol), phenylacetyl chloride (1.1 mL, 8.2 mmol), and triethylamine (1.8 mL, 13 mmol) in tetrahydrofuran (10 mL) provided 2-phenyl-N-(6,7,8,9-tetrahydro-dibenzofuran-2-yl)-acetamide (0.70 g). Mp 180-181° C.; Anal. Calcd. for $C_{20}H_{19}NO_2$: C, 78.66; H, 6.27; N, 4.59; Found: C, 78.53; H, 6.13; N, 4.75.

Example 5

ADAMANTANE-1-CARBOXYLIC ACID (6,7,8,9-TETRAHYDRO-DIBENZOFURAN-2-YL)-AMIDE

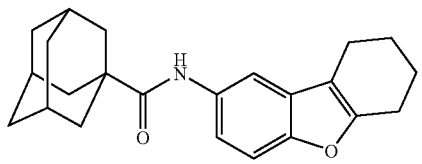

Following the procedure of Example 1, tetrahydro-dibenzofuran-2-ylamine (0.94 g, 5.0 mmol), adamantanecarbonyl chloride (1.1 g, 5.3 mmol), and triethylamine (2.1 mL, 15 mmol) in tetrahydrofuran (20 mL) provided adamantane-1-carboxylic acid (6,7,8,9-tetrahydro-dibenzofuran-2-yl)-amide (0.98 g). Mp 247-248° C.; Anal. Calcd. for $C_{23}H_{27}NO_2$: C, 79.05; H, 7.79; N, 4.01; Found: C, 78.75; H, 7.73; N, 3.75.

Example 6

4-TERT-BUTYL-N-(6,7,8,9-TETRAHYDRO-DIBENZOFURAN-2-YL)-BENZAMIDE

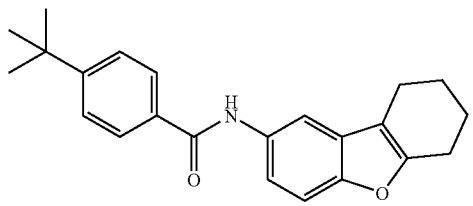

Following the procedure of Example 1, tetrahydro-dibenzofuran-2-ylamine (0.94 g, 5.0 mmol), 4-t-butylbenzoyl chloride (1.1 mL, 5.3 mmol), and triethylamine (2.1 mL, 15 mmol) in tetrahydrofuran (20 mL) provided 4-tert-butyl-N-(6,7,8,9-tetrahydro-dibenzofuran-2-yl)-benzamide (1.2 g). Mp 185-186° C.; Anal. Calcd. for $C_{23}H_{25}NO_2$: C, 79.51; H, 7.25; N, 4.03; Found: C, 79.33; H, 7.27; N, 3.94.

Example 7

2-CYCLOHEXYL-N-(6,7,8,9-TETRAHYDRO-DIBENZOFURAN-2-YL)-ACETAMIDE

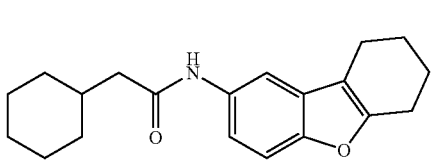

Following the procedure of Example 1, tetrahydro-dibenzofuran-2-ylamine (0.94 g, 5.0 mmol), cyclohexylacetyl chloride (0.80 g, 6.0 mmol), and triethylamine (2.1 mL, 15 mmol) in tetrahydrofuran (24 mL) provided 2-cyclohexyl-N-(6,7,8,9-tetrahydro-dibenzofuran-2-yl)-acetamide (0.32 g). Mp 189-191° C.; MS m/z 312 ([M+H]+); Anal. Calcd. for $C_{20}H_{25}NO_2$: C, 77.14; H, 8.09; N, 4.50; Found: C, 77.44; H, 8.08; N, 4.59.

Example 8

N-(6,7,8,9-TETRAHYDRO-DIBENZOFURAN-2-yl)-PROPIONAMIDE

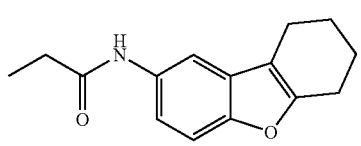

Following the procedure of Example 1, tetrahydro-dibenzofuran-2-ylamine (0.94 g, 5.0 mmol), propionyl chloride (0.47 mL, 5.3 mmol), and triethylamine (2.1 mL, 15 mmol) in tetrahydrofuran (20 mL) provided N-(6,7,8,9-tetrahydro-dibenzofuran-2-yl)-propionamide (0.23 g). Mp 164-165° C.; Anal. Calcd. for $C_{15}H_{17}NO_2$: C, 74.05; H, 7.04; N, 5.76; Found: C, 74.09; H, 7.09; N, 5.78.

Example 9

N-(6,7,8,9-TETRAHYDRO-DIBENZOFURAN-2-YL)-ISOBUTYRAMIDE

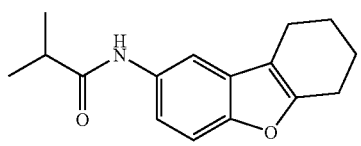

Following the procedure of Example 1, tetrahydro-dibenzofuran-2-ylamine (0.94 g, 5.0 mmol), isobutyryl chloride (0.56 mL, 5.2 mmol), and triethylamine (2.1 mL, 15 mmol) in tetrahydrofuran (30 mL) provided N-(6,7,8,9-tetrahydrodibenzofuran-2-yl)-isobutyramide (0.67 g). Mp 206.5-208.0° C.;MS m/z 258 ([M+H]+); Anal. Calcd. for $C_{15}H_{17}NO_2$: C, 74.68; H, 7.44; N, 5.44; Found: C, 74.43; H, 7.39; N, 5.50.

Example 10

N-(6,7,8,9-TETRAHYDRO-DIBENZOFURAN-2-YL)-BUTYRAMIDE

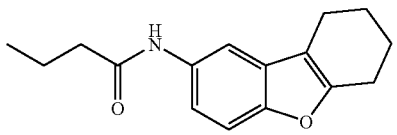

Following the procedure of Example 1, tetrahydro-dibenzofuran-2-ylamine (0.94 g, 5.0 mmol), isobutyryl chloride (0.55 mL, 5.2 mmol), and triethylamine (2.1 mL, 15 mmol) in tetrahydrofuran (20 mL) provided N-(6,7,8,9-tetrahydro-dibenzofuran-2-yl)-butyramide (0.18 g). Mp 133-135° C.;Anal. Calcd. for $C_{15}H_{17}NO_2$: C, 74.68; H, 7.44; N, 5.44; Found: C, 74.76; H, 7.48; N, 5.41.

Example 11

N-(6,7,8,9-TETRAHYDRO-DIBENZOFURAN-2-YL)-ACETAMIDE

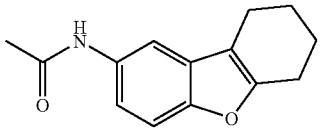

Following the procedure of Example 1, tetrahydro-dibenzofuran-2-ylamine (0.94 g, 5.0 mmol) and acetic anhydride (0.52 mL, 5.5 mmol) in pyridine (14 mL) provided N-(6,7,8,9-Tetrahydro-dibenzofuran-2-yl)-acetamide (0.56 g). Mp 195.5-197.5° C.; MS m/z 230 ([M+H]+); Anal. Calcd. for $C_{15}H_{17}NO_2$: C, 73.34; H, 6.59; N, 6.11; Found: C, 73.45; H, 6.54; N, 6.06.

Example 12

2-METHYL-N-(6,7,8,9-TETRAHYDRO-DIBENZOFURAN-2-YL)-BENZAMIDE

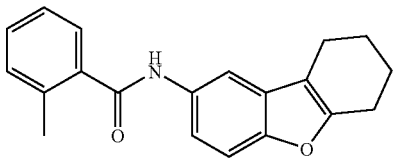

Following the procedure of Example 1, tetrahydro-dibenzofuran-2-ylamine (0.94 g, 5.0 mmol), o-toluoyl chloride (0.69 mL, 5.2 mmol), and triethylamine (2.1 mL, 15 mmol) in tetrahydrofuran (30 mL) provided 2-methyl-N-(6,7,8,9-tetrahydro-dibenzofuran-2-yl)-benzamide (1.0 g). Mp 209-210° C.;Anal. Calcd. for $C_{20}H_{19}NO_2$: C, 78.66; H, 6.27; N, 4.59; Found: C, 78.52; H, 6.28; N, 4.67.

Example 13

4-METHOXY-N-(6,7,8,9-TETRAHYDRO-DIBENZOFURAN-2-YL)-BENZAMIDE

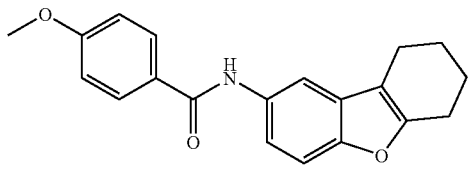

Following the procedure of Example 1, tetrahydro-dibenzofuran-2-ylamine (0.94 g, 5.0 mmol), anisoyl chloride (0.91 g, 5.3 mmol), and triethylamine (2.1 mL, 15 mmol) in tetrahydrofuran (25 mL) provided 4-methoxy-N-(6,7,8,9-tetrahydro-dibenzofuran-2-yl)-benzamide (1.0 g). Mp 197.0-197.5° C.; Anal. Calcd. for $C_{20}H_{19}NO_3$: C, 74.75; H, 5.96; N, 4.36; Found: C, 74.67; H, 5.87; N, 4.46.

Example 14

4-METHYL-N-(6,7,8,9-TETRAHYDRO-DIBENZOFURAN-2-YL)-PENTANAMIDE

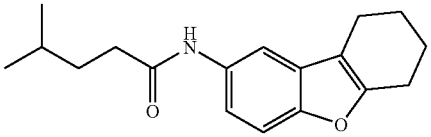

Following the procedure of Example 1, tetrahydro-dibenzofuran-2-ylamine (0.94 g, 5.0 mmol), 4-methylvaleryl chloride (1.5 g, 5.3 mmol), and triethylamine (2.1 mL, 15 mmol) in tetrahydrofuran (23 mL) provided 4-methyl-N-(6,7,8,9-tetrahydro-dibenzofuran-2-yl)-pentanamide (0.54 g). Mp 145.5-146.0° C.; Anal. Calcd. for $C_{18}H_{23}NO_2$: C, 75.76; H, 8.12; N, 4.91; Found: C, 75.46; H, 8.14; N, 4.92.

Example 15

4-NITRO-N-(6,7,8,9-TETRAHYDRO-DIBENZOFURAN-2-YL)-BENZAMIDE

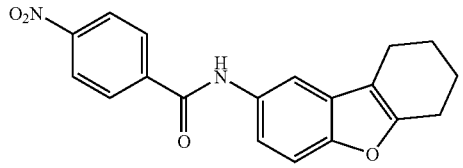

Following the procedure of Example 1, tetrahydro-dibenzofuran-2-ylamine (2.8 g, 15 mmol), 4-nitrobenzoyl chloride (3.0 g, 16 mmol), and triethylamine (6.4 mL, 45 mmol) in tetrahydrofuran (60 mL) provided 4-nitro-N-(6,7,8,9-tetrahydro-dibenzofuran-2-yl)-benzamide (4.1 g). Mp

Example 16

4-AMINO-N-(6,7,8,9-TETRAHYDRO-DIBENZO-FURAN-2-YL)-BENZAMIDE

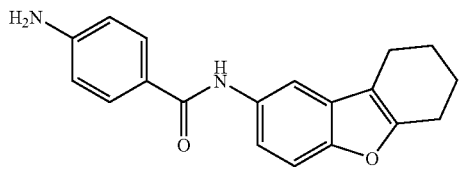

A mixture of 4-nitro-N-(6,7,8,9-tetrahydro-dibenzofuran-2-yl)-benzamide (0.67 g, 2.0 mmol) and Raney nickel (~1 g wet weight) in ethanol (200 mL) was hydrogenated at 40 PSI on a Parr shaker overnight. The mixture was filtered through Celite® and the filtrate was concentrated. The crude solid was recrystallized from acetonitrile to give 4-amino-N-(6,7,8,9-tetrahydro-dibenzofuran-2-yl)-benzamide (0.16 g). Mp 207-208° C; Anal. Calcd. for $C_{19}H_{18}N_2O_2$: C, 74.49; H, 5.92; N, 9.14; Found: C, 74.29; H, 5.74; N, 9.08.

Example 17

4-CHLORO-N-(6,7,8,9-TETRAHYDRO-DIBENZOFURAN-2-YL)-BENZAMIDE

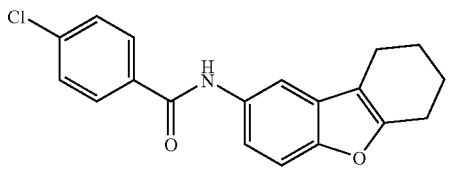

Following the procedure of Example 1, tetrahydro-dibenzofuran-2-ylamine (0.94 g, 5.0 mmol) and p-chlorobenzoyl chloride (0.72 mL, 5.5 mmol) in pyridine (10 mL) provided 4-chloro-N-(6,7,8,9-tetrahydro-dibenzofuran-2-yl)-benzamide (1.0 g). Mp 214.0-214.5° C.; Anal. Calcd. for $C_{19}H_{16}ClNO_2$: C, 70.05; H, 4.95; N, 4.30; Found: C, 70.10; H, 4.72; N, 4.17.

Example 18

N-(6,7,8,9-TETRAHYDRO-DIBENZOFURAN-2-YL)-BENZAMIDE

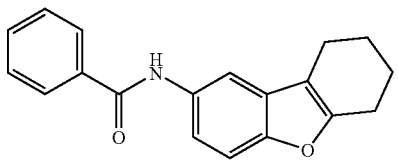

Following the procedure of Example 1, tetrahydro-dibenzofuran-2-ylamine (0.94 g, 5.0 mmol) and benzoyl chloride (0.64 mL, 5.5 mmol) in pyridine (10 mL) provided N-(6,7,8, 9-tetrahydro-dibenzofuran-2-yl)-benzamide (0.75 g). Mp 178-180° C.; Anal. Calcd. for $C_{19}H_{17}NO_2$: C, 78.33; H, 5.88; N, 4.81; Found: C, 78.10; H, 5.86; N, 4.81.

Example 19

4-FLUORO-N-(6,7,8,9-TETRAHYDRODIBENZO[B,D]FURAN-2-YL)BENZAMIDE

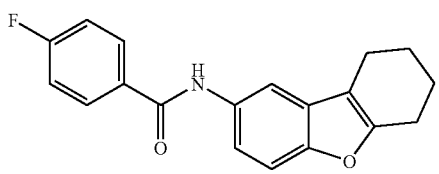

Following the procedure of Example 1, tetrahydro-dibenzofuran-2-ylamine (0.50 g, 2.7 mmol), 4-fluorobenzoyl chloride (0.32 mL, 2.7 mmol), and pyridine (0.54 mL, 6.7 mmol) in acetonitrile (30 mL) provided 4-fluoro-N-(6,7,8,9-tetrahydrodibenzo[b,d]furan-2-yl)benzamide (0.55 g) after filtering the precipitate from the reaction mixture. MS (ESI) m/z 310 ([M+H]+).

Example 20

N-(6,7,8,9-TETRAHYDRODIBENZO[B,D]FURAN-2-YL)-4-(TRIFLUOROMETHYL)BENZAMIDE

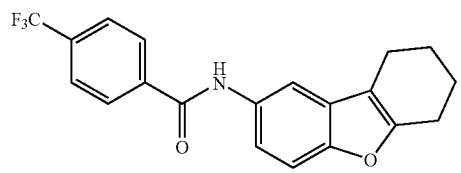

Following the procedure of Example 1, tetrahydro-dibenzofuran-2-ylamine (1.0 g, 5.3 mmol), 4-(trifluoromethyl)benzoyl chloride (0.79 mL, 5.3 mmol), and pyridine (1.1 mL, 13 mmol) in acetonitrile (50 mL) provided N-(6,7,8,9-tetrahydrodibenzo[b,d]furan-2-yl)-4-(trifluoromethyl)benzamide (1.1 g). MS (ESI) m/z 358 ([M−H]); m/z 360 ([M+H]+).

Example 21

3-PHENYL-N-(6,7,8,9-TETRAHYDRODIBENZO[B,D]FURAN-2-YL)PROPANAMIDE

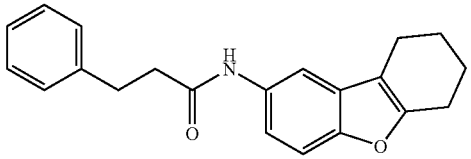

Following the procedure of Example 1, tetrahydro-dibenzofuran-2-ylamine (0.15 g, 0.80 mmol), hydrocinnamoyl chloride (0.12 mL, 0.80 mmol), and poly(vinylpyridine) (0.5

Example 22

N-(6,7,8,9-TETRAHYDRODIBENZO[B,D]FURAN-2-YL)HEXANAMIDE

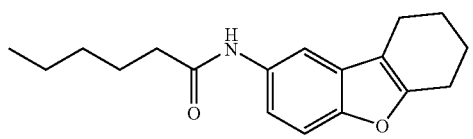

Following the procedure of Example 23, tetrahydro-dibenzofuran-2-ylamine (0.15 g, 0.80 mmol), hexanoyl chloride (0.11 mL, 0.80 mmol), and poly(vinylpyridine) (0.5 g) in dichloroethane (8 mL) provided N-(6,7,8,9-tetrahydrodibenzo[b,d]furan-2-yl)hexanamide (0.10 g). MS (ESI) m/z 286.

Example 23

N-(2,3-DIHYDRO-1H-CYCLOPENTA[B]BENZOFURAN-7-YL)-3,3-DIMETHYL-BUTYRAMIDE

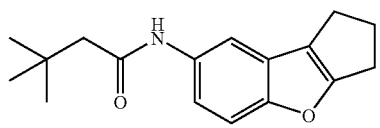

Following the procedure of Example 1, 2,3-dihydro-1H-cyclopenta[b]benzofuran-7-ylamine (0.87 g, 5.0 mmol) and t-butylacetyl chloride (0.77 mL, 5.5 mmol) in pyridine (10 mL) provided N-(2,3-dihydro-1 H-cyclopenta[b]benzofuran-7-yl)-3,3-dimethyl-butyramide (0.82 g). Mp 195.5-197.0 °c; MS (EI) m/z 272 ([M+H]+); Anal. Calcd. for $C_{17}H_{21}NO_2$: C, 75.25; H, 7.80; N, 5.16; Found: C, 75.34; H, 7.82; N, 5.14.

Example 24

N-(2,3-DIHYDRO-1H-CYCLOPENTA(b)BENZOFURAN-7-YL)-2,2-DIMETHYL-PROPIONAMIDE

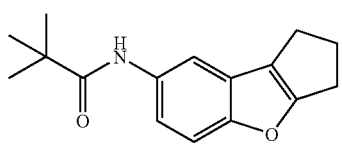

Following the procedure of Example 1, 2,3-dihydro-1H-cyclopenta[b]benzofuran-7-ylamine (0.69 g, 4.0 mmol) and trimethylacetyl chloride (0.55 mL, 4.4 mmol) in pyridine (10 mL) provided N-(2,3-dihydro-1-H-cyclopenta(b)benzofuran-7-yl)-2,2-dimethyl-propionamide (0.64 g). Mp 188.5-190.0° C.; MS m/z 258 ([M+H]+); Anal. Calcd. for $C_{16}H_{19}NO_2$: C, 74.68; H, 7.44; N, 5.44; Found: C, 74.67; H, 7.43; N, 5.39.

Example 25

N-(2,3-DIHYDRO-1H-CYCLOPENTA[B]BENZOFURAN-7-YL)-3-METHYL-BUTYRAMIDE

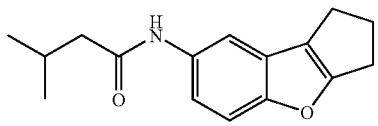

Following the procedure of Example 1, 2,3-dihydro-1H-cyclopenta[b]benzofuran-7-ylamine (0.69 g, 4.0 mmol) and isovaleryl chloride (0.55 mL, 4.4 mmol) in pyridine (10 mL) provided N-(2,3-Dihydro-1 H-cyclopenta[b]benzofuran-7-yl)-3-methyl-butyramide (0.67 g). Mp 162.0-163.0° C.; Anal. Calcd. for $C_{16}H_{19}NO_2$: C, 74.68; H, 7.44; N, 5.44; Found: C, 74.67; H, 7.70; N, 5.39.

Example 26

3,3-DIMETHYL-N-[7,8,9,10-TETRAHYDRO-6H-Benzo[B]-CYCLOHEPTA[d]FURAN-2-YL]BUTYRAMIDE

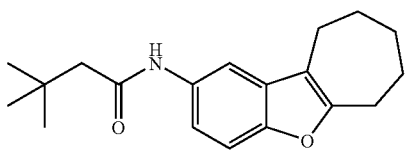

Following the procedure of Example 1, 7,8,9,10-tetrahydro-6H-benzo[b]-cyclohepta[d]furan-2-ylamine (1.0 g, 5.0 mmol) and t-butylacetyl chloride (0.74 mL, 5.5 mmol) in pyridine (10 mL) provided 3,3-dimethyl-N-[7,8,9,10-tetrahydro-6H-benzo[b]-cyclohepta[d]furan-2-yl]butyramide (0.92 g). Mp 182-183° C.; Anal. Calcd. for $C_{19}H_{25}NO_2$: C, 76.22; H, 8.42; N, 4.68; Found: C, 76.13; H, 8.28; N, 4.71.

Example 27

2,2-DIMETHYL-N-(6,7,8,9-TETRAHYDRO-5H-10-OXA-BENZO[A]AZULEN-3-YL)-PROPIONAMIDE

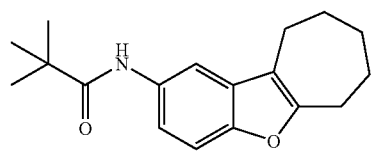

Following the procedure of Example 1, 7,8,9,10-tetrahydro-6H-benzo[b]-cyclohepta[d]furan-2-ylamine (1.0 g, 5.0 mmol) and trimethylacetyl chloride (0.68 mL, 5.5 mmol) in pyridine (10 mL) provided 2,2-dimethyl-N-(6,7,8,9-tetrahydro-5H-10-oxa-benzo[a]azulen-3-yl)-propionamide (1.2 g). Mp 208-209° C.; Anal. Calcd. for $C_{18}H_{23}NO_2$: C, 75.76; H, 8.12; N, 4.91; Found: C, 76.06; H, 8.03; N, 4.94.

Example 28

3-METHYL-N-[7,8,9,10-TETRAHYDRO-6H-Benzo[B]-Cyclohepta[D]FURAN-2-YL]BUTYRAMIDE

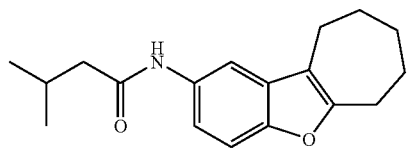

Following the procedure of Example 1, 7,8,9,10-tetrahydro-6H-benzo[b]-cyclohepta[d]furan-2-ylamine (1.0 g, 5.0 mmol) and isovaleryl chloride (0.68 mL, 5.5 mmol) in pyridine (10 mL) provided 3-methyl-N-[7,8,9,10-tetrahydro-6H-benzo[b]-cyclohepta[d]furan-2-yl]butyramide (0.73 g). Mp 162-163° C.; Anal. Calcd. for $C_{18}H_{23}NO_2$: C, 75.76; H, 8.12; N, 4.91; Found: C, 75.46; H, 8.04; N, 4.93.

Example 29

2-CYCLOHEXYL-N-[7,8,9,10-TETRAHYDRO-6H-BENZO[B]-CYCLOHEPTA[d]FURAN-2-YL]ACETAMIDE

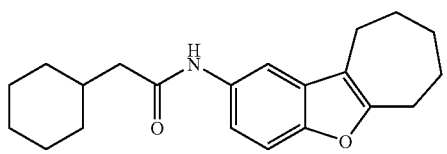

Following the procedure of Example 1, 7,8,9,10-tetrahydro-6H-benzo[b]-cyclohepta[d]furan-2-ylamine (0.91 g, 4.5 mmol) and cyclohexylacetyl chloride (0.80 g, 5.0 mmol) in pyridine (10 mL) provided 2-cyclohexyl-N-[7,8,9,10-tetrahydro-6H-benzo[b]-cyclohepta[d]furan-2-yl]acetamide (0.53 g). Mp 188-189° C.; Anal. Calcd. for $C_{21}H_{27}NO_2$: C, 77.50; H, 8.36; N, 4.30; Found: C, 77.51; H, 8.43; N, 4.32.

Example 30

2-(4-FLUOROPHENYL)-N-(7,8,9,10-TETRAHYDRO-6H-BENZO[B]CYCLOHEPTA[D]FURAN-2-YL)ACETAMIDE

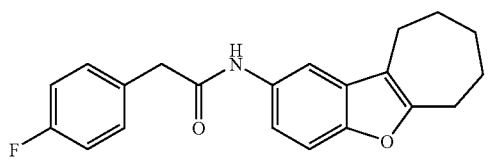

Triethylamine (0.52 mL, 3.7 mmol), 1-(3-dimethylaminopropyl)-3-ethylcarbodiimide (0.37 g, 1.9 mmol), N-hydroxybenzotriazole (0.26 g, 1.9 mmol) and 4-fluorophenylacetic acid (0.27 g, 1.8 mmol) were added sequentially to a solution of 7,8,9,10-tetrahydro-6H-benzo[b]-cyclohepta[d]furan-2-ylamine (0.30 g, 1.5 mmol) in dichloromethane (20 mL). The reaction mixture was stirred overnight at ambient temperature and then concentrated. The crude material was dissolved in ethyl acetate and washed with 1 N NaOH and water, dried (MgSO$_4$) and concentrated to give 2-(4-fluorophenyl)-N-(7, 8,9,10-tetrahydro-6H-benzo[b]cyclohepta[d]furan-2-yl)acetamide (0.47 g). MS (ESI) m/z 338 ([M+H]+).

Example 31

N-(7,8,9,10-TETRAHYDRO-6H-BENZO[B]CYCLOHEPTA[d]FURAN-2-YL)PENTANAMIDE

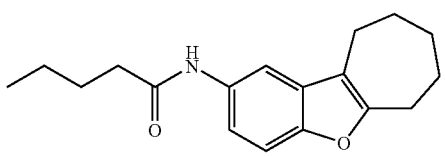

Following the procedure of Example 1, 7,8,9,10-tetrahydro-6H-benzo[b]-cyclohepta[d]furan-2-ylamine (0.25 g, 1.2 mmol), valeryl chloride (0.16 mL, 1.4 mmol), and pyridine (0.30 mL, 3.7 mmol) in acetonitrile (15 mL) provided N-(7,8,9,10-tetrahydro-6H-benzo[b]cyclohepta[d]furan-2-yl)pentanamide (0.17 g). MS (ESI) m/z 286([M+H]+).

Example 32

ETHYL 4-OXO-4-(7,8,9,10-TETRAHYDRO-6H-BENZO[B]CYCLOHEPTA[D]FURAN-2-YLAMINO)BUTANOATE

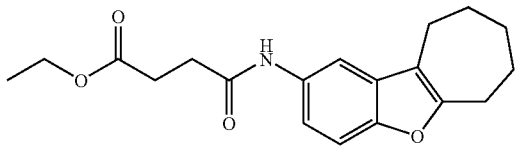

Following the procedure of Example 1, 7,8,9,10-tetrahydro-6H-benzo[b]-cyclohepta[d]furan-2-ylamine (0.25 g, 1.2 mmol), ethyl succinyl chloride (0.23 g, 1.4 mmol), and pyridine (0.30 mL, 3.7 mmol) in acetonitrile (15 mL) provided ethyl 4-oxo-4-(7,8,9,10-tetrahydro-6H-benzo[b]cyclohepta[d]furan-2-ylamino)butanoate (0.36 g). MS (ESI) m/z 330 ([M+H]+).

Example 33

4-TERT-BUTYL-N-(7,8,9,10-TETRAHYDRO-6H-BENZO[B]CYCLOHEPTA[D]FURAN-2-YL)BENZAMIDE

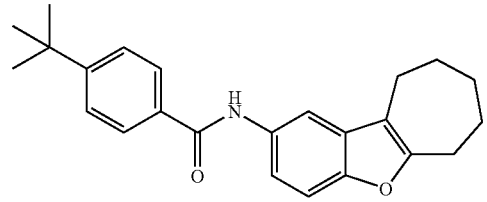

Following the procedure of Example 1,7,8,9,10-tetrahydro-6H-benzo[b]-cyclohepta[d]furan-2-ylamine (0.13 g, 0.62 mmol), 4-t-butylbenzoyl chloride (0.12 mL, 0.65 mmol), and poly(vinylpyridine) (0.5 g) in dichloroethane (15 mL) provided 4-tert-butyl-N-(7,8,9,10-tetrahydro-6H-benzo[b]cyclohepta[d]furan-2-yl)benzamide (0.14 g). MS (ESI) m/z 362 ([M+H]+).

Example 34

N-(7,8,9,10-TETRAHYDRO-6H-BENZO[B]CYCLOHEPTA[D]FURAN-2-YL)PROPANAMIDE

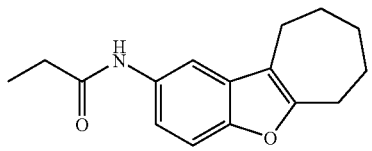

Following the procedure of Example 1,7,8,9,10-tetrahydro-6H-benzo[b]-cyclohepta[d]furan-2-ylamine (0.13 g, 0.62 mmol), propionyl chloride (0.060 mL, 0.68 mmol), and poly(vinylpyridine) (0.5 g) in dichloroethane (15 mL) provided N-(7,8,9,10-tetrahydro-6H-benzo[b]cyclohepta[d]furan-2-yl)propanamide (0.11 g). MS (ESI) m/z 258 ([M+H]+).

Example 35

N-(7,8,9,10-TETRAHYDRO-6H-BENZO[B]CYCLOHEPTA[D]FURAN-2-YL)HEXANAMIDE

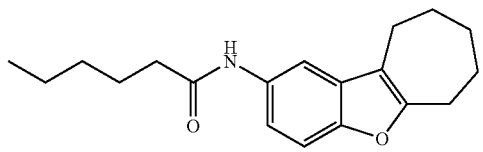

Following the procedure of Example 1,7,8,9,10-tetrahydro-6H-benzo[b]-cyclohepta[d]furan-2-ylamine (0.15 g, 0.75 mmol), hexanoyl chloride (0.10 mL, 0.75 mmol), and poly(vinylpyridine) (0.5 g) in dichloroethane (8 mL) provided N-(7,8,9,10-tetrahydro-6H-benzo[b]cyclohepta[d]furan-2-yl)hexanamide (0.15 g). MS (ESI) m/z 300 ([M+H]+).

Example 36

3-PHENYL-N-(7,8,9,10-TETRAHYDRO-6H-BENZO[B]CYCLOHEPTA[D]FURAN-2-YL)PROPANAMIDE

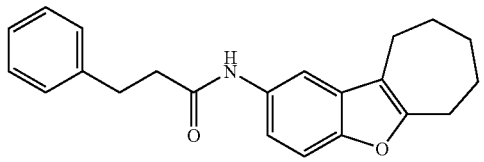

Following the procedure of Example 1,7,8,9,10-tetrahydro-6H-benzo[b]-cyclohepta[d]furan-2-ylamine (0.15 g, 0.75 mmol), hydrocinnamoyl chloride (0.11 mL, 0.75 mmol), and poly(vinylpyridine) (0.5 g) in dichloroethane (8 mL) provided 3-phenyl-N-(7,8,9,10-tetrahydro-6H-benzo[b]cyclohepta[d]furan-2-yl)propanamide (0.16 g).MS (ESI) m/z 334 ([M+H]+).

Example 37

N-(7,8,9,10-TETRAHYDRO-6H-BENZO[B]CYCLOHEPTA[D]FURAN-2-YL)-2-THIEN-2-YLACETAMIDE

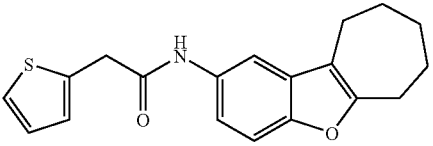

Following the procedure of Example 1,7,8,9,10-tetrahydro-6H-benzo[b]-cyclohepta[d]furan-2-ylamine (0.20 g, 1.0 mmol), 2-thiopheneacetyl chloride (0.13 mL, 1.0 mmol), and poly(vinylpyridine) (0.5 g) in dichloroethane (12 mL) provided N-(7,8,9,10-tetrahydro-6H-benzo[b]cyclohepta[d]furan-2-yl)-2-thien-2-ylacetamide (0.19 g).MS (ESI) m/z 326 ([M+H]+); MS (ESI) m/z 324 ([M−H]−).

Example 38

N-7,8,9,10-TETRAHYDRO-6H-BENZO[B]CYCLOHEPTA[D]FURAN-2-yl-4-(TRIFLUOROMETHYL)BENZAMIDE

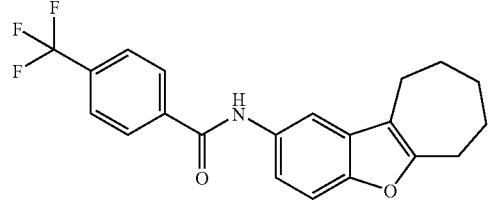

Following the procedure of Example 1,7,8,9,10-tetrahydro-6H-benzo[b]-cyclohepta[d]furan-2-ylamine (0.15 g, 0.75 mmol), 2-(trifluoromethyl)benzoyl chloride (0.11 mL, 0.75 mmol), and poly(vinylpyridine) (0.5 g) in dichloroethane (15 mL) provided N-7,8,9,10-tetrahydro-6H-benzo[b]cyclohepta[d]furan-2-yl-4-(trifluoromethyl) benzamide (0.19 g).MS (ESI) m/z 374 ([M+H]+);MS (ESI) m/z 372 ([M−H]−).

Example 39

2-CHLORO-N-7,8,9,10-TETRAHYDRO-6H-BENZO[B]CYCLOHEPTA[D]FURAN-2-YLACETAMIDE

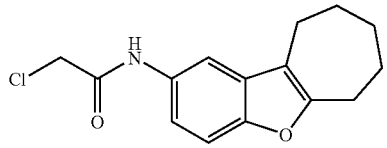

Following the procedure of Example 1,7,8,9,10-tetrahydro-6H-benzo[b]-cyclohepta[d]furan-2-ylamine (4.1 g, 20 mmol), chloroacetyl chloride (1.7 mL, 21 mmol), and pyridine (2.5 mL, 30 mmol)) in dichloroethane (40 mL) provided 2-chloro-N-7,8,9,10-tetrahydro-6H-benzo[b]cyclohepta[d]furan-2-ylacetamide (4.0 g). MS (ESI) m/z 276.

Example 40

2-MORPHOLIN-4-YL-N-7,8,9,10-TETRAHYDRO-6H-BENZO[b]CYCLOHEPTA[D]FURAN-2-YLACETAMIDE

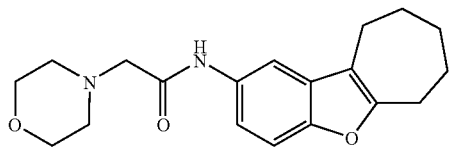

A mixture of 2-chloro-N-7,8,9,10-tetrahydro-6H-benzo[b]cyclohepta[d]furan-2-ylacetamide (0.13 g, 0.45 mmol), morpholine (0.049 mL, 0.56 mmol), and cesium carbonate (0.29 g, 0.90 mmol) in acetonitrile (5 mL) was stirred overnight at room temperature. The reaction mixture was concentrated and the crude material was purified using reverse-phase HPLC to provide 2-morpholin-4-yl-N-7,8,9,10-tetrahydro-6H-benzo[b]cyclohepta[d]furan-2-ylacetamide (0.085 g). MS (ESI) m/z 329 ([M+H]+).

Example 41

$N^2$-[2-(DIMETHYLAMINO)ETHYL]-N-METHYL-$N^1$-7,8,9,10-TETRAHYDRO-6H-BENZO[b]CYCLOHEPTA[D]FURAN-2-YLGLYCINAMIDE

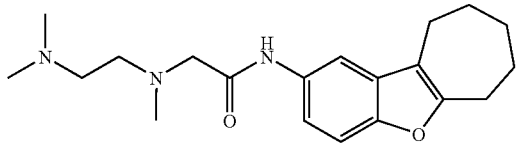

Following the procedure of Example 40, 2-chloro-N-7,8,9,10-tetrahydro-6H-benzo[b]cyclohepta[d]furan-2-ylacetamide (0.13 g, 0.45 mmol), N,N,N'-trimethylethylenediamine (0.073 mL, 0.56 mmol), and cesium carbonate (0.29 g, 0.90 mmol) in acetonitrile (5 mL) provided $N^2$-[2-(dimethylamino)ethyl]-$N^2$-methyl-$N^1$-7,8,9,10-tetrahydro-6H-benzo[b]cyclohepta[d]furan-2-ylglycinamide (0.058 g) as its hydrochloride salt after normal phase HPLC purification and treatment with 4 N hydrochloric acid in dioxane. MS (ESI) m/z 344 ([M+H]+).

Example 42

$N^2$-METHYL-$N^2$-(2-PYRIDIN-2-YLETHYL)-$N^1$-7,8,9,10-TETRAHYDRO-6H-BENZO[B]CYCLOHEPTA[D]FURAN-2-YLGLYCINAMIDE

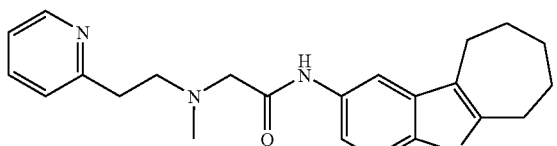

Following the procedure of Example 40, 2-chloro-N-7,8,9,10-tetrahydro-6H-benzo[b]cyclohepta[d]furan-2-ylacetamide (0.13 g, 0.45 mmol), 2-(2-methylaminoethyl)pyridine (0.078 mL, 0.56 mmol), and cesium carbonate (0.29 g, 0.90 mmol) in acetonitrile (5 mL) provided $N^2$-methyl-$N^2$-(2-pyridin-2-ylethyl)-$N^1$-7,8,9,10-tetrahydro-6H-benzo[b]cyclohepta[d]furan-2-ylglycinamide (0.095 g) as its trifluroacetic acid salt after reverse-phase HPLC purification. MS (ESI) m/z 378 ([M+H]+).

Example 43

2-(1,4-DIOXA-8-AZASPIRO[4.5]DEC-8-YL)-N-7,8,9,10-TETRAHYDRO-6H-BENZO[b]CYCLOHEPTA[D]FURAN-2-YLACETAMIDE

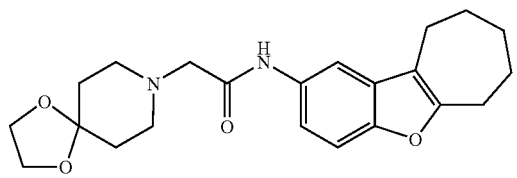

Following the procedure of Example 40, 2-chloro-N-7,8,9,10-tetrahydro-6H-benzo[b]cyclohepta[d]furan-2-ylacetamide (0.13 g, 0.45 mmol), 1,4-dioxa-8-azaspiro(4.5)decane (0.072 mL, 0.56 mmol), and cesium carbonate (0.29 g, 0.90 mmol) in acetonitrile (5 mL) provided 2-(1,4-dioxa-8-azaspiro[4.5]dec-8-yl)-N-7,8,9,10-tetrahydro-6H-benzo[b]cyclohepta[d]furan-2-ylacetamide (0.080 g) as its trifluoroacetic acid salt after reverse-phase HPLC purification. MS (ESI) m/z 385 ([M+H]+).

Example 44

2-(4-METHYLPIPERAZIN-1-YL)-N-7,8,9,10-TETRAHYDRO-6H-BENZO[B]CYCLOHEPTA[D]FURAN-2-YLACETAMIDE

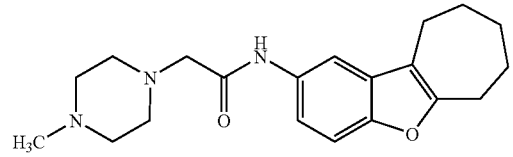

Following the procedure of Example 40, 2-chloro-N-7,8,9,10-tetrahydro-6H-benzo[b]cyclohepta[d]furan-2-ylacetamide (0.13 g, 0.45 mmol), N-methylpiperazine (0.062 mL, 0.56 mmol), and cesium carbonate (0.29 g, 0.90 mmol) in acetonitrile (5 mL) provided 2-(4-methylpiperazin-1-yl)-N-7,8,9,10-tetrahydro-6H-benzo[b]cyclohepta[d]furan-2-ylacetamide (0.039 g) as its trifluoroacetic acid salt after reverse-phase HPLC purification. MS (ESI) m/z 342 ([M+H]+).

Example 45

2-(2-HYDROXYETHOXY)-N-7,8,9,10-TETRAHYDRO-6H-BENZO[B]CYCLOHEPTA[D]FURAN-2-YLACETAMIDE

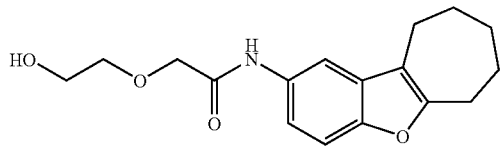

Following the procedure of Example 40, 2-chloro-N-7,8,9,10-tetrahydro-6H-benzo[b]cyclohepta[d]furan-2-ylacetamide (0.13 g, 0.45 mmol), ethylene glycol (0.031 mL, 0.56 mmol), and potassium tert-butoxide (0.10 g, 0.90 mmol) in dimethylformamide (5 m L) provided 2-(2-hydroxyethoxy)-N-7,8,9,10-tetrahydro-6H-benzo[b]cyclohepta[d]furan-2-ylacetamide (0.016 g) after reverse-phase HPLC purification. MS (ESI) m/z 304 ([M+H]+); MS (ESI) m/z 302 ([M–H]–).

Example 46

$N^2$-ETHYL-$N^2$-METHYL-N'-7,8,9,10-TETRAHYDRO-6H-BENZO[B]CYCLOHEPTA[D]FURAN-2-YLGLYCINAMIDE

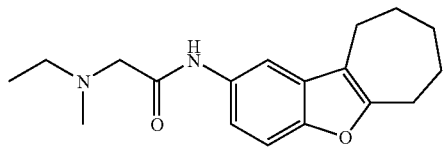

Following the procedure of Example 40, 2-chloro-N-7,8,9,10-tetrahydro-6H-benzo[b]cyclohepta[d]furan-2-ylacetamide (0.13 g, 0.45 mmol), N-ethylmethylamine (0.048 mL, 0.56 mmol), and cesium carbonate (0.29 g, 0.90 mmol) in acetonitrile (5 mL) provided W-ethyl-$N^2$-methyl-$N^2$-7,8,9,10-tetrahydro-6H-benzo[b]cyclohepta[d]furan-2-ylglycinamide (0.069 g) as its trifluroacetic acid salt after reverse-phase HPLC purification. MS (ES) m/z 301.2 ([M+H]+).

Example 47

$N^2$-(2-HYDROXYETHYL)-$N^2$-METHYL-N'-7,8,9,10-TETRAHYDRO-6H-BENZO[B]CYCLOHEPTA[D]FURAN-2-YLGLYCINAMIDE

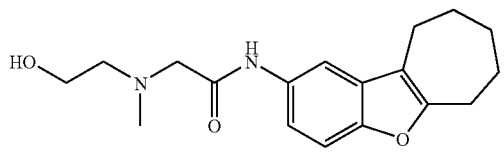

Following the procedure of Example 40, 2-chloro-N-7,8,9,10-tetrahydro-6H-benzo[b]cyclohepta[d]furan-2-ylacetamide (0.13 g, 0.45 mmol), 2-(methylamino)ethanol (0.045 mL, 0.56 mmol), and cesium carbonate (0.29 g, 0.90 mmol) in acetonitrile (5 mL) provided $N^2$-(2-hydroxyethyl)-$N^2$-methyl-$N^1$-7,8,9,10-tetrahydro-6H-benzo[b]cyclohepta[d]furan-2-ylglycinamide (0.022 g) as its trifluroacetic acid salt after reverse-phase HPLC purification. MS (ESI) m/z 317 ([M+H]+); MS (ESI) m/z 315 ([M–H]–).

Example 48

2-TERT-BUTOXY-N-7,8,9,10-TETRAHYDRO-6H-BENZO[B]CYCLOHEPTA[D]FURAN-2-YLACETAMIDE

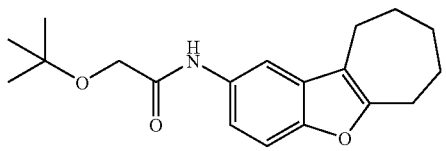

Following the procedure of Example 40, 2-chloro-N-7,8,9,10-tetrahydro-6H-benzo[b]cyclohepta[d]furan-2-ylacetamide (0.13 g, 0.45 mmol), water (0.010 mL, 0.56 mmol), and potassium tert-butoxide (0.10 g, 0.90 mmol) in dimethylformamide (5 mL) provided 2-tert-butoxy-N-7,8,9,10-tetrahydro-6H-benzo[b]cyclohepta[d]furan-2-ylacetamide (0.015 g) after reverse-phase HPLC purification. MS (ES) m/z 260.1 ([M+H]+).

Example 49

BENZYL [(1S)-1-METHYL-2-OXO-2-(7,8,9,10-TETRAHYDRO-6H-BENZO[B]CYCLOHEPTA[D]FURAN-2-YLAMINO)ETHYL]CARBAMATE

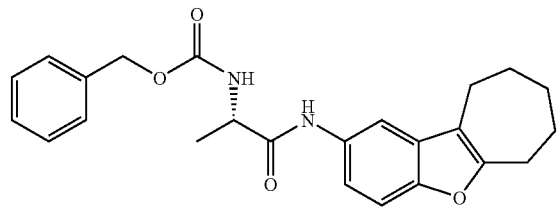

Following the procedure of Example 30, triethylamine (0.52 mL, 3.7 mmol), 1-(3-dimethylaminopropyl)-3-ethylcarbodiimide (0.37 g, 1.9 mmol), N-hydroxybenzotriazole (0.26 g, 1.9 mmol), N-carbobenzyloxy-L-alanine (0.37 g, 1.6 mmol), and 7,8,9,10-tetrahydro-6H-benzo[b]-cyclohepta[d]furan-2-ylamine (0.30 g, 1.5 mmol) provided benzyl [(1S)-1-methyl-2-oxo-2-(7,8,9,10-tetrahydro-6H-benzo[b]cyclohepta[d]furan-2-ylamino)ethyl]carbamate (0.08 g) after purification by flash column chromatography (elution with 40% ethyl acetate-hexanes). MS (ES) m/z 407.2 ([M+H]+).

Example 50

2-(4-PYRIMIDIN-2-YLPIPERAZIN-1-YL)-N-7,8,9,10-TETRAHYDRO-6H-BENZO[B]CYCLOHEPTA[D]FURAN-2-YLACETAMIDE

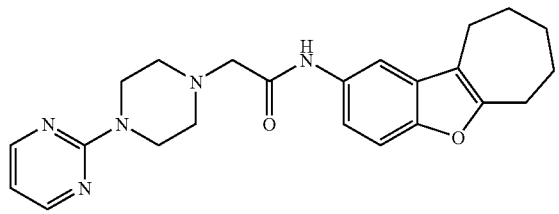

Following the procedure of Example 40, 2-chloro-N-7,8,9,10-tetrahydro-6H-benzo[b]cyclohepta[d]furan-2-ylacetamide (0.13 g, 0.45 mmol), 1-(pyrimidyl)piperazine dihydrochloride (0.13, 0.56 mmol), and cesium carbonate (0.58 g, 1.8 mmol) in acetonitrile (5 mL) provided 2-(4-pyrimidin-2-ylpiperazin-1-yl)-N-7,8,9,10-tetrahydro-6H-benzo[b]cyclohepta[d]furan-2-ylacetamide (0.022 g) after purification by flash column chromatography (elution with 3% methanol-1% ammonia-dichloromethane). MS (ES) m/z 406.3 ([M+H]+).

Example 51

TERT-BUTYL [2-OXO-2-(7,8,9,10-TETRAHYDRO-6H-BENZO[B]CYCLOHEPTA[D]FURAN-2-YLAMINO)ETHYL]CARBAMATE

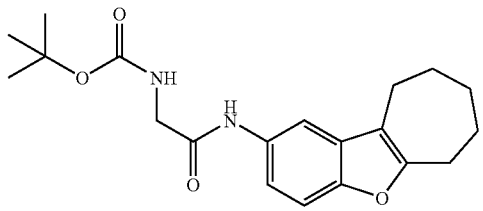

Following the procedure of Example 30, triethylamine (0.43 mL, 3.1 mmol), 1-(3-dimethylaminopropyl)-3-ethylcarbodiimide (0.31 g, 1.6 mmol), N-hydroxybenzotriazole (0.22 g, 1.6 mmol), N-Boc-glycine (0.24 g, 1.4 mmol), and 7,8,9,10-tetrahydro-6H-benzo[b]-cyclohepta[d]furan-2-ylamine (0.25 g, 1.2 mmol) provided tert-butyl [2-oxo-2-(7,8,9,10-tetrahydro-6H-benzo[b]cyclohepta[d]furan-2-ylamino)ethyl]carbamate (0.20 g). MS (ESI) m/z 359 ([M+H]+); MS (ESI) m/z 357.2 ([M−H]−).

Example 52

N¹-7,8,9,10-TETRAHYDRO-6H-BENZO[B]CYCLOHEPTA[D]FURAN-2-YLGLYCINAMIDE

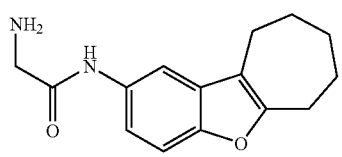

A solution of tert-butyl [2-oxo-2-(7,8,9,10-tetrahydro-6H-benzo[b]cyclohepta[d]furan-2-ylamino)ethyl]carbamate (0.10 g) in 1:1 trifluoroacetic acid:dichloromethane (5 mL) was stirred at room temperature for 30 min and then concentrated to provide N¹-7,8,9,10-tetrahydro-6H-benzo[b]cyclohepta[d]furan-2-ylglycinamide (52 mg) as its trifluoroacetic acid salt. MS (ESI) m/z 259 ([M+H]+).

Example 53

TERT-BUTYL [(1S)-1-BENZYL-2-OXO-2-(7,8,9,10-TETRAHYDRO-6H-BENZO[B]CYCLOHEPTA[D]FURAN-2-YLAMINO)ETHYL]CARBAMATE

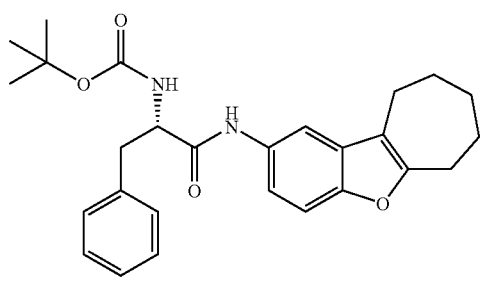

Following the procedure of Example 30, triethylamine (0.43 mL, 3.1 mmol), 1-(3-dimethylaminopropyl)-3-ethylcarbodiimide (0.31 g, 1.6 mmol), N-hydroxybenzotriazole (0.22 g, 1.6 mmol), N-Boc-L-phenylalanine (0.36 g, 1.4 mmol), and 7,8,9,10-tetrahydro-6H-benzo[b]-cyclohepta[d]furan-2-ylamine (0.25 g, 1.2 mmol) provided tert-butyl [(1S)-1-benzyl-2-oxo-2-(7,8,9,10-tetrahydro-6H-benzo[b]cyclohepta[d]furan-2-ylamino)ethyl]carbamate (0.21 g). MS (ESI) m/z 449 ([M+H]+); MS (ESI) m/z 447.3 ([M−H]−).

Example 54

TERT-BUTYL (2S)-2-[(7,8,9,10-TETRAHYDRO-6H-BENZO[B]CYCLOHEPTA[D]FURAN-2-YLAMINO)CARBONYL]PYRROLIDINE-1-CARBOXYLATE

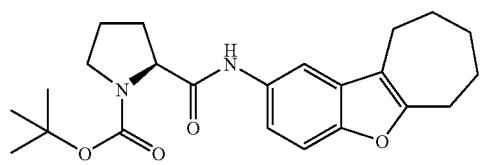

Following the procedure of Example 30, triethylamine (0.43 mL, 3.1 mmol), 1-(3-dimethylaminopropyl)-3-ethylcarbodiimide (0.31 g, 1.6 mmol), N-hydroxybenzotriazole (0.22 g, 1.6 mmol), N-Boc-L-proline (0.29 g, 1.4 mmol), and 7,8,9,10-tetrahydro-6H-benzo[b]-cyclohepta[d]furan-2-ylamine (0.25 g, 1.2 mmol) provided tert-butyl (2S)-2-[(7,8,9,10-tetrahydro-6H-benzo[b]cyclohepta[d]furan-2-ylamino)carbonyl]pyrrolidine-1-carboxylate (0.18 g). MS (ESI) m/z 399 ([M+H]+); MS (ESI) m/z 397.3 ([M−H]−).

Example 55

TERT-BUTYL [(1S)-2-OXO-1-(PYRIDIN-4-YLM-ETHYL)-2-(7,8,9,10-TETRAHYDRO-6H-BENZO[B]CYCLOHEPTA[D]FURAN-2-YLAMINO)ETHYL]CARBAMATE

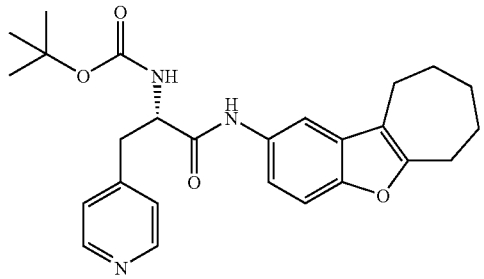

Following the procedure of Example 30, triethylamine (0.43 mL, 3.1 mmol), 1-(3-dimethylaminopropyl)-3-ethyl-carbodiimide (0.31 g, 1.6 mmol), N-hydroxybenzotriazole (0.22 g, 1.6 mmol), N-Boc-L-4-pyridylalanine (0.43 g, 1.4 mmol), and 7,8,9,10-tetrahydro-6H-benzo[b]-cyclohepta[d]furan-2-ylamine (0.25 g, 1.2 mmol) provided tert-butyl [(1S)-2-oxo-1-(pyridin-4-ylmethyl)-2-(7,8,9,10-tetrahydro-6H-benzo[b]cyclohepta[d]furan-2-ylamino)ethyl]carbamate (0.22 g). MS (ESI) m/z450 ([M+H]+).

Example 56

TERT-BUTYL [(1S)-1-METHYL-2-OXO-2-(7,8,9,10-TETRAHYDRO-6H-BENZO[B]CYCLOHEPTA[D]FURAN-2-YLAMINO)ETHYL]CARBAMATE

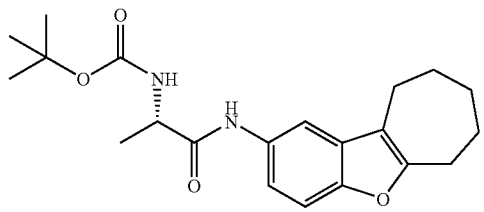

Following the procedure of Example 30, triethylamine (0.43 mL, 3.1 mmol), 1-(3-dimethylaminopropyl)-3-ethyl-carbodiimide (0.31 g, 1.6 mmol), N-hydroxybenzotriazole (0.22 g, 1.6 mmol), N-Boc-L-4-alanine (0.26 g, 1.4 mmol), and 7,8,9,10-tetrahydro-6H-benzo[b]-cyclohepta[d]furan-2-ylamine (0.25 g, 1.2 mmol) provided tert-butyl [(1S)-1-methyl-2-oxo-2-(7,8,9,10-tetrahydro-6H-benzo[b]cyclohepta[d]furan-2-ylamino)ethyl]carbamate (0.19 g). MS (ESI) m/z 373 ([M+H]).

Example 57

N-7,8,9,10-TETRAHYDRO-6H-BENZO[B]CYCLOHEPTA[D]FURAN-2-YL-L-PROLINAMIDE

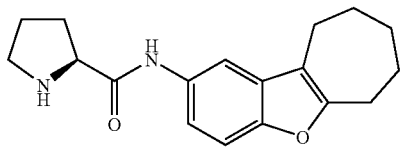

A solution of tert-butyl [(1S)-1-methyl-2-oxo-2-(7,8,9,10-tetrahydro-6H-benzo[b]cyclohepta[d]furan-2-ylamino)ethyl]carbamate (0.10 g) in 4 N HCl in dioxane (3 mL) and dichloromethane (3 mL) was stirred at room temperature for 30 min and then concentrated to provide N-7,8,9,10-tetrahydro-6H-benzo[b]cyclohepta[d]furan-2-yl-L-prolinamide (46 mg) as its hydrochloric acid salt. MS (ESI) m/z 299 ([M+H]+).

Example 58

N-[(BENZYLOXY)CARBONYL]-L-PHENYLALANYL-N$^1$-7,8,9,10-TETRAHYDRO-6H-BENZO[B]CYCLOHEPTA[D]FURAN-2-YL-L-ALANINAMIDE

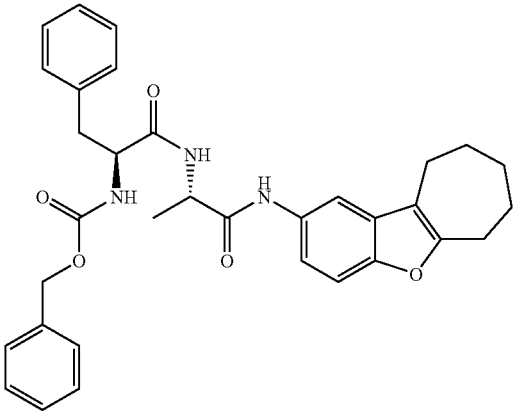

Following the procedure of Example 30, triethylamine (0.43 mL, 3.1 mmol), 1-(3-dimethylaminopropyl)-3-ethyl-carbodiimide (0.31 g, 1.6 mmol), N-hydroxybenzotriazole (0.22 g, 1.6 mmol), N-Cbz-Phe-Ala-OH (0.51 g, 1.4 mmol), and 7,8,9,10-tetrahydro-6H-benzo[b]-cyclohepta[d]furan-2-ylamine (0.25 g, 1.2 mmol) provided N-[(benzyloxy)carbonyl]-L-phenylalanyl-N$^1$-7,8,9,10-tetrahydro-6H-benzo[b]cyclohepta[d]furan-2-yl-L-alaninamide (0.17 g). MS (ESI) m/z 554 ([M+H]+).

Example 59

TERT-BUTYL {(1R,2R)-2-(BENZYLOXY)-1-[(7,8,9,10-TETRAHYDRO-6H-BENZO[B]CYCLOHEPTA[D]FURAN-2-YLAMINO)CARBONYL]PROPYL}CARBAMATE

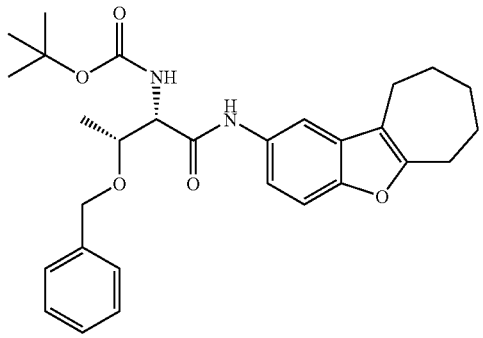

Following the procedure of Example 30, triethylamine (0.43 mL, 3.1 mmol), 1-(3-dimethylaminopropyl)-3-ethylcarbodiimide (0.31 g, 1.6 mmol), N-hydroxybenzotriazole (0.22 g, 1.6 mmol), N-Boc-D-Thr(Bzl)-OH (0.42 g, 1.4 mmol), and 7,8,9,10-tetrahydro-6H-benzo[b]-cyclohepta[d]furan-2-ylamine (0.25 g, 1.2 mmol) provided tert-butyl {(1R,2R)-2-(benzyloxy)-1-[(7,8,9,10-tetrahydro-6H-benzo[b]cyclohepta[d]furan-2-ylamino)carbonyl]propyl}carbamate (0.11 g). MS (ESI) m/z 493 ([M+H]+); MS (ESI) m/z 491 ([M−H]−).

Example 60

1-ACETYL-N-7,8,9,10-TETRAHYDRO-6H-BENZO[B]CYCLOHEPTA[D]FURAN-2-YL-L-PROLINAMIDE

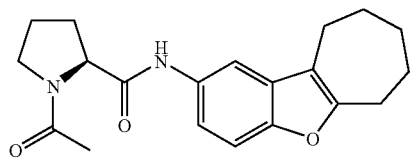

Following the procedure of Example 30, triethylamine (0.21 mL, 1.5 mmol), 1-(3-dimethylaminopropyl)-3-ethylcarbodiimide (0.15 g, 0.78 mmol), N-hydroxybenzotriazole (0.11 g, 0.78 mmol), N-acetyl-L-proline (0.094 g, 0.60 mmol), and 7,8,9,10-tetrahydro-6H-benzo[b]cyclohepta[d]furan-2-ylamine (0.12 g, 0.60 mmol) 1-acetyl-N-7,8,9,10-tetrahydro-6H-benzo[b]cyclohepta[d]furan-2-yl-L-prolinamide (0.13 g). MS (ESI) m/z 341 ([M+H]+); MS (ESI) m/z 339.1 ([M−H]−); HRMS: calcd for $C_{20}H_{24}N_2O_3$+H+, 341.18597; found (ESI, [M+H]+), 341.1863.

Example 61

1-METHYL-N-7,8,9,10-TETRAHYDRO-6H-BENZO[B]CYCLOHEPTA[D]FURAN-2-YL-L-PROLINAMIDE

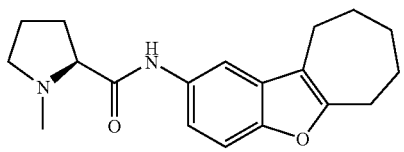

Following the procedure of Example 30, triethylamine (0.21 mL, 1.5 mmol), 1-(3-dimethylaminopropyl)-3-ethylcarbodiimide (0.24 g, 1.3 mmol), N-hydroxybenzotriazole (0.17 g, 1.3 mmol), N-methyl-L-proline (0.077 g, 0.60 mmol), and 7,8,9,10-tetrahydro-6H-benzo[b]-cyclohepta[d]furan-2-ylamine (0.12 g, 0.60 mmol) provided 1-methyl-N-7,8,9,10-tetrahydro-6H-benzo[b]cyclohepta[d]furan-2-yl-L-prolinamide (0.13 g). MS (ES) m/z 313.2 ([M+H]+); HRMS: calcd for $C_{19}H_{24}N_2O_2$+H+, 313.19105; found (ESI, [M+H]+), 313.1918.

Example 62

3,3-DIMETHYL-N-[6,7,8,9,10,11-HEXAHYDROBENZO[B]-CYCLOOCTA[D]FURAN-2-YL]BUTYRAMIDE

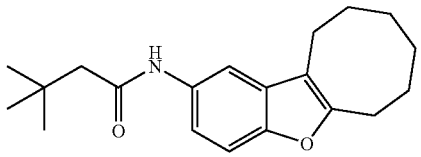

Following the procedure of Example 1, 6,7,8,9,10,11-Hexahydro-benzo[b]-cyclooeta[d]furan-2-ylamine (1.1 g, 5.0 mmol) and t-butylacetyl chloride (0.77 mL, 5.5 mmol) in pyridine (10 mL) provided 3,3-dimethyl-N-[6,7,8,9,10,11-hexahydro-benzo[b]-cyclooeta[d]furan-2-yl]butyramide (0.89 g). Mp 157-158° C.;MS (EI) m/z 314.2 ([M+H]+); Anal. Calcd. for $C_{20}H_{27}NO_2$: C, 76.64; H, 8.68; N, 4.47; Found: C, 76.71; H, 8.81; N, 4.45.

Example 63

2,2-DIMETHYL-N-[6,7,8,9,10,11-HEXAHYDROBENZO[B]-CYCLOOCTA[D]-FURAN-2-YL]PROPIONAMIDE

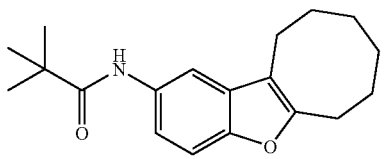

Following the procedure of Example 1, 6,7,8,9,10,11-Hexahydro-benzo[b]-cyclooeta[d]furan-2-ylamine (1.1 g, 5.0 mmol) and trimethylacetyl chloride (0.68 mL, 5.5 mmol) in pyridine (10 mL) provided 2,2-dimethyl-N-[6,7,8,9,10,11-hexahydro-benzo[b]-cycloocta[d]-furan-2-yl]propionamide (0.74 g). Mp 189-190° C.; MS (FAB) m/z 300 ([M+H]+); Anal. Calcd. for $C_{19}H_{25}NO_2$: C, 76.22; H, 8.42; N, 4.68; Found: C, 76.57; H, 8.38; N, 4.62.

Example 64

3-METHYL-N-[6,7,8,9,10,11-HEXAHYDRO-BENZO[B]-CYCLOOCTA[D]-FURAN-2-YL]BUTYRAMIDE

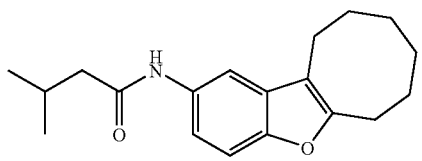

Following the procedure of Example 1, 6,7,8,9,10,11-Hexahydro-benzo[b]-cycloocta[d]furan-2-ylamine (1.1 g, 5.0 mmol) and isovaleryl chloride (0.68 mL, 5.5 mmol) in pyridine (10 mL) provided 3-methyl-N-[6,7,8,9,10,11-hexahydro-benzo[b]-cycloocta[d]-furan-2-yl]butyramide (0.87 g). Mp 154-155° C.; MS (FAB) m/z 300 ([M+H]+); Anal. Calcd. for $C_{19}H_{25}NO_2$: C, 76.22; H, 8.42; N, 4.68; Found: C, 76.07; H, 8.52; N, 4.89.

Example 65

2-CYCLOHEXYL-N-[6,7,8,9,10,11-HEXAHYDRO-BENZO[B]-CYCLOOCTA[D]FURAN-2-YL]ACETAMIDE

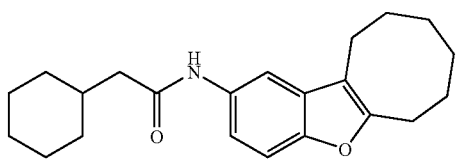

Following the procedure of Example 1, 6,7,8,9,10,11-Hexahydro-benzo[b]-cycloocta[d]furan-2-ylamine (1.1 g, 5.0 mmol) and cyclohexylacetyl chloride (0.88 g, 5.5 mmol) in pyridine (10 mL) provided 2-cyclohexyl-N-[6,7,8,9,10,11-hexahydro-benzo[b]-cycloocta[d]furan-2-yl]acetamide (1.3 g). Mp 180-181° C.;MS (EI) m/z 340 ([M+H]+); Anal. Calcd. for $C_{22}H_{29}NO_2$: C, 77.84; H, 8.61; N, 4.13; Found: C, 77.96; H, 8.70; N, 4.16.

Example 66

N-(6,7,8,9,10,11-HEXAHYDROBENZO[B]CYCLOOCTA[D]FURAN-2-YL)-3,5,5-TRIMETHYLHEXANAMIDE

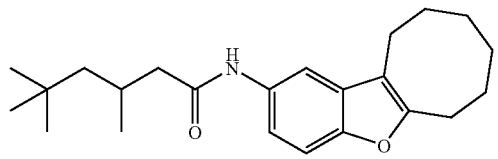

Following the procedure of Example 1, 6,7,8,9,10,11-Hexahydro-benzo[b]-cycloocta[d]furan-2-ylamine (0.15 g, 0.70 mmol), 3,5,5-trimethylhexanoyl chloride (0.14 mL, 0.73 mmol), and poly(vinylpyridine) (0.5 g) in dichloroethane (15 mL) provided N-(6,7,8,9,10,11-hexahydrobenzo[b]cycloocta[d]furan-2-yl)-3,5,5-trimethylhexanamide (0.25 g). MS (ESI) m/z 356 ([M+H]+).

Example 67

N-(6,7,8,9,10,11-HEXAHYDROBENZO[B]CYCLOOCTA[D]FURAN-2-YL)THIOPHENE-2-CARBOXAMIDE

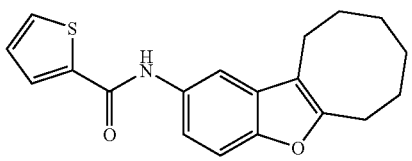

Following the procedure of Example 1, 6,7,8,9,10,11-Hexahydro-benzo[b]-cycloocta[d]furan-2-ylamine (0.15 g, 0.70 mmol), 2-thiophenecarbonyl chloride (0.082 mL, 0.77 mmol), and poly(vinylpyridine) (0.5 g) in dichloromethane (17 mL) provided N-(6,7,8,9,10,11-hexahydrobenzo[b]cycloocta[d]furan-2-yl)thiophene-2-carboxamide (0.098 g). MS (ESI) m/z 326 ([M+H]+).

Example 68

4-TERT-BUTYL-N-(6,7,8,9,10,11-HEXAHYDROBENZO[B]CYCLOOCTA[D]FURAN-2-YL)BENZAMIDE

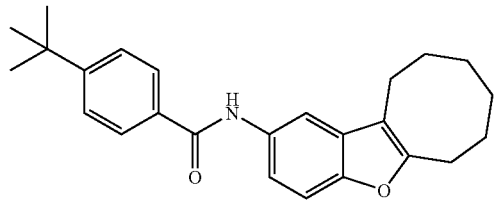

Following the procedure of Example 1, 6,7,8,9,10,11-Hexahydro-benzo[b]-cycloocta[d]furan-2-ylamine (0.15 g, 0.70 mmol), 4-t-butylbenzoyl chloride (0.14 mL, 0.73 mmol), and poly(vinylpyridine) (0.5 g) in dichloromethane

Example 69

N-(6,7,8,9,10,11-HEXAHYDROBENZO[B]CY-CLOOCTA[D]FURAN-2-YL)-3-METHYLBENZA-MIDE

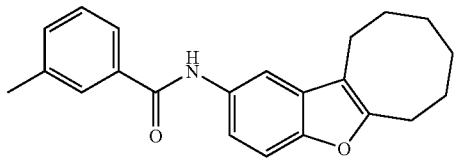

Following the procedure of Example 1, 6,7,8,9,10,11-Hexahydro-benzo[b]-cycloocta[d]furan-2-ylamine (0.15 g, 0.70 mmol), m-toluoyl chloride (0.096 mL, 0.73 mmol), and poly(vinylpyridine) (0.5 g) in dichloromethane (17 mL) provided N-(6,7,8,9,10,11-hexahydrobenzo[b]cycloocta[d]furan-2-yl)-3-methylbenzamide (0.19 g). MS (ESI) m/z 334 ([M+H]+).

Example 70

3-CYCLOPENTYL-N-(6,7,8,9,10,11-HEXAHY-DROBENZO[B]CYCLOOCTA[D]FURAN-2-YL) PROPANAMIDE

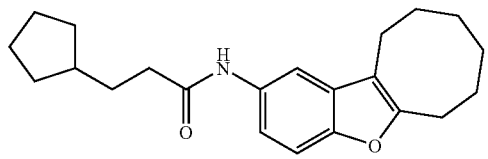

Following the procedure of Example 1, 6,7,8,9,10,11-Hexahydro-benzo[b]-cycloocta[d]furan-2-ylamine (0.13 g, 0.60 mmol), 3-cyclopentylpropionyl chloride (0.10 g, 0.63 mmol), and poly(vinylpyridine) (0.5 g) in dichloromethane (15 mL) provided 3-cyclopentyl-N-(6,7,8,9,10,11-hexahydrobenzo[b]cycloocta[d]furan-2-yl)propanamide (0.13 g). MS (ESI) m/z 340 ([M+H]+).

Example 71

N-(6,7,8,9,10,11-HEXAHYDROBENZO[B]CY-CLOOCTA[D]FURAN-2-YL)HEXANAMIDE

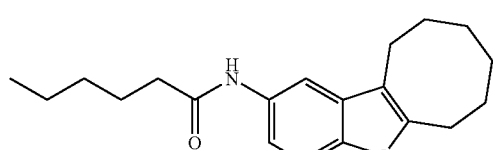

Following the procedure of Example 1, 6,7,8,9,10,11-Hexahydro-benzo[b]-cycloocta[d]furan-2-ylamine (0.15 g, 0.69 mmol), hexanoyl chloride (0.098 mL, 0.69 mmol), and poly(vinylpyridine) (0.5 g) in dichloroethane (8 mL) provided N-(6,7,8,9,10,11-hexahydrobenzo[b]cycloocta[d]furan-2-yl)hexanamide (0.10 g). MS (ESI) m/z 314 ([M+H]+).

Example 72

N-(6,7,8,9,10,11-HEXAHYDROBENZO[B]CY-CLOOCTA[D]FURAN-2-YL)-3-PHENYLPRO-PANAMIDE

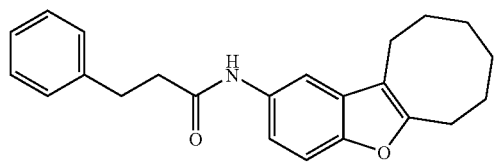

Following the procedure of Example 1, 6,7,8,9,10,11-Hexahydro-benzo[b]-cycloocta[d]furan-2-ylamine (0.15 g, 0.69 mmol), hydrocinnamoyl chloride (0.10 mL, 0.69 mmol), and poly(vinylpyridine) (0.5 g) in dichloroethane (8 mL) provided N-(6,7,8,9,10,11-hexahydrobenzo[b]cycloocta[d]furan-2-yl)-3-phenylpropanamide (0.17 g). MS (ESI) m/z 348 ([M+H]+).

Example 73

N-(6,7,8,9,10,11-HEXAHYDROBENZO[B]CY-CLOOCTA[D]FURAN-2-YL)ACETAMIDE

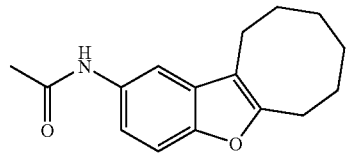

Following the procedure of Example 1, 6,7,8,9,10,11-Hexahydro-benzo[b]-cycloocta[d]furan-2-ylamine (0.15 g, 0.69 mmol), acetyl chloride (0.055 mL, 0.69 mmol), and poly(vinylpyridine) (0.5 g) in dichloroethane (8 mL) provided N-(6,7,8,9,10,11-hexahydrobenzo[b]cycloocta[d]furan-2-yl)acetamide (0.10 g). MS (ESI) m/z 258 ([M+H]+).

Example 74

N-(6,7,8,9,10,11-HEXAHYDROBENZO[B]CY-CLOOCTA[D]FURAN-2-YL)-2-FURAMIDE

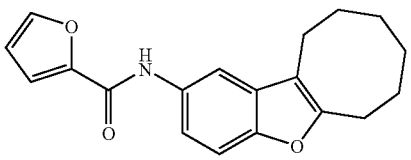

Following the procedure of Example 1, 6,7,8,9,10,11-Hexahydro-benzo[b]-cycloocta[d]furan-2-ylamine (0.15 g, 0.69 mmol), 2-furoyl chloride (0.075 mL, 0.76 mmol), and poly(vinylpyridine) (0.5 g) in dichloromethane (12 mL) provided N-(6,7,8,9,10,11-hexahydrobenzo[b]cycloocta[d]furan-2-yl)-2-furamide (0.17 g). MS (ESI) m/z 310 ([M+H]+).

Example 75

N-(6,7,8,9,10,11-HEXAHYDROBENZO[B]CYCLOOCTA[D]FURAN-2-YL)-2-PHENYLACETAMIDE

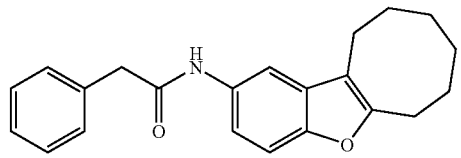

Following the procedure of Example 1, 6,7,8,9,10,11-Hexahydro-benzo[b]-cycloocta[d]furan-2-ylamine (0.20 g, 0.92 mmol), phenylacetyl chloride (0.14 mL, 1.0 mmol), and poly(vinylpyridine) (0.5 g) in dichloroethane (12 mL) provided N-(6,7,8,9,10,11-hexahydrobenzo[b]cycloocta[d]furan-2-yl)-2-phenylacetamide (0.25 g). MS (ESI) m/z 334.3 ([M+H]+).

Example 76

N-(6,7,8,9,10,11-HEXAHYDROBENZO[B]CYCLOOCTA[D]FURAN-2-YL)-2,6-DIMETHOXYBENZAMIDE

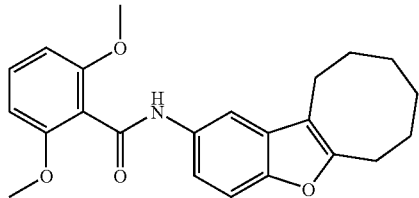

Following the procedure of Example 1, 6,7,8,9,10,11-Hexahydro-benzo[b]-cycloocta[d]furan-2-ylamine (0.15 g, 0.69 mmol), 2,6-dimethoxybenzoyl chloride (0.15 mL, 0.77 mmol), and poly(vinylpyridine) (0.5 g) in dichloroethane (12 mL) N-(6,7,8,9,10,11-hexahydrobenzo[b]cycloocta[d]furan-2-yl)-2,6-dimethoxybenzamide (0.15 g). MS (ESI) m/z 380 ([M+H]+).

Example 77

N-(6,7,8,9,10,11-HEXAHYDROBENZO[B]CYCLOOCTA[D]FURAN-2-YL)ISONICOTINAMIDE

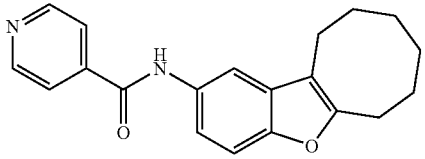

Following the procedure of Example 1, 6,7,8,9,10,11-Hexahydro-benzo[b]-cycloocta[d]furan-2-ylamine (0.20 g, 0.92 mmol), isonicotinoyl chloride hydrochloride (0.20 g, 1.1 mmol), and poly(vinylpyridine) (0.5 g) in dichloroethane (12 mL) provided N-(6,7,8,9,10,11-hexahydrobenzo[b]cycloocta[d]furan-2-yl)isonicotinamide (0.13 g). MS (ESI) m/z 321 ([M+H]+); MS (ESI) m/z 319 ([M−H]−).

Example 78

N-(6,7,8,9,10,11-HEXAHYDROBENZO[B]CYCLOOCTA[D]FURAN-2-YL)-2-PYRIDIN-4-YLACETAMIDE

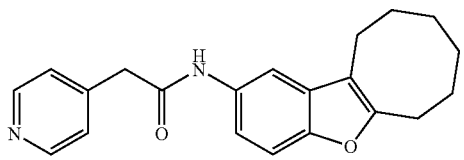

Following the procedure of Example 30, triethylamine (0.40 mL, 2.9 mmol), 1-(3-dimethylaminopropyl)-3-ethylcarbodiimide (0.33 g, 1.7 mmol), N-hydroxybenzotriazole (0.23 g, 1.7 mmol), 4-pyridylacetic acid (0.24 g, 1.4 mmol), and 6,7,8,9,10,11-hexahydro-benzo[b]-cycloocta[d]furan-2-ylamine (0.25 g, 1.2 mmol) provided N-(6,7,8,9,10,11-hexahydrobenzo[b]cycloocta[d]furan-2-yl)-2-pyridin-4-ylacetamide (0.18 g). MS (ESI) m/z 335 ([M+H]+); MS (ESI) m/z 333 ([M−H]−).

Example 79

2-CHLORO-N-6,7,8,9,10,11-HEXAHYDROBENZO[B]CYCLOOCTA[D]FURAN-2-YLACETAMIDE

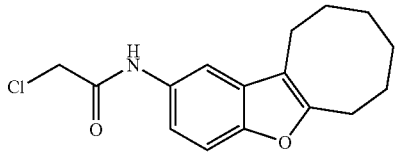

Following the procedure of Example 1, 6,7,8,9,10,11-Hexahydro-benzo[b]-cycloocta[d]furan-2-ylamine (0.80 g, 3.7 mmol), chloroacetyl chloride (0.31 mL, 3.9 mmol), and pyridine (0.60 mL, 7.4 mmol) in dichloroethane (25 mL) provided 2-chloro-N-6,7,8,9,10,11-hexahydrobenzo[b]cycloocta[d]furan-2-ylacetamide (1.1 g). MS (ESI) m/z 292 ([M+H]+).

Example 80

N-6,7,8,9,10,11-HEXAHYDROBENZO[B]CY-CLOOCTA[D]FURAN-2-YL-2-HYDROXYAC-ETAMIDE

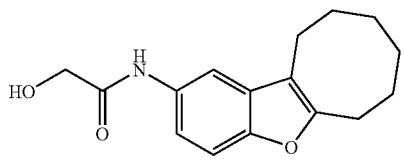

A mixture of 2-chloro-N-6,7,8,9,10,11-hexahydrobenzo[b]cycloocta[d]furan-2-ylacetamide (0.115 g, 0.51 mmol) and cesium carbonate (0.34 g) in water (2 mL) and acetonitrile (4 mL) was heated in the microwave for 15 min. The reaction mixture was concentrated and the crude material was purified by HPLC to provide N-6,7,8,9,10,11-hexahydrobenzo[b]cycloocta[d]furan-2-yl-2-hydroxyacetamide (0.010 g). MS (ESI) m/z 274 ([M+H]+);MS (ESI) m/z 272 ([M−H]−).

Example 81

N-6,7,8,9,10,11-HEXAHYDROBENZO[B]CY-CLOOCTA[D]FURAN-2-YLPENTANAMIDE

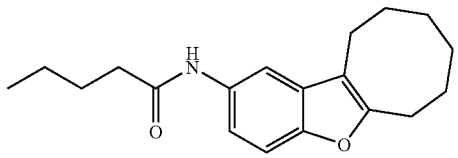

Following the procedure of Example 1, 6,7,8,9,10,11-Hexahydro-benzo[b]-cycloocta[d]furan-2-ylamine (0.10 g, 0.46 mmol), valeryl chloride (0.055 mL, 0.46 mmol), and poly(vinylpyridine) (0.5 g) in dichloromethane (12 mL) provided N-6,7,8,9,10,11-hexahydrobenzo[b]cycloocta[d]furan-2-ylpentanamide (0.099 g). MS m/z 300 ([M+H]+); HRMS: calcd for $C_{19}H_{25}NO_2$ +H+, 300.19581; found (ESI, [M+H]$^+$), 300.1950.

Example 82

N-6,7,8,9,10,11-HEXAHYDROBENZO[B]CY-CLOOCTA[D]FURAN-2-YLHEPTANAMIDE

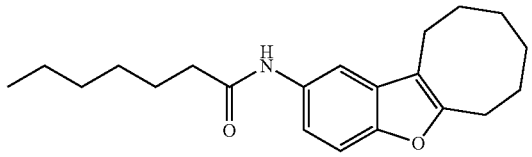

Following the procedure of Example 1, 6,7,8,9,10,11-Hexahydro-benzo[b]-cycloocta[d]furan-2-ylamine (0.10 g, 0.46 mmol), heptanoyl chloride (0.072 mL, 0.46 mmol), and poly(vinylpyridine) (0.5 g) in dichloromethane (12 mL) provided N-6,7,8,9,10,11-hexahydrobenzo[b]cycloocta[d]furan-2-ylheptanamide (0.13 g). MS m/z 328 ([M+H]+); HRMS: calcd for $C_{21}H_{29}NO_2$+H+, 328.22710; found (ESI, [M+H]$^+$), 328.2263.

Example 83

1-TERT-BUTYL-3-(6,7,8,9-TETRAHYDRO-DIBENZOFURAN-2-YL)-UREA

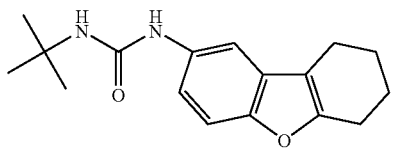

tert-Butylisocyanate (0.55 g, 5.5 mmol) was added to a cooled (0° C.) solution of 6,7,8,9-tetrahydro-dibenzofuran-2-ylamine (0.94 g, 5.0 mmol) in tetrahydrofuran (20 mL). The reaction mixture was stirred for 10 minutes at 0° C. and then allowed to warm to ambient temperature for 5 hours. An additional portion of tert-butylisocyanate (0.65 mL) was added the reaction mixture was stirred overnight. The reaction was incomplete, so pyridine (10 mL) was added and the reaction mixture was heated to reflux for 4.5 hours and then concentrated under reduced pressure. The crude material was dissolved in ethyl acetate and washed with 1 N HCl, water, and brine, dried ($Na_2SO_4$) and concentrated. The crude material was recrystallized from acetonitrile to provide 1-tert-butyl-3-(6,7,8,9-tetrahydro-dibenzofuran-2-yl)-urea (0.71 g). Mp 310-312° C. (DEC); Anal. Calcd. for $C_{17}H_{22}N_2O_2$: C, 71.30; H, 7.74; N, 9.78; Found: C, 71.18; H, 7.84; N, 9.79.

Example 84

1,1-DIETHYL-3-(6,7,8,9-TETRAHYDRO-DIBEN-ZOFURAN-2-YL)-UREA

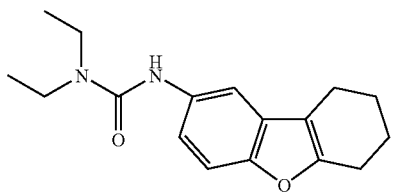

Diethylcarbamoyl chloride (0.72 mL, 5.5 mmol) was added to a solution of 6,7,8,9-tetrahydro-dibenzofuran-2-ylamine (0.94 g, 5.0 mmol) in pyridine (15 mL). The reaction mixture was stirred overnight at room temperature. The crude material was diluted in chloroform and washed with 1 N HCl, water, and brine, dried ($Na_2SO_4$) and concentrated. The crude material was recrystallized from acetonitrile to provide 1,1-diethyl-3-(6,7,8,9-tetrahydro-dibenzofuran-2-yl)-urea (0.78 g). Mp 179-180° C.; Anal. Calcd. for $C_{17}H_{22}N_2O_2$: C, 71.30; H, 7.74; N, 9.78; Found: C, 71.29; H, 7.66; N, 9.72.

Example 85

ETHYL 7,8,9,10-TETRAHYDRO-6H-BENZO[B]CYCLOHEPTA[D]FURAN-2-YLCARBAMATE

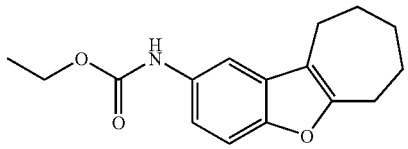

Ethyl chloroformate (0.16 mL, 1.6 mmol) was added to a solution of 7,8,9,10-tetrahydro-6H-benzo[b]-cyclohepta[d]furan-2-ylamine (0.30 g, 1.5 mmol) and pyridine (0.36 mL, 4.5 mmol) in acetonitrile (20 mL). The reaction mixture was stirred overnight at room temperature. The crude material was diluted in ethyl acetate and washed with water, dried (MgSO$_4$) and concentrated. The solid was washed with hexane to provide ethyl 7,8,9,10-tetrahydro-6H-benzo[b]cyclohepta[d]furan-2-ylcarbamate (0.40 g). MS (ESI) m/z 274; Profiled 100% purity, m/z 274.1 ([M+H]+), 2.5 min, Anal. Calcd. for C$_{16}$H$_9$NO$_3$: C, 70.31; H, 7.01; N, 5.12. Found: C, 70.18; H, 6.95; N, 5.01.

Example 86

N-(6,7,8,9,10,11-HEXAHYDROBENZO[B]CYCLOOCTA[D]FURAN-2-YL)MORPHOLINE-4-CARBOXAMIDE

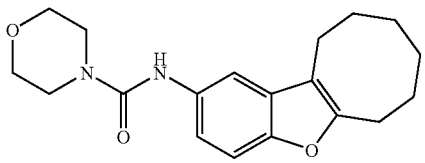

As in Example 1, 6,7,8,9,10,11-Hexahydro-benzo[b]-cycloocta[d]furan-2-ylamine (0.15 g, 0.70 mmol), 4-morpholinecarbonyl chloride (0.085 mL, 0.72 mmol), and poly(vinylpyridine) (0.5 g) in dichloroethane (10 mL) provided N-(6,7,8,9,10,11-hexahydrobenzo[b]cycloocta[d]furan-2-yl)morpholine-4-carboxamide (0.18 g). MS (ESI) m/z 329; Profiled 98% purity, m/z 329.3 ([M+H]+), 2 min, Anal. Calcd. for C$_{19}$H$_{24}$N$_2$O$_3$: C, 69.49; H, 7.37; N, 8.53. Found: C, 69.18; H, 7.15; N, 8.48.

Example 87

N'-(6,7,8,9,10,11-HEXAHYDROBENZO[B]CYCLOOCTA[D]FURAN-2-YL)-N,N-DIMETHYLUREA

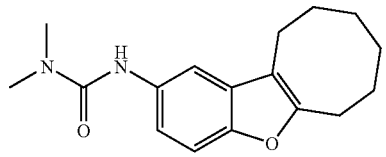

As in Example 1, 6,7,8,9,10,11-Hexahydro-benzo[b]-cycloocta[d]furan-2-ylamine (0.15 g, 0.70 mmol), dimethylcarbamoyl chloride (0.078 mL, 0.73 mmol), and poly(vinylpyridine) (0.5 g) in dichloroethane (10 mL) provided N'-(6,7,8,9,10,11-hexahydrobenzo[b]cycloocta[d]furan-2-yl)-N,N-dimethylurea (0.12 g). MS (ESI) m/z 287; Profiled 100% purity, m/z287.2 ([M+H]+), 2.4 min.

Example 88

ISOPROPYL 6,7,8,9,10,11-HEXAHYDROBENZO[B]CYCLOOCTA[D]FURAN-2-YLCARBAMATE

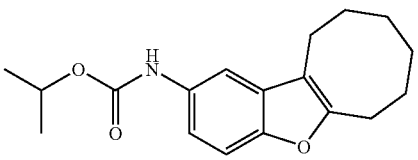

As in Example 1, 6,7,8,9,10,11-Hexahydro-benzo[b]-cycloocta[d]furan-2-ylamine (0.15 g, 0.70 mmol), isopropyl chloroformate (0.084 mL, 0.84 mmol), and poly(vinylpyridine) (0.5 g) in dichloromethane (12 mL) provided isopropyl 6,7,8,9,10,11-hexahydrobenzo[b]cycloocta[d]furan-2-ylcarbamate (0.089 g). MS (ESI) m/z 302; Profiled 100% purity, m/z 302.2 ([M+H]+), 2.7 min; Anal. Calcd for C$_{18}$H$_{23}$NO$_3$: C, 71.73; H, 7.69; N, 4.65. Found: C, 71.48; H, 7.51; N, 4.52.

Assessment of the Ability of Test Compounds to Inhibit Contractions of Isolated Rat Bladder Strips The compounds of the examples were tested to determine their ability to inhibit contractions of isolated rat bladder strips. See Foster, C. D. et al. Br.J.Pharmacol. 97:281-291, 1989; and Fujii, K. et al. Br.J.Pharmacol. 99:779-785,1990. Malmgren, A. et al. J.Urol. 143:828-834,1990, each of which are incorporated herein by reference in its entirety.

Male Sprague-Dawley rats (150-200 g) were obtained from ACE animal suppliers. Animals were allowed free access to food and water.

Animals were euthanized by CO$_2$ asphyxiation followed by a bilateral thoracotomy. The bladder was removed into warm (37 deg. C.) physiological salt solution (PSS) of the following composition (mM): NaCl, 118.4; KCl, 4.7; CaCl$_2$, 2.5; MgSO$_4$.7H2O, 1.2; NaHCO$_3$, 24.9; KH$_2$PO$_4$, 1.2; glucose, 11.1; EDTA, 0.023; gassed with 95% O$_2$/5% CO$_2$; pH 7.4. The bladder was opened and then cut into strips 1-2 mm in width and 7-10 mm in length. The strips were subsequently suspended in a 10 ml tissue bath under an initial resting tension of 1.5 g. The strips were held in place by two surgical clips one of which was attached to a fixed hook while the other was attached to an isometric force transducer. The preparations, which usually exhibit small spontaneous contractions, were allowed to recover for a period of 1 hour prior to a challenge with 0.1 uM carbachol. The carbachol was then washed out and the tissue allowed to relax to its resting level of activity. Following a further 30 minute period of recovery an additional 15 mM KCl were introduced into the tissue bath. This increase in KCl concentration resulted in a large increase in the amplitude of spontaneous contractions (and initiation of contractions in previously quiescent strips) superimposed upon a small increase in basal tone. Following stabilization of this enhanced level of contractile activity, incremental increases in the concentration of test compound or vehicle were introduced into the tissue bath. Contractile activity was measured for each compound or vehicle concentration during the last minute of a 30 minute challenge.

Isometric force developed by the bladder strips was measured using a force transducer and recorded on a polygraph.

Contractile activity was assessed by measuring either the average amplitude of the contractions (baseline to peak force) occurring during a one minute period or, preferably, by integrating the contractile activity with respect to time (one minute measuring period).

The percentage inhibition of contractile activity evoked by each concentration of a given test compounds was used to generate a concentration-response curve. The concentration of test compound required to elicit 50% inhibition of pre-drug contractile activity ($IC_{50}$ concentration) was calculated from this concentration-response curve. The maximum percentage inhibition of contractile activity evoked by a test compound is also recorded for concentrations of test compound <-or 30 uM.

TABLE 1

| Example | $IC_{50}$ (μM) | % Inhibition of Contractility @ 30 μM |
|---|---|---|
| 1 | 0.20-0.70 | — |
| 2 | 1.2-4.0 | — |
| 3 | 3.0-11 | — |
| 4 | 9.1-12 | — |
| 5 | — | 10-30% |
| 6 | — | 10-20% |
| 7 | 10-15 | — |
| 8 | 4-8 | — |
| 9 | 6-8 | — |
| 10 | 10-15 | — |
| 11 | — | 20-30% |
| 12 | — | 20-30% |
| 13 | — | 15-25% |
| 14 | 10-20 | — |
| 15 | — | 10-20% |
| 16 | — | 5-10% |
| 17 | — | 25-30% |
| 18 | — | 40-50% |
| 19 | — | 25-35% |
| 20 | — | 15-40% |
| 21 | — | 10-30% |
| 22 | 1-3 | — |
| 23 | 0.35-0.53 | — |
| 24 | 1-5 | — |
| 25 | 3-8 | — |
| 26 | 0.20-0.70 | — |
| 27 | 0.10-0.40 | — |
| 28 | 1-5 | — |
| 29 | 1-10 | — |
| 30 | — | 30-50% |
| 31 | 3-5 | — |
| 32 | 9-12 | — |
| 33 | 2-3 | — |
| 34 | 0.5-0.8 | — |
| 35 | 6-9 | — |
| 36 | 3-5 | — |
| 37 | — | 20-40% |
| 38 | — | 5-10% |
| 39 | — | 15-35% |
| 40 | 1-3 | — |
| 41 | 1-5 | — |
| 42 | — | 30-40% |
| 43 | 1-3 | — |
| 44 | 1-3 | — |
| 45 | — | 15-25% |
| 46 | 7-9 | — |
| 47 | — | 10% |
| 48 | — | 10-15% |
| 49 | — | 30-40% |
| 50 | 3-5 | — |
| 51 | — | 25-40% |
| 52 | — | 20-30% |
| 53 | — | 15-25% |
| 54 | 6-8 | — |
| 55 | 7-10 | — |
| 56 | 0.3-0.6 | — |
| 57 | — | 20-30% |
| 58 | — | 30-40% |

TABLE 1-continued

| Example | $IC_{50}$ (μM) | % Inhibition of Contractility @ 30 μM |
|---|---|---|
| 59 | 1.5-2.0 | — |
| 60 | 1.3-2.5 | — |
| 61 | 1-3 | — |
| 62 | 1-5 | — |
| 63 | 0.11-0.25 | — |
| 64 | 0.10-0.50 | — |
| 65 | 4-10 | — |
| 66 | — | 5-20% |
| 67 | 0.6-0.8 | — |
| 68 | — | 20-40% |
| 69 | — | 10-20% |
| 70 | — | 15-30% |
| 71 | 0.2-1 | — |
| 72 | 0.8-2.2 | — |
| 73 | 0.40-1.1 | — |
| 74 | 10-15 | — |
| 75 | — | 30-40% |
| 76 | 7-14 | — |
| 77 | — | 30-50% |
| 78 | 10-14 | — |
| 79 | 0.2-0.4 | — |
| 80 | — | 30-50% |
| 81 | — | 10-30% |
| 82 | 0.6-2.0 | — |
| 83 | 4-5 | — |
| 84 | 3-5 | — |
| 85 | — | 40-60% |
| 86 | 7-9 | — |
| 87 | — | 25-35% |
| 88 | — | 20-30% |

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A compound of Formula I:

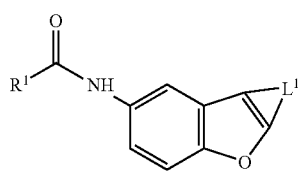

or pharmaceutically acceptable salt thereof, wherein:

$R^1$ is H, $C_{1-12}$alkyl, $C_{2-12}$alkenyl, $C_{2-12}$alkynyl, $C_{1-12}$haloalkyl, $C_{1-12}$haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, heteroarylalkynyl, heteroaryl, heteroarylalkyl, heteroarylalkenyl, heteroarylalkynyl, —$OR^2$, —$SR^2$, or —$NR^3R^4$; wherein said $C_{1-12}$alkyl, $C_{2-12}$alkenyl, $C_{2-12}$alkynyl, $C_{1-12}$haloalkyl, $C_{1-12}$haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, heteroarylalkynyl, heteroaryl, heteroarylalkyl, heteroarylalkenyl, and heteroarylalkynyl are each optionally substituted with 1, 2, 3, or 4 independently selected $R^5$ groups;

L1 is an unsubstituted alkylene bridge each $R^2$, $R^3$, and $R^4$ is, independently, H, $C_{1-6}$alkyl, $C_{1-6}$alkenyl, $C_{1-6}$alkynyl, $C_{1-6}$haloalkyl, cycloalkyl, cycloalkylalkyl, heterocycloalkyl, heterocycloalkylalkyl, aryl, arylalkyl, heteroaryl, or heteroarylalkyl; wherein said $C_{1-6}$alkyl, $C_{1-6}$alkenyl, $C_{1-6}$alkynyl, $C_{1-6}$haloalkyl, cycloalkyl, cycloalkylalkyl, heterocycloalkyl, heterocycloalkylalkyl, aryl, arylalkyl, heteroaryl, and heteroarylalkyl are each optionally substituted with 1, 2, 3, or 4 independently selected $R^7$ groups;

each $R^5$ and $R^7$ is, independently, $OR^a$, $SR^a$, $C(O)R^b$, $C(O)NR^eR^f$, $C(O)OR^b$, $OC(O)R^b$, $OC(O)NR^eR^f$, $NR^eR^f$, $NR^cC(O)R^d$, $NR^cC(O)OR^d$, $NR^cC(O)NR^d$, $S(O)R^b$, $S(O)NR^eR^f$, $S(O)_2R^b$, $NR^cS(O)_2R^d$, $NR^bS(O)_2NR^eR^f$, $C(=NR^a)R^b$, $C(=NR^a)NR^b$, $C(=NR^a)OR^b$, $OC(=NR^a)R^b$, $OC(=NR^a)NR^b$, $NR^cC(=NR^a)R^d$ $NR^cC(=NR^a)OR^d$, $NR^cC(=NR^a)NR^d$, halogen, cyano, nitro, $C_{1-6}$alkyl, $C_{1-6}$alkenyl, $C_{1-6}$alkynyl, $C_{1-6}$haloalkyl, $C_{1-6}$haloalkoxy, cycloalkyl, cycloalkylalkyl, heterocycloalkyl, heterocycloalkylalkyl, aryl, arylalkyl, heteroaryl, or heteroarylalkyl; wherein said $C_{1-6}$alkyl, $C_{1-6}$alkenyl, $C_{1-6}$alkynyl, $C_{1-6}$haloalkyl, $C_{1-6}$alkoxy, $C_{1-6}$haloalkoxy, cycloalkyl, cycloalkylalkyl, heterocycloalkyl, heterocycloalkylalkyl, aryl, arylalkyl, heteroaryl, and heteroarylalkyl are each optionally substituted with 1, 2, 3, or 4 independently selected $R^8$ groups;

each $R^8$ is, independently, $OR^{a'}$, $SR^{a'}$, $C(O)R^{b'}$, $C(O)NR^{e'}R^{f'}$, $C(O)OR^{b'}$, $OC(O)R^{b'}$, $OC(O)NR^{e'}R^{f'}$, $NR^{e'}R^{f'}$, $NR^{c'}C(O)R^{d'}$, $NR^{c'}C(O)OR^{d'}$, $NR^{c'}C(O)NR^{d'}$, $S(O)R^{b'}$, $S(O)NR^{e'}R^{f'}$, $S(O)_2R^{b'}$, $NR^{c'}S(O)_2R^{d'}$, $NR^bS(O)_2NR^{e'}R^{f'}$, halogen, cyano, nitro, hydroxyl, carboxy, $C_{1-6}$alkyl, $C_{1-6}$alkenyl, $C_{1-6}$alkynyl, $C_{1-6}$haloalkyl, $C_{1-6}$alkoxy, $C_{1-6}$haloalkoxy, cycloalkyl, cycloalkylalkyl, cycloalkyloxy, cycloalkylalkyloxy, heterocycloalkyl, heterocycloalkylalkyl, heterocycloalkyloxy, heterocycloalkylalkyloxy, aryl, arylalkyl, aryloxy, arylalkyloxy, heteroaryl, heteroarylalkyl, heteroaryloxy, heteroarylalkyloxy, amino, alkylamino, dialkylamino, acyl, formyl, carbamyl, alkylcarbamyl, dialkylcarbamyl, alkylcarbamyloxy, dialkylcarbamyloxy, acyloxy, alkyloxycarbonyl, carboxy, alkylsulfonyl, alkylsulfinyl, or alkylthio;

each $R^a$, $R^b$, $R^c$, $R^d$, $R^e$, and $R^f$ is, independently, H, $C_{1-6}$alkyl, $C_{1-6}$haloalkyl, $C_{2-6}$alkenyl, $C_{2-6}$alkynyl, cycloalkyl, cycloalkylalkyl, heterocycloalkyl, heterocycloalkylalkyl, aryl, arylalkyl, heteroaryl, or heteroarylalkyl; wherein said $C_{1-6}$alkyl, $C_{1-6}$haloalkyl, $C_{2-6}$alkenyl, $C_{2-6}$alkynyl, cycloalkyl, cycloalkylalkyl, heterocycloalkyl, heterocycloalkylalkyl, aryl, arylalkyl, heteroaryl, and heteroarylalkyl are each optionally substituted with 1, 2, or 3 independently selected $R^g$ groups;

or any $R^c$ and $R^d$, together with the moiety to which they are attached, can form a 3-, 4-, 5-, 6-7- or 8-membered heterocycloalkyl ring, wherein said heterocycloalkyl ring is optionally substituted with 1, 2, or 3 independently selected $R^{g'}$ groups;

or any $R^e$ and $R^f$, together with the nitrogen atom to which they are attached, can form a 3-, 4-, 5-, 6-7- or 8-membered heterocycloalkyl ring or 5-, 6-, 7- or 8-membered heteroaryl ring, wherein said heterocycloalkyl or heteroaryl ring is optionally substituted with 1, 2, or 3 independently selected $R^{g''}$ groups;

each $R^g$ is, independently, $OR^u$, $SR^u$, $C(O)R^v$, $C(O)NR^yR^z$, $C(O)OR^v$, $OC(O)R^v$, $OC(O)NR^yR^z$, $NR^yR^z$, $NR^wC(O)R^x$, $NR^wC(O)OR^x$, $NR^wC(O)NR^x$, halogen, cyano, nitro, $C_{1-6}$alkyl, $C_{1-6}$haloalkyl, $C_{1-6}$haloalkoxy, cycloalkyl, cycloalkylalkyl, heterocycloalkyl, heterocycloalkylalkyl, aryl, arylalkyl, heteroaryl, or heteroarylalkyl;

each $R^{g'}$ and $R^{g''}$ is, independently, halogen, cyano, nitro, hydroxyl, $C_{1-6}$alkyl, $C_{1-6}$haloalkyl, $C_{1-6}$alkoxy, $C_{1-6}$haloalkoxy, cycloalkyl, cycloalkylalkyl, heterocycloalkyl, heterocycloalkylalkyl, aryl, arylalkyl, heteroaryl, heteroarylalkyl, amino, alkylamino, dialkylamino, acyl, formyl, carbamyl, alkylcarbamyl, dialkylcarbamyl, alkylcarbamyloxy, dialkylcarbamyloxy, acyloxy, carboxy, alkylsulfonyl, or alkylsulfinyl;

each $R^{a'}$, $R^{b'}$, $R^{c'}$, $R^{d'}$, $R^{e'}$, and $R^{f'}$ is, independently, H, $C_{1-6}$alkyl, $C_{1-6}$haloalkyl, cycloalkyl, cycloalkylalkyl, heterocycloalkyl, heterocycloalkylalkyl, aryl, arylalkyl, heteroaryl, or heteroarylalkyl;

or any $R^{c'}$ and $R^{d'}$, together with the moiety to which they are attached, can form a 3-, 4-, 5-, 6- 7- or 8-membered heterocycloalkyl ring;

or any $R^{e'}$ and $R^{f'}$, together with the nitrogen atom to which they are attached, can form a 3-, 4-, 5-, 6- 7- or 8-membered heterocycloalkyl ring or 5-, 6-, 7- or 8-membered heteroaryl ring; and each $R^u$, $R^v$, $R^w$, $R^x$, $R^y$, and $R^z$ is, independently, H, $C_{1-6}$alkyl, $C_{1-6}$haloalkyl, cycloalkyl, cycloalkylalkyl, heterocycloalkyl, heterocycloalkylalkyl, aryl, arylalkyl, heteroaryl, or heteroarylalkyl;

provided that the compound is not selected from:
N-(6,7,8,9-tetrahydrodibenzofuran-2-yl)-9H-xanthene-9-acetamide;
2-[(phenylmethylthio)]-N-(6,7,8,9-tetrahydrodibenzofuran-2-yl)-acetamide;
4-oxo-4-[(6,7,8,9-tetrahydro-2-dibenzofuranyl)amino]-butanoic acid methyl ester;
2,2-dimethyl-N,N'-bis(6,7,8,9-tetrahydro-2-dibenzofuranyl)-propanediamide;
3-chloro-N-(6,7,8,9-tetrahydro-2-dibenzofuranyl)benzo[b]thiophene-carboxamide;
2-methoxy-4-(methylthio)-N-(6,7,8,9-tetrahydro-2-dibenzofuranyl)-benzamide;
N-(6,7,8,9-tetrahydro-2-dibenzofuranyl)-cyclohexanecarboxamide;
N-(6,7,8,9-tetrahydro-2-dibenzofuranyl)-cyclopentanecarboxamide;
N-(6,7,8,9-tetrahydro-2-dibenzofuranyl)-3-(trifluoromethyl)-benzamide;
N-(6,7,8,9-tetrahydro-2-dibenzofuranyl)-4-(trifluoromethyl)-benzamide;
1-adamantan-1-yl-3-(6,7,8,9-tetrahydro-dibenzofuran-2-yl)-urea;
N-(3-chlorophenyl)-N'-(6,7,8,9-tetrahydro-2-dibenzofuranyl)-urea;
N-(6,7,8,9-tetrahydro-2-dibenzofuranyl)-1,3-benzodioxole-5-carboxamide;
4-(4-morpholinylsulfonyl)-N-(6,7,8,9-tetrahydro-2-dibenzofuranyl)-benzamide;
8-acetamido-□-methyl-1,2,3,4-tetrahydro-3-dibenzofuranacetic acid methyl ester;
4-(dimethylaminosulfonylamino)-(7,8,9,10-tetrahydro-6H-benzo[b]cyclohepta[d]furan-2-yl)cyclohexanecarboxamide; and
4-(1-pyrrolidinylsulfonyl)-N-(6,7,8,9-tetrahydro-2-dibenzofuranyl)-benzamide;
or pharmaceutically acceptable salt thereof.

2. The compound of claim 1 wherein $R^1$ is H, $C_{1-12}$alkyl, $C_{2-12}$alkenyl, $C_{2-12}$alkynyl, $C_{1-12}$haloalkyl, $C_{1-12}$haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, heteroarylalkynyl, heteroaryl, heteroarylalkyl, heteroarylalkenyl, or heteroarylalkynyl; wherein said $C_{1-12}$alkyl, $C_{2-12}$alkenyl, $C_{2-12}$alkynyl, $C_{1-12}$haloalkyl, $C_{1-12}$haloalkoxy, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, heteroarylalkynyl, heteroaryl, heteroarylalkyl, heteroarylalkenyl, and heteroarylalkynyl are each optionally substituted with 1, 2, 3, or 4 independently selected $R^5$ groups.

3. The compound of claim 1 wherein $R^1$ is H, $C_{1-12}$alkyl, $C_{1-12}$haloalkyl, $C_{1-12}$haloalkoxy, cycloalkyl, cycloalkylalkyl, heterocycloalkyl, heterocycloalkylalkyl, aryl, arylalkyl, heteroaryl, or heteroarylalkyl; wherein said $C_{1-12}$alkyl, $C_{1-12}$haloalkyl, $C_{1-12}$haloalkoxy, cycloalkyl, cycloalkylalkyl, heterocycloalkyl, heterocycloalkylalkyl, aryl, arylalkyl, heteroaryl, and heteroarylalkyl are each optionally substituted with 1, 2, 3, or 4 independently selected $R^5$ groups.

4. The compound of claim 1 wherein $R^1$ is $C_{1-12}$alkyl, $C_{1-12}$haloalkyl, aryl, arylalkyl, cycloalkyl, cycloalkylalkyl, heterocycloalkyl, heterocycloalkylalkyl, heteroaryl, or heteroarylalkyl; wherein $C_{1-12}$alkyl, heterocycloalkyl, heterocycloalkylalkyl, aryl, arylalkyl, and heteroarylalkyl are each optionally substituted with 1, 2, 3, or 4 independently selected $R^5$ groups.

5. The compound of claim 1 wherein $R^1$ is methyl, ethyl, n-propyl, isopropyl, isobutyl, n-butyl, tert-butyl, n-pentyl, isopentyl, neopentyl, 2,4,4-trimethylpentyl, n-hexyl, chloromethyl, adamantan-1-yl, cyclohexylmethyl, cyclopentylethyl, pyrrolidin-2-yl, (morpholin-4-yl)-methyl, (piperazin-1-yl)-methyl, [1,4-dioxa-8-aza-spiro[4.5]decan-N-yl]-methyl, thiophen-2-yl, furan-2-yl, pyridine-4-yl, (thiophen-2-yl)-methyl, (pyridin-4-yl)-methyl, (pyridin-4-yl)-ethyl, phenyl, benzyl, or 2-phenyl-ethyl, wherein each is optionally substituted with 1, 2, 3, or 4 independently selected $R^5$ groups.

6. The compound of claim 1 wherein $R^1$ is $C_{1-12}$alkyl, $C_{1-12}$haloalkyl, aryl, arylalkyl, cycloalkyl, cycloalkylalkyl, heterocycloalkyl, heterocycloalkylalkyl, heteroaryl, or heteroarylalkyl; wherein said is $C_{1-12}$alkyl, heterocycloalkyl, heterocycloalkylalkyl, aryl, arylalkyl, and heteroarylalkyl are each optionally substituted with 1 or 2 $R^5$ groups.

7. The compound of claim 1 wherein $R^1$ is $C_{1-12}$alkyl, heterocycloalkyl, heterocycloalkylalkyl, aryl, arylalkyl, or heteroarylalkyl, each substituted with 1 or 2 $R^5$ groups independently selected from halogen, nitro, $C_{1-12}$alkyl, $C_{1-12}$haloalkyl, heteroaryl, $OR^a$, $NR^eR^f$, $C(O)R^b$, $C(O)OR^b$, $NR^cC(O)OR^d$, and $NR^cC(O)R^d$.

8. The compound of claim 1 wherein $R^1$ is methyl, ethyl, n-propyl, isopropyl, isobutyl, n-butyl, tert-butyl, n-pentyl, isopentyl, neopentyl, 2,4,4-trimethylpentyl, n-hexyl, chloromethyl, adamantan-1-yl, cyclohexylmethyl, cyclopentylethyl, pyrrolidin-2-yl, (morpholin-4-yl)-methyl, (piperazin-1-yl)-methyl, [1,4-dioxa-8-aza-spiro[4.5]decan-N-yl]-methyl, thiophen-2-yl, furan-2-yl, pyridine-4-yl, (thiophen-2-yl)-methyl, (pyridin-4-yl)-methyl, (pyridin-4-yl)-ethyl, phenyl, benzyl, or 2-phenyl-ethyl.

9. The compound of claim 1 wherein $R^1$ is methyl, ethyl, propyl, (piperazin-1-yl)-methyl, pyrrolidin-2-yl, (pyridine-4-yl)ethyl, phenyl, or 2-phenylethyl; wherein each is substituted with 1 or 2 $R^5$ groups independently selected from chloro, fluoro, nitro, methyl, tert-butyl, trifluoromethyl, pyrimidin-2-yl, hydroxyl, methoxy, ethoxy, tert-butoxy, benzyloxy, amino, N-ethyl-N-methylamino, N-methyl-N-(pyridin-2-yl-ethyl)amino, —C(O)CH$_3$, —C(O)CH$_2$CH$_3$, —C(O)O-(tert-butyl), —NHC(O)O-(tert-butyl), —NHC(O)O-(benzyl), and —NHC(O)-(2-phenylethyl); wherein said ethoxy, N-ethyl-N-methylamino, and —NHC(O)-(2-phenylethyl) are each optionally substituted with 1 $R^g$ group selected from N,N-dimethylamino, hydroxyl, and NHC(O)O-(benzyl).

10. The compound of claim 1 wherein $R^1$ is —$NR^3R^4$ or —$OR^2$.

11. The compound of claim 1 wherein $R^1$ is tert-butylamino, dimethylamino, diethylamino, ethoxy, isopropoxy or morpholino.

12. The compound of claim 1 wherein each $R^5$ is, independently, $OR^a$, $SR^a$, $C(O)R^b$, $C(O)NR^eR^f$, $C(O)OR^b$, $OC(O)R^b$, $OC(O)NR^eR^f$, $NR^eR^f$, $NR^cC(O)R^d$, $NR^cC(O)OR^d$, $NR^cC(O)NR^d$, $S(O)R^b$, $S(O)NR^eR^f$, $S(O)_2R^b$, $NR^cS(O)_2R^d$, $NR^hS(O)_2NR^eR^f$, halogen, cyano, nitro, $C_{1-6}$alkyl, $C_{1-6}$alkenyl, $C_{1-6}$alkynyl, $C_{1-6}$haloalkyl, $C_{1-6}$haloalkoxy, cycloalkyl, cycloalkylalkyl, heterocycloalkyl, heterocycloalkylalkyl, aryl, arylalkyl, heteroaryl, or heteroarylalkyl; wherein said $C_{1-6}$alkyl, $C_{1-6}$alkenyl, $C_{1-6}$alkynyl, $C_{1-6}$haloalkyl, $C_{1-6}$haloalkoxy, cycloalkyl, cycloalkylalkyl, heterocycloalkyl, heterocycloalkylalkyl, aryl, arylalkyl, heteroaryl, and heteroarylalkyl are each optionally substituted with 1, 2, 3, or 4 independently selected $R^8$ groups.

13. The compound of claim 1 wherein each $R^5$ is, independently, $OR^a$, $SR^a$, $C(O)R^b$, $C(O)NR^eR^f$, $C(O)OR^b$, $OC(O)R^b$, $OC(O)NR^eR^f$, $NR^eR^f$, $NR^cC(O)R^d$, $NR^cC(O)OR^d$, $NR^cC(O)NR^d$, halogen, cyano, nitro, $C_{1-6}$alkyl, $C_{1-6}$haloalkyl, $C_{1-6}$haloalkoxy, cycloalkyl, cycloalkylalkyl, heterocycloalkyl, heterocycloalkylalkyl, aryl, arylalkyl, heteroaryl, or heteroarylalkyl; wherein said $C_{1-6}$alkyl, $C_{1-6}$haloalkyl, $C_{1-6}$haloalkoxy, cycloalkyl, cycloalkylalkyl, heterocycloalkyl, heterocycloalkylalkyl, aryl, arylalkyl, heteroaryl, and heteroarylalkyl are each optionally substituted with 1, 2, 3, or 4 independently selected $R^8$ groups.

14. The compound of claim 1 wherein each $R^5$ is, independently, $OR^a$, $SR^a$, $C(O)R^b$, $C(O)NR^eR^f$, $C(O)OR^b$, $OC(O)R^b$, $OC(O)NR^eR^f$, $NR^eR^f$, $NR^cC(O)OR^d$, $NR^cC(O)OR^d$, $NR^cC(O)NR^d$, halogen, cyano, nitro, $C_{1-6}$alkyl, $C_{1-6}$haloalkyl, cycloalkyl, heterocycloalkyl, aryl, or heteroaryl; wherein said $C_{1-6}$alkyl, $C_{1-6}$haloalkyl, cycloalkyl, heterocycloalkyl, aryl, and heteroaryl are each optionally substituted with 1, 2, 3, or 4 independently selected $R^8$ groups.

15. The compound of claim 1 wherein each $R^5$ is, independently, $OR^a$, $SR^a$, $C(O)R^b$, $C(O)NR^eR^f$, $C(O)OR^b$, $OC(O)R^b$, $OC(O)NR^eR^f$, $NR^eR^f$, $NR^cC(O)R^d$, $NR^cC(O)OR^d$, $NR^cC(O)NR^d$, halogen, cyano, nitro, $C_{1-6}$alkyl, $C_{1-6}$haloalkyl, cycloalkyl, heterocycloalkyl, aryl, or heteroaryl.

16. The compound of claim 1 wherein each $R^5$ is, independently, $OR^a$, $C(O)R^b$, $C(O)OR^b$, $NR^eR^f$, $NR^cC(O)R^d$, $NR^cC(O)OR^d$, halogen, nitro, $C_{1-6}$alkyl, $C_{1-6}$haloalkyl, or heteroaryl.

17. The compound of claim 1 wherein each $R^5$ is, independently, chloro, fluoro, nitro, methyl, tert-butyl, trifluoromethyl, pyrimidin-2-yl, hydroxyl, methoxy, ethoxy, tert-butoxy, benzyloxy, amino, N-ethyl-N-methylamino, N-methyl-N-(pyridin-2-yl-ethyl)amino, —C(O)CH$_3$, —C(O)CH$_2$CH$_3$, —C(O)O-(tert-butyl), —NHC(O)O-(tert-butyl), —NHC(O)O-(benzyl), and —NHC(O)-(2-phenylethyl); wherein said methyl, tert-butyl, trifluoromethyl, pyrimidin-2-yl, hydroxyl, methoxy, ethoxy, tert-butoxy, benzyloxy, amino, N-ethyl-N-methylamino, N-methyl-N-(pyridin-2-yl-ethyl)amino, —C(O)CH$_3$, —C(O)CH$_2$CH$_3$, —C(O)O-(tert-butyl), —NHC(O)O-(tert-butyl), —NHC(O)O-(benzyl), and —NHC(O)-(2-phenylethyl) are each optionally substituted with 1 $R^g$ group.

18. The compound of claim 1 wherein each $R^g$ is, independently, $OR^u$, $SR^u$, $C(O)R^v$, $C(O)NR^yR^z$, $C(O)OR^v$, $OC(O)R^v$, OC(O)NR$^y$R$^z$, NR$^y$R$^z$, NR$^w$C(O)R$^x$, NR$^w$C(O)OR$^x$, NR$^w$C(O)NR$^x$, halogen, cyano, nitro, C$_{1-6}$alkyl, C$_{1-6}$haloalkyl, C$_{1-6}$haloalkoxy.

19. The compound of claim 1 wherein each R$^g$ is, independently, OR$^u$, NR$^y$R$^z$, or NR$^w$C(O)OR$^x$.

20. The compound of claim 1 wherein each R$^g$ is, independently, N,N-dimethylamino, hydroxyl, and NHC(O)O-(benzyl).

21. The compound of claim 1 wherein L$^1$ is an unsubstituted C$_3$alkylene bridge.

22. The compound of claim 1 wherein L$^1$ is an unsubstituted C$_4$alkylene bridge.

23. The compound of claim 1 wherein L$^1$ is an unsubstituted C$_5$alkylene bridge.

24. The compound of claim 1 wherein L$^1$ is an unsubstituted C$_6$alkylene bridge.

25. The compound of claim 1 wherein:
R$^1$ is C$_{1-12}$alkyl, C$_{1-12}$haloalkyl, aryl, arylalkyl, cycloalkyl, cycloalkylalkyl, heterocycloalkyl, heterocycloalkylalkyl, heteroaryl, or heteroarylalkyl; wherein C$_{1-12}$alkyl, heterocycloalkyl, heterocycloalkylalkyl, aryl, arylalkyl, and heteroarylalkyl are each optionally substituted with 1, 2, 3, or 4 independently selected R$^5$ groups; and
each R$^5$ is, independently, OR$^a$, SR$^a$, C(O)R$^b$, C(O)NR$^e$R$^f$, C(O)OR$^b$, OC(O)R$^b$, OC(O)NR$^e$R$^f$, NR$^e$R$^e$, NR$^c$C(O)R$^d$, NR$^c$C(O)OR$^d$, NR$^c$C(O)NR$^d$, halogen, cyano, nitro, C$_{1-6}$alkyl, C$_{1-6}$haloalkyl, C$_{1-6}$haloalkoxy, cycloalkyl, cycloalkylalkyl, heterocycloalkyl, heterocycloalkylalkyl, aryl, arylalkyl, heteroaryl, or heteroarylalkyl; wherein said C$_{1-6}$alkyl, C$_{1-6}$haloalkyl, C$_{1-6}$haloalkoxy, cycloalkyl, cycloalkylalkyl, heterocycloalkyl, heterocycloalkylalkyl, aryl, arylalkyl, heteroaryl, and heteroarylalkyl are each optionally substituted with 1, 2, 3, or 4 independently selected R$^8$ groups.

26. The compound of claim 1 wherein:
R$^1$ is C$_{1-12}$alkyl, C$_{1-12}$haloalkyl, aryl, arylalkyl, cycloalkyl, cycloalkylalkyl, heterocycloalkyl, heterocycloalkylalkyl, heteroaryl, or heteroarylalkyl; wherein C$_{1-12}$alkyl, heterocycloalkyl, heterocycloalkylalkyl, aryl, arylalkyl, and heteroarylalkyl are each optionally substituted with 1, 2, 3, or 4 independently selected R$^5$ groups; and
each R$^5$ is, independently, OR$^a$, SR$^a$, C(O)R$^b$, C(O)NR$^e$R$^f$, C(O)OR$^b$, OC(O)R$^b$, OC(O)NR$^e$R$^f$, NR$^e$R$^f$, NR$^c$C(O)R$^d$, NR$^c$C(O)OR$^d$, NR$^c$C(O)NR$^d$, halogen, cyano, nitro, C$_{1-6}$alkyl, C$_{1-6}$haloalkyl, cycloalkyl, heterocycloalkyl, aryl, or heteroaryl; wherein said C$_{1-6}$alkyl, C$_{1-6}$haloalkyl, cycloalkyl, heterocycloalkyl, aryl, and heteroaryl are each optionally substituted with 1, 2, 3, or 4 independently selected R$^8$ groups.

27. The compound of claim 1 wherein:
R$^1$ is C$_{1-12}$alkyl, C$_{1-12}$haloalkyl, aryl, arylalkyl, cycloalkyl, cycloalkylalkyl, heterocycloalkyl, heterocycloalkylalkyl, heteroaryl, or heteroarylalkyl; wherein C$_{1-12}$alkyl, heterocycloalkyl, heterocycloalkylalkyl, aryl, arylalkyl, and heteroarylalkyl are each optionally substituted with 1, 2, 3, or 4 independently selected R$^5$ groups; and
each R$^5$ is, independently, OR$^a$, SR$^a$, C(O)R$^b$, C(O)NR$^e$R$^f$, C(O)OR$^b$, OC(O)R$^b$, OC(O)NR$^e$R$^f$, NR$^e$R$^f$, NR$^c$C(O)R$^d$, NR$^c$C(O)OR$^d$, NR$^c$C(O)NR$^d$, halogen, cyano, nitro, C$_{1-6}$alkyl, C$_{1-6}$haloalkyl, cycloalkyl, heterocycloalkyl, aryl, or heteroaryl.

28. The compound of claim 1 wherein:
R$^1$ is C$_{1-12}$alkyl, C$_{1-12}$haloalkyl, aryl, arylalkyl, cycloalkyl, cycloalkylalkyl, heterocycloalkyl, heterocycloalkylalkyl, heteroaryl, or heteroarylalkyl; wherein C$_{1-12}$alkyl, heterocycloalkyl, heterocycloalkylalkyl, aryl, arylalkyl, and heteroarylalkyl are each optionally substituted with 1, 2, 3, or 4 independently selected R$^5$ groups; and
each R$^5$ is, independently, OR$^a$, C(O)R$^b$, C(O)OR$^b$, NR$^e$R$^f$, NR$^c$C(O)R$^d$, NR$^c$C(O)OR$^d$, halogen, nitro, C$_{1-6}$alkyl, C$_{1-6}$haloalkyl, or heteroaryl.

29. The compound of claim 1 wherein:
R$^1$ is C$_{1-12}$alkyl, C$_{1-12}$haloalkyl, aryl, arylalkyl, cycloalkyl, cycloalkylalkyl, heterocycloalkyl, heterocycloalkylalkyl, heteroaryl, or heteroarylalkyl; wherein C$_{1-12}$alkyl, heterocycloalkyl, heterocycloalkylalkyl, aryl, arylalkyl, and heteroarylalkyl are each optionally substituted with 1, 2, 3, or 4 independently selected R$^5$ groups;
each R$^5$ is, independently, OR$^a$, C(O)R$^b$, C(O)OR$^b$, NR$^e$R$^f$, NR$^c$C(O)R$^d$, NR$^c$C(O)OR$^d$, halogen, nitro, C$_{1-6}$alkyl, C$_{1-6}$haloalkyl, or heteroaryl; and
each R$^g$ is, independently, OR$^u$, SR$^u$, C(O)R$^v$, C(O)NR$^y$R$^z$, C(O)OR$^v$, OC(O)R$^v$, OC(O)NR$^y$R$^z$, NR$^y$R$^z$, NR$^w$C(O)R$^x$, NR$^w$C(O)OR$^x$, NR$^w$C(O)NR$^x$, halogen, cyano, nitro, C$_{1-6}$alkyl, C$_{1-6}$haloalkyl, C$_{1-6}$haloalkoxy.

30. The compound of claim 1 wherein:
R$^1$ is C$_{1-12}$alkyl, C$_{1-12}$haloalkyl, aryl, arylalkyl, cycloalkyl, cycloalkylalkyl, heterocycloalkyl, heterocycloalkylalkyl, heteroaryl, or heteroarylalkyl; wherein C$_{1-12}$alkyl, heterocycloalkyl, heterocycloalkylalkyl, aryl, arylalkyl, and heteroarylalkyl are each optionally substituted with 1, 2, 3, or 4 independently selected R$^5$ groups;
each R$^5$ is, independently, OR$^a$, C(O)R$^b$, C(O)OR$^b$, NR$^e$R$^f$, NR$^c$C(O)R$^d$, NR$^c$C(O)OR$^d$, halogen, nitro, C$_{1-6}$alkyl, C$_{1-6}$haloalkyl, or heteroaryl; and
each R$^g$ is, independently, OR$^u$, NR$^y$R$^z$, or NR$^w$C(O)OR$^x$.

31. The compound of claim 1 wherein:
R$^1$ is C$_{1-12}$alkyl, C$_{1-12}$haloalkyl, aryl, arylalkyl, cycloalkyl, cycloalkylalkyl, heterocycloalkyl, heterocycloalkylalkyl, heteroaryl, or heteroarylalkyl; wherein said is C$_{1-12}$alkyl, heterocycloalkyl, heterocycloalkylalkyl, aryl, arylalkyl, and heteroarylalkyl are each optionally substituted with 1 or 2 R$^5$ groups; and
each R$^5$ is, independently, OR$^a$, SR$^a$, C(O)R$^b$, C(O)NR$^e$R$^f$, C(O)OR$^b$, OC(O)R$^b$, OC(O)NR$^e$R$^f$, NR$^e$R$^f$, NR$^c$C(O)R$^d$, NR$^c$C(O)OR$^d$, NR$^c$C(O)NR$^d$, halogen, cyano, nitro, C$_{1-6}$alkyl, C$_{1-6}$haloalkyl, C$_{1-6}$haloalkoxy, cycloalkyl, cycloalkylalkyl, heterocycloalkyl, heterocycloalkylalkyl, aryl, arylalkyl, heteroaryl, or heteroarylalkyl; wherein said C$_{1-6}$alkyl, C$_{1-6}$haloalkyl, C$_{1-6}$haloalkoxy, cycloalkyl, cycloalkylalkyl, heterocycloalkyl, heterocycloalkylalkyl, aryl, arylalkyl, heteroaryl, and heteroarylalkyl are each optionally substituted with 1, 2, 3, or 4 independently selected R$^8$ groups.

32. The compound of claim 1 wherein:
R$^1$ is C$_{1-12}$alkyl, C$_{1-12}$haloalkyl, aryl, arylalkyl, cycloalkyl, cycloalkylalkyl, heterocycloalkyl, heterocycloalkylalkyl, heteroaryl, or heteroarylalkyl; wherein said is C$_{1-12}$alkyl, heterocycloalkyl, heterocycloalkylalkyl, aryl, arylalkyl, and heteroarylalkyl are each optionally substituted with 1 or 2 R$^5$ groups; and
each R$^5$ is, independently, OR$^a$, SR$^a$, C(O)R$^b$, C(O)NR$^e$R$^f$, C(O)OR$^b$, OC(O)R$^b$, OC(O)NR$^e$R$^f$, NR$^e$R$^f$, NR$^c$C(O)R$^d$, NR$^c$C(O)OR$^d$, NR$^c$C(O)NR$^d$, halogen, cyano, nitro, C$_{1-6}$alkyl, C$_{1-6}$haloalkyl, cycloalkyl, heterocycloalkyl, aryl, or heteroaryl; wherein said C$_{1-6}$alkyl, C$_{1-6}$haloalkyl, cycloalkyl, heterocycloalkyl, aryl, and heteroaryl are each optionally substituted with 1, 2, 3, or 4 independently selected R$^8$ groups.

33. The compound of claim 1 wherein:
R$^1$ is C$_{1-12}$alkyl, C$_{1-12}$haloalkyl, aryl, arylalkyl, cycloalkyl, cycloalkylalkyl, heterocycloalkyl, heterocycloalkylalkyl, heteroaryl, or heteroarylalkyl; wherein said is $C_{1-12}$alkyl, heterocycloalkyl, heterocycloalkylalkyl, aryl, arylalkyl, and heteroarylalkyl are each optionally substituted with 1 or 2 $R^5$ groups; and each $R^5$ is, independently, $OR^a$, $SR^a$, $C(O)R^b$, $C(O)NR^eR^f$, $C(O)OR^b$, $OC(O)R^b$, $OC(O)NR^eR^f$, $NR^eR^f$, $NR^cC(O)R^d$, $NR^cC(O)OR^d$, $NR^cC(O)NR^d$, halogen, cyano, nitro, $C_{1-6}$alkyl, $C_{1-6}$haloalkyl, cycloalkyl, heterocycloalkyl, aryl, or heteroaryl.

34. The compound of claim 1 wherein:

$R^1$ is $C_{1-12}$alkyl, $C_{1-12}$haloalkyl, aryl, arylalkyl, cycloalkyl, cycloalkylalkyl, heterocycloalkyl, heterocycloalkylalkyl, heteroaryl, or heteroarylalkyl; wherein said is $C_{1-12}$alkyl, heterocycloalkyl, heterocycloalkylalkyl, aryl, arylalkyl, and heteroarylalkyl are each optionally substituted with 1 or 2 $R^5$ groups; and each $R^5$ is, independently, $OR^a$, $C(O)R^b$, $C(O)OR^b$, $NR^eR^f$, $NR^cC(O)R^d$, $NRC(O)OR^d$, halogen, nitro, $C_{1-6}$alkyl, $C_{1-6}$haloalkyl, or heteroaryl.

35. The compound of claim 1 wherein:

$R^1$ is $C_{1-12}$alkyl, $C_{1-12}$haloalkyl, aryl, arylalkyl, cycloalkyl, cycloalkylalkyl, heterocycloalkyl, heterocycloalkylalkyl, heteroaryl, or heteroarylalkyl; wherein said is $C_{1-12}$alkyl, heterocycloalkyl, heterocycloalkylalkyl, aryl, arylalkyl, and heteroarylalkyl are each optionally substituted with 1 or 2 $R^5$ groups;

each $R^5$ is, independently, $OR^a$, $C(O)R^b$, $C(O)OR^b$, $NR^eR^f$, $NR^cC(O)R^d$, $NR^cC(O)OR^d$, halogen, nitro, $C_{1-6}$alkyl, $C_{1-6}$haloalkyl, or heteroaryl; and each $R^g$ is, independently, $OR^u$, $SR^u$, $C(O)R^v$, $C(O)NR^yR^z$, $C(O)OR^v$, $OC(O)R^v$, $OC(O)NR^yR^z$, $NR^yR^z$, $NR^wC(O)R^x$, $NR^wC(O)OR^x$, $NR^wC(O)NR^x$, halogen, cyano, nitro, $C_{1-6}$alkyl, $C_{1-6}$haloalkyl, $C_{1-6}$haloalkoxy.

36. The compound of claim 1 wherein:

$R^1$ is $C_{1-12}$alkyl, $C_{1-12}$haloalkyl, aryl, arylalkyl, cycloalkyl, cycloalkylalkyl, heterocycloalkyl, heterocycloalkylalkyl, heteroaryl, or heteroarylalkyl; wherein said is $C_{1-12}$alkyl, heterocycloalkyl, heterocycloalkylalkyl, aryl, arylalkyl, and heteroarylalkyl are each optionally substituted with 1 or 2 $R^5$ groups;

each $R^5$ is, independently, $OR^a$, $C(O)R^b$, $C(O)OR^b$, $NR^eR^f$, $NR^cC(O)R^d$, $NR^cC(O)OR^d$, halogen, nitro, $C_{1-6}$alkyl, $C_{1-6}$haloalkyl, or heteroaryl; and each $R^g$ is, independently, $OR^u$, $NR^yR^z$, or $NR^wC(O)OR^x$.

37. The compound of claim 1 wherein:

$R^1$ is methyl, ethyl, n-propyl, isopropyl, isobutyl, n-butyl, tert-butyl, n-pentyl, isopentyl, neopentyl, 2,4,4-trimethylpentyl, n-hexyl, chloromethyl, adamantan-1-yl, cyclohexylmethyl, cyclopentylethyl, pyrrolidin-2-yl, (morpholin-4-yl)-methyl, (piperazin-1-yl)-methyl, [1,4-dioxa-8-aza-spiro[4.5]decan-N-yl]-methyl, thiophen-2-yl, furan-2-yl, pyridine-4-yl, (thiophen-2-yl)-methyl, (pyridin-4-yl)-methyl, (pyridin-4-yl)-ethyl, phenyl, benzyl, or 2-phenyl-ethyl, wherein each is optionally substituted with 1, 2, 3, or 4 independently selected $R^5$ groups; and each $R^5$ is, independently, chloro, fluoro, nitro, methyl, tert-butyl, trifluoromethyl, pyrimidin-2-yl, hydroxyl, methoxy, ethoxy, tert-butoxy, benzyloxy, amino, N-ethyl-N-methylamino, N-methyl-N-(pyridin-2-yl-ethyl)amino, —C(O)CH$_3$, —C(O)CH$_2$CH$_3$, —C(O)O-(tert-butyl), —NHC(O)O-(tert-butyl), —NHC(O)O-(benzyl), and —NHC(O)-(2-phenylethyl); wherein said methyl, tert-butyl, trifluoromethyl, pyrimidin-2-yl, hydroxyl, methoxy, ethoxy, tert-butoxy, benzyloxy, amino, N-ethyl-N-methylamino, N-methyl-N-(pyridin-2-yl-ethyl)amino, —C(O)CH$_3$, —C(O)CH$_2$CH$_3$, —C(O)O-(tert-butyl), —NHC(O)O-(tert-butyl), —NHC(O)O-(benzyl), and —NHC(O)-(2-phenylethyl) are each optionally substituted with 1 $R^g$ group.

38. The compound of claim 1 wherein:

$R^1$ is methyl, ethyl, n-propyl, isopropyl, isobutyl, n-butyl, tert-butyl, n-pentyl, isopentyl, neopentyl, 2,4,4-trimethylpentyl, n-hexyl, chloromethyl, adamantan-1-yl, cyclohexylmethyl, cyclopentylethyl, pyrrolidin-2-yl, (morpholin-4-yl)-methyl, (piperazin-1-yl)-methyl, [1,4-dioxa-8-aza-spiro[4.5]decan-N-yl]-methyl, thiophen-2-yl, furan-2-yl, pyridine-4-yl, (thiophen-2-yl)-methyl, (pyridin-4-yl)-methyl, (pyridin-4-yl)-ethyl, phenyl, benzyl, or 2-phenyl-ethyl, wherein each is optionally substituted with 1, 2, 3, or 4 independently selected $R^5$ groups;

each $R^5$ is, independently, chloro, fluoro, nitro, methyl, tert-butyl, trifluoromethyl, pyrimidin-2-yl, hydroxyl, methoxy, ethoxy, tert-butoxy, benzyloxy, amino, N-ethyl-N-methylamino, N-methyl-N-(pyridin-2-yl-ethyl)amino, —C(O)CH$_3$, —C(O)CH$_2$CH$_3$, —C(O)O-(tert-butyl), —NHC(O)O-(tert-butyl), —NHC(O)O-(benzyl), and —NHC(O)-(2-phenylethyl); wherein said methyl, tert-butyl, trifluoromethyl, pyrimidin-2-yl, hydroxyl, methoxy, ethoxy, tert-butoxy, benzyloxy, amino, N-ethyl-N-methylamino, N-methyl-N-(pyridin-2-yl-ethyl)amino, —C(O)CH$_3$, —C(O)CH$_2$CH$_3$, —C(O)O-(tert-butyl), —NHC(O)O-(tert-butyl), —NHC(O)O-(benzyl), and —NHC(O)-(2-phenylethyl) are each optionally substituted with 1 $R^g$ group; and each $R^g$ is, independently, $OR^u$, $NR^yR^z$, or $NR^wC(O)OR^x$.

39. The compound of claim 1 wherein:

$R^1$ is methyl, ethyl, n-propyl, isopropyl, isobutyl, n-butyl, tert-butyl, n-pentyl, isopentyl, neopentyl, 2,4,4-trimethylpentyl, n-hexyl, chloromethyl, adamantan-1-yl, cyclohexylmethyl, cyclopentylethyl, pyrrolidin-2-yl, (morpholin-4-yl)-methyl, (piperazin-1-yl)-methyl, [1,4-dioxa-8-aza-spiro[4.5]decan-N-yl]-methyl, thiophen-2-yl, furan-2-yl, pyridine-4-yl, (thiophen-2-yl)-methyl, (pyridin-4-yl)-methyl, (pyridin-4-yl)-ethyl, phenyl, benzyl, or 2-phenyl-ethyl, wherein each is optionally substituted with 1, 2, 3, or 4 independently selected $R^5$ groups;

each $R^5$ is, independently, chloro, fluoro, nitro, methyl, tert-butyl, trifluoromethyl, pyrimidin-2-yl, hydroxyl, methoxy, ethoxy, tert-butoxy, benzyloxy, amino, N-ethyl-N-methylamino, N-methyl-N-(pyridin-2-yl-ethyl)amino, —C(O)CH$_3$, —C(O)CH$_2$CH$_3$, —C(O)O-(tert-butyl), —NHC(O)O-(tert-butyl), —NHC(O)O-(benzyl), and —NHC(O)-(2-phenylethyl); wherein said methyl, tert-butyl, trifluoromethyl, pyrimidin-2-yl, hydroxyl, methoxy, ethoxy, tert-butoxy, benzyloxy, amino, N-ethyl-N-methylamino, N-methyl-N-(pyridin-2-yl-ethyl)amino, —C(O)CH$_3$, —C(O)CH$_2$CH$_3$, —C(O)O-(tert-butyl), —NHC(O)O-(tert-butyl), —NHC(O)O-(benzyl), and —NHC(O)-(2-phenylethyl) are each optionally substituted with 1 $R^g$ group; and each $R^g$ is, independently, N,N-dimethylamino, hydroxyl, and NHC(O)O-(benzyl).

40. The compound of claim 1 wherein:

$R^1$ is methyl, ethyl, propyl, (piperazin-1-yl)-methyl, pyrrolidin-2-yl, (pyridine-4-yl)ethyl, phenyl, or 2-phenyl-ethyl; wherein each is substituted with 1 or 2 $R^5$ groups, each $R^5$ is, independently, chloro, fluoro, nitro, methyl, tert-butyl, trifluoromethyl, pyrimidin-2-yl, hydroxyl, methoxy, ethoxy, tert-butoxy, benzyloxy, amino, N-ethyl-N-methylamino, N-methyl-N-(pyridin-2-yl-ethyl)amino, —C(O)CH$_3$, —C(O)CH$_2$CH$_3$, —C(O)O-(tert-butyl), —NHC(O)O-(tert-butyl), —NHC(O)O-

(benzyl), and —NHC(O)-(2-phenylethyl); wherein said ethoxy, N-ethyl-N-methylamino, and —NHC(O)-(2-phenylethyl) are each optionally substituted with 1 R$^g$ group; and each R$^g$ is, independently, N,N-dimethylamino, hydroxyl, or NHC(O)O-(benzyl).

41. The compound of claim 1 wherein:
R$^1$ is —OR$^2$ or —NR$^3$R$^4$; and
L$^1$ is an unsubstituted C$_{4-6}$alkylene bridge.

42. The compound of claim 1 wherein:
R$^1$ is tert-butylamino, dimethylamino, diethylamino, ethoxy, isopropoxy or morpholino; and
L$^1$ is an unsubstituted C$_{4-6}$alkylene bridge.

43. The compound of claim 1 wherein said compound is:
2,2-Dimethyl-N-(6,7,8,9-tetrahydro-dibenzofuran-2-yl)-propionamide;
3-Methyl-N-(6,7,8,9-tetrahydro-dibenzofuran-2-yl)-butyramide;
3,3-Dimethyl-N-(6,7,8,9-tetrahydro-dibenzofuran-2-yl)-butyramide;
2-Phenyl-N-(6,7,8,9-tetrahydro-dibenzofuran-2-yl)-acetamide;
Adamantane-1-carboxylic acid (6,7,8,9-tetrahydro-dibenzofuran-2-yl)-amide;
4-tert-Butyl-N-(6,7,8,9-tetrahydro-dibenzofuran-2-yl)-benzamide;
2-Cyclohexyl-N-(6,7,8,9-tetrahydro-d i benzofuran-2-yl)-acetamide;
N-(6,7,8,9-Tetrahydro-dibenzofuran-2-yl)-propionamide;
N-(6,7,8,9-Tetrahydro-dibenzofuran-2-yl)-isobutyramide;
N-(6,7,8,9-Tetrahydro-dibenzofuran-2-yl)-butyramide;
N-(6,7,8,9-Tetrahydro-dibenzofuran-2-yl)-acetamide;
2-Methyl-N-(6,7,8,9-tetrahydro-dibenzofuran-2-yl)-benzamide;
4-Methoxy-N-(6,7,8,9-tetrahydro-dibenzofuran-2-yl)-benzamide;
4-Methyl-N-(6,7,8,9-tetrahydro-dibenzofuran-2-yl)-pentanamide;
4-Nitro-N-(6,7,8,9-tetrahydro-dibenzofuran-2-yl)-benzamide;
4-Amino-N-(6,7,8,9-tetrahydro-dibenzofuran-2-yl)-benzamide;
4-Chloro-N-(6,7,8,9-tetrahydro-dibenzofuran-2-yl)-benzamide;
N-(6,7,8,9-Tetrahydro-dibenzofuran-2-yl)-benzamide;
4-Fluoro-N-(6,7,8,9-tetrahydrodibenzo[b,d]furan-2-yl)benzamide;
3-Phenyl-N-(6,7,8,9-tetrahydrodibenzo[b,d]furan-2-yl)propanamide;
N-(6,7,8,9-Tetrahydrodibenzo[b,d]furan-2-yl)hexanamide;
N-(2,3-Dihydro-1H-cyclopenta[b]benzofuran-7-yl)-3,3-dimethyl-butyramide;
N-(2,3-Dihydro-1H-cyclopenta(b)benzofuran-7-yl)-2,2-dimethyl-propionamide;
N-(2,3-Dihydro-1H-cyclopenta[b]benzofuran-7-yl)-3-methyl-butyramide;
3,3-Dimethyl-N-[7,8,9,10-tetrahydro-6H-benzo[b]-cyclohepta[d]furan-2-yl]butyramide;
2,2-Dimethyl-N-(6,7,8,9-tetrahydro-5H-10-oxa-benzo[a]azulen-3-yl)-propionamide;
3-Methyl-N-[7,8,9,10-tetrahydro-6H-benzo[b]-cyclohepta[d]furan-2-yl]butyramide;
2-Cyclohexyl-N-[7,8,9,10-tetrahydro-6H-benzo[b]-cyclohepta[d]furan-2-yl]acetamide;
2-(4-Fluorophenyl)-N-(7,8,9,10-tetrahydro-6H-benzo[b]cyclohepta[d]furan-2-yl)acetamide;
N-(7,8,9,10-Tetrahydro-6H-benzo[b]cyclohepta[d]furan-2-yl)pentanamide;
Ethyl 4-oxo-4-(7,8,9,10-tetrahydro-6H-benzo[b]cyclohepta[d]furan-2-ylamino)butanoate;
4-tert-Butyl-N-(7,8,9,10-tetrahydro-6H-benzo[b]cyclohepta[d]furan-2-yl)benzamide;
N-(7,8,9,10-Tetrahydro-6H-benzo[b]cyclohepta[d]furan-2-yl)propanamide;
N-(7,8,9,10-Tetrahydro-6H-benzo[b]cyclohepta[d]furan-2-yl)hexanamide;
3-Phenyl-N-(7,8,9,10-tetrahydro-6H-benzo[b]cyclohepta[d]furan-2-yl)propanamide;
N-(7,8,9,10-Tetrahydro-6H-benzo[b]cyclohepta[d]furan-2-yl)-2-thien-2-ylacetamide;
N-7,8,9,10-Tetrahydro-6H-benzo[b]cyclohepta[d]furan-2-yl-4-(trifluoromethyl)benzamide;
2-Chloro-N-7,8,9,10-tetrahydro-6H-benzo[b]cyclohepta[d]furan-2-ylacetamide;
2-Morpholin-4-yl-N-7,8,9,10-tetrahydro-6H-benzo[b]cyclohepta[d]furan-2-ylacetamide;
N$^2$-[2-(Dimethylamino)ethyl]-N$^2$-methyl-N$^1$-7,8,9,10-tetrahydro-6H-benzo[b]cyclohepta[d]furan-2-ylglycinamide;
N$^2$-Methyl-N$^2$-(2-pyridin-2-ylethyl)-N$^1$-7,8,9,10-tetrahydro-6H-benzo[b]cyclohepta[d]furan-2-ylglycinamide;
2-(1,4-Dioxa-8-azaspiro[4.5]dec-8-yl)-N-7,8,9,10-tetrahydro-6H-benzo[b]cyclohepta[d]furan-2-ylacetamide;
2-(4-Methylpiperazin-1-yl)-N-7,8,9,10-tetrahydro-6H-benzo[b]cyclohepta[d]furan-2-ylacetamide;
2-(2-Hydroxyethoxy)-N-7,8,9,10-tetrahydro-6H-benzo[b]cyclohepta[d]furan-2-ylacetamide;
N$^2$-Ethyl-N$^2$-methyl-N$^1$-7,8,9,10-tetrahydro-6H-benzo[b]cyclohepta[d]furan-2-ylglycinamide;
N$^2$-(2-Hydroxyethyl)-N$^2$-methyl-N$^1$-7,8,9,10-tetrahydro-6H-benzo[b]cyclohepta[d]furan-2-ylglycinamide;
2-tert-Butoxy-N-7, 8,9,10-tetrahydro-6H-benzo[b]cyclohepta[d]furan-2-ylacetamide;
Benzyl [(1S)-1-methyl-2-oxo-2-(7,8,9,10-tetrahydro-6H-benzo[b]cyclohepta[d]furan-2-ylamino)ethyl]carbamate;
2-(4-Pyrimidin-2-ylpiperazin-1-yl)-N-7,8,9,10-tetrahydro-6H-benzo[b]cyclohepta[d]furan-2-ylacetamide;
tert-Butyl [2-oxo-2-(7, 8,9,10-tetrahydro-6H-benzo[b]cyclohepta[d]furan-2-ylamino)ethyl]carbamate;
N$^1$-7,8,9,10-Tetrahydro-6H-benzo[b]cyclohepta[d]furan-2-ylglycinamide;
tert-Butyl [(1S)-1-benzyl-2-oxo-2-(7,8,9,10-tetrahydro-6H-benzo[b]cyclohepta[d]furan-2-ylamino)ethyl]carbamate;
tert-Butyl (2S)-2-[(7,8,9,10-tetrahydro-6H-benzo[b]cyclohepta[d]furan-2-ylamino)carbonyl]pyrrolidine-1-carboxylate;
tert-Butyl [(1S)-2-oxo-1-(pyridin-4-ylmethyl)-2-(7,8,9,10-tetrahydro-6H-benzo[b]cyclohepta[d]furan-2-ylamino)ethyl]carbamate;
tert-Butyl [(1S)-1-methyl-2-oxo-2-(7,8,9,10-tetrahydro-6H-benzo[b]cyclohepta[d]furan-2-ylamino)ethyl]carbamate;
N-7,8,9,10-Tetrahydro-6H-benzo[b]cyclohepta[d]furan-2-yl-L-prolinamide;
N-[(Benzyloxy)carbonyl]-L-phenylalanyl-N$^1$-7,8,9,10-tetrahydro-6H-benzo[b]cyclohepta[d]furan-2-yl-L-alaninamide;

tert-Butyl {(1R,2R)-2-(benzyloxy)-1-[(7,8,9,10-tetrahydro-6H-benzo[b]cyclohepta[d]furan-2-ylamino)carbonyl]propyl}carbamate;

1-Acetyl-N-7,8,9,10-tetrahydro-6H-benzo[b]cyclohepta[d]furan-2-yl-L-prolinamide;

1-methyl-N-7,8,9,10-tetrahydro-6H-benzo[b]cyclohepta[d]furan-2-yl-L-prolinamide;

3,3-Dimethyl-N-[6,7,8,9,10,11-hexahydro-benzo[b]-cycloocta[d]furan-2-yl]butyramide;

2,2-Dimethyl-N-[6,7,8,9,10,11-hexahydro-benzo[b]-cycloocta[d]-furan-2-yl]propionamide;

3-Methyl-N-[6,7,8,9,10,11-hexahydro-benzo[b]-cycloocta[d]-furan-2-yl]butyramide;

2-Cyclohexyl-N-[6,7,8,9,10,11-hexahydro-benzo[b]-cycloocta[d]furan-2-yl]acetamide;

N-(6,7,8,9,10,11-Hexahydrobenzo[b]cycloocta[d]furan-2-yl)-3,5,5-trimethylhexanamide;

N-(6,7,8,9,10,11-Hexahydrobenzo[b]cycloocta[d]furan-2-yl)thiophene-2-carboxamide;

4-tert-Butyl-N-(6,7,8,9,10,11-hexahydrobenzo[b]cycloocta[d]furan-2-yl)benzamide;

N-(6,7,8,9,10,11-Hexahydrobenzo[b]cycloocta[d]furan-2-yl)-3-methylbenzamide;

3-Cyclopentyl-N-(6,7,8,9,10,11-hexahydrobenzo[b]cycloocta[d]furan-2-yl)propanamide;

N-(6,7,8,9,10,11-Hexahydrobenzo[b]cycloocta[d]furan-2-yl)hexanamide;

N-(6,7,8,9,10,11-Hexahydrobenzo[b]cycloocta[d]furan-2-yl)-3-phenylpropanamide;

N-(6,7,8,9,10,11-Hexahydrobenzo[b]cycloocta[d]furan-2-yl)acetamide;

N-(6,7,8,9,10,11-Hexahydrobenzo[b]cycloocta[d]furan-2-yl)-2-furamide;

N-(6,7,8,9,10,11-Hexahydrobenzo[b]cycloocta[d]furan-2-yl)-2-phenylacetamide;

N-(6,7,8,9,10,11-Hexahydrobenzo[b]cycloocta[d]furan-2-yl)-2,6-dimethoxybenzamide;

N-(6,7,8,9,10,11-Hexahydrobenzo[b]cycloocta[d]furan-2-yl)isonicotinamide;

N-(6,7,8,9,10,11-Hexahydrobenzo[b]cycloocta[d]furan-2-yl)-2-pyridin-4-ylacetamide;

2-Chloro-N-6,7,8,9,10,11-hexahydrobenzo[b]cycloocta[d]furan-2-ylacetamide;

N-6,7,8,9,10,11-Hexahydrobenzo[b]cycloocta[d]furan-2-yl-2-hydroxyacetamide;

N-6,7,8,9,10,11-Hexahydrobenzo[b]cycloocta[d]furan-2-ylpentanamide; or

N-6,7,8,9,10,11-Hexahydrobenzo[b]cycloocta[d]furan-2-yl heptanamide;

or pharmaceutically acceptable salt thereof.

44. The compound of claim 1 which is:

1-tert-butyl-3-(6,7,8,9-tetrahydro-dibenzofuran-2-yl)-urea;

1,1-diethyl-3-(6,7,8,9-tetrahydro-dibenzofuran-2-yl)-urea;

ethyl 7,8,9,10-tetrahydro-6H-benzo[b]cyclohepta[d]furan-2-ylcarbamate;

N-(6,7,8,9,10,11-hexahydrobenzo[b]cycloocta[d]furan-2-yl)morpholine-4-carboxamide;

N'-(6,7,8,9,10,11-hexahydrobenzo[b]cycloocta[d]furan-2-yl)-N,N-dimethylurea; or isopropyl 6,7,8,9,10,11-hexahydrobenzo[b]cycloocta[d]furan-2-ylcarbamate;

or pharmaceutically acceptable salt thereof.

45. A pharmaceutical composition comprising a compound of claim 1 and a pharmaceutically acceptable carrier.

\* \* \* \* \*